US008829783B2

(12) United States Patent
Funahashi

(10) Patent No.: US 8,829,783 B2
(45) Date of Patent: Sep. 9, 2014

(54) TRINAPHTHYL MONOAMINE OR DERIVATIVE THEREOF, ORGANIC ELECTROLUMINESCENT DEVICE USING THE SAME, AND ORGANIC ELECTROLUMINESCENT MATERIAL-CONTAINING SOLUTION

(75) Inventor: Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 993 days.

(21) Appl. No.: 12/664,990

(22) PCT Filed: Jun. 17, 2008

(86) PCT No.: PCT/JP2008/061057
§ 371 (c)(1),
(2), (4) Date: Dec. 16, 2009

(87) PCT Pub. No.: WO2008/156088
PCT Pub. Date: Dec. 24, 2008

(65) Prior Publication Data
US 2010/0156285 A1 Jun. 24, 2010

(30) Foreign Application Priority Data
Jun. 18, 2007 (JP) ................ 2007-160010

(51) Int. Cl.
*H05B 33/00* (2006.01)
*H01J 1/62* (2006.01)
*C07F 7/08* (2006.01)
*H05B 33/14* (2006.01)
*C09K 11/06* (2006.01)
*H01L 51/50* (2006.01)
*H01L 51/00* (2006.01)
*C07D 307/91* (2006.01)
*C07C 211/58* (2006.01)

(52) U.S. Cl.
CPC ............. *C09K 11/06* (2013.01); *C07F 7/0818* (2013.01); *H05B 33/14* (2013.01); *H01L 51/5012* (2013.01); *H01L 51/006* (2013.01); *C07C 2103/94* (2013.01); *C09K 2211/1044* (2013.01); *C07C 2101/14* (2013.01); *C09K 2211/1011* (2013.01); *C07D 307/91* (2013.01); *C07F 7/0816* (2013.01); *C09K 2211/1014* (2013.01); *C07C 211/58* (2013.01); *C07C 2103/18* (2013.01); *H01L 51/0094* (2013.01); *C09K 2211/1029* (2013.01); *C09K 2211/1096* (2013.01); *C09K 2211/1007* (2013.01)
USPC ............. 313/504; 313/506; 428/690

(58) Field of Classification Search
USPC ............. 313/504, 506; 428/690, 917
See application file for complete search history.

(56) References Cited

U.S. PATENT DOCUMENTS 5,536,949 A 7/1996 Hosokawa et al.
(Continued)

FOREIGN PATENT DOCUMENTS

| JP | 11 3782 | 1/1989 |
| JP | 9 157643 | 6/1997 |

(Continued)

OTHER PUBLICATIONS

Office Action issued Mar. 27, 2013 in TW application No. 097122734.

*Primary Examiner* — Joseph L Williams
(74) *Attorney, Agent, or Firm* — Oblon, Spivak, McClelland, Maier & Neustadt, L.L.P.

(57) ABSTRACT

Provided is a trinaphthyl monoamine or a derivative thereof. Also provided is an organic electroluminescence device, wherein an organic thin film composed of one or more layers including at least a light-emitting layer is sandwiched between a cathode and an anode, and at least one layer in the organic thin film contains the trinaphthyl monoamine or a derivative thereof by itself or as a component of a mixture. Further provided is organic-electroluminescent-material-containing solution which contains a solvent and the trinaphthyl monoamine or a derivative thereof as an organic electroluminescent material.

24 Claims, 1 Drawing Sheet

(56) References Cited

U.S. PATENT DOCUMENTS

| | | |
|---|---|---|
| 5,635,308 A | 6/1997 | Inoue et al. |
| 6,713,192 B2 | 3/2004 | Fukuoka et al. |
| 6,929,872 B2 | 8/2005 | Mori et al. |
| 7,470,472 B2 | 12/2008 | Funahashi |
| 2005/0260442 A1 | 11/2005 | Yu et al. |
| 2006/0052641 A1 | 3/2006 | Funahashi |
| 2006/0269781 A1 | 11/2006 | Lai et al. |
| 2007/0141393 A1 | 6/2007 | Klubek et al. |
| 2009/0072716 A1 | 3/2009 | Funahashi |

FOREIGN PATENT DOCUMENTS

| | | |
|---|---|---|
| JP | 11 260551 | 9/1999 |
| JP | 2003 201472 | 7/2003 |
| JP | 2005 259472 | 9/2005 |
| TW | 200734286 A | 9/2007 |

TRINAPHTHYL MONOAMINE OR DERIVATIVE THEREOF, ORGANIC ELECTROLUMINESCENT DEVICE USING THE SAME, AND ORGANIC ELECTROLUMINESCENT MATERIAL-CONTAINING SOLUTION

This application is the U.S. National Stage of International Application No. PCT/JP2008/061057, filed Jun. 17, 2008.

TECHNICAL FIELD

The present invention relates to a trinaphthyl monoamine or a derivative thereof, and to an organic electroluminescence device using the same, and an organic-electroluminescent-material-containing solution. Especially, the present invention relates to an organic electroluminescence device which has long lifetime, exhibits a high efficiency of light emission and is capable of emitting a blue light having high color purity, as well as trinaphthyl monoamine or a derivative thereof capable of realizing such electroluminescence device, and an organic-electroluminescent-material-containing solution.

BACKGROUND ART

The organic electroluminescence (EL) devices made by using organic substances have been expected to be applied to production of large area full-color display devices of a solid light emission type at low costs, and have been intensively developed. In general, the organic EL devices are constituted from a light emitting layer and a pair of counter electrodes between which the light emitting layer is sandwiched. In the organic EL devices, when an electric field is applied between the electrodes, electrons are injected from a cathode into the light emitting layer, whereas holes are injected from an anode into the light emitting layer. The electrons and holes injected are recombined in the light emitting layer, so that the light emitting layer is brought into a excited state. When the light emitting layer is returned from the excited state to a ground state, energy is released in the form of light.

The conventional organic EL devices require a high drive voltage and exhibit a low luminance and a low efficiency of light emission as compared to inorganic light emitting diodes. In addition, the conventional organic EL devices suffer from remarkable deterioration in properties and, therefore, are still practically unusable. Although recent organic EL devices are improved step by steps, it has been still demanded to develop organic EL devices with an enhanced efficiency of light emission and with a prolonged lifetime. For example, there is disclosed such a technique using a single monoanthracene compound as an organic light-emitting material (Patent Document 1). However, in this technique, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technique using a single bisanthracene compound as an organic light emitting material (Patent Document 2). However, in this technique, an efficiency of light emission obtained by using the material is also as low as about 1 to 3 cd/A. Therefore, further improvement of the technique has been demanded for rendering it practically usable. On the other hand, there have been proposed long-life organic EL devices using a distyryl compound as an organic light-emitting material to which styrylamine, etc., is added (Patent Document 4). However, the organic EL devices still fail to exhibit a sufficiently long life and, therefore, further improvement of these devices has been required.

Further, there are disclosed techniques using a mono- or bis-anthracene compound together with a distyryl compound in an organic light emitting medium layer (Patent Document 4). However, in these techniques, the wavelength of emission spectra is too long owing to a conjugated structure of the styryl compound, resulting in poor color purity of light emission. In addition, Patent Document 5 discloses a blue light-emitting device using a diaminochrysene derivative.

However, despite the superiority in light emission efficiency, because the device is not sufficient in its lifetime, further improvement was required.

In addition, Patent Document 6 discloses an organic EL device using a tetra(aryl)ethene derivative. However, when the tetra(aryl)ethene derivative is used for the light emitting layer, the color of the light emission tends to change into bluish green and it is not possible to obtain a blue light emission with high color purity.

Further, Patent Document 7 discloses an organic EL device using naphthalene having amino group at its 2-position and 6-position, and Patent Document 8 discloses an organic EL device using naphthalene having amino group at its 1-position and 5-position. However, the organic EL devices still fail to exhibit a sufficiently long lifetime and, therefore, further improvement of these devices has been required.

Patent Document 1: JP 11-3782A

Patent Document 2: JP 8-12600A

Patent Document 3: PCT publication WO 94/006157

Patent Document 4: JP 2001-284050A

Patent Document 5: PCT publication WO 04/044088

Patent Document 6: JP 11-260551A

Patent Document 7: PCT publication WO 06/001223

Patent Document 8: JP 2006-306745A

DISCLOSURE OF THE INVENTION

Problems to be Solved by the Invention

The present invention has been made to overcome the above problems and has an object of providing an organic EL device with a prolonged lifetime, an enhanced efficiency of light emission, a blue light emission of high color purity, and an object of providing a trinaphthyl monoamine or a derivative thereof capable of realizing the EL device, and an organic-electroluminescent-material-containing solution.

Means for Solving the Problem

As a result of extensive researches for developing trinaphthyl monoamine or a derivative thereof having the above suitable properties and organic EL devices using the trinaphthyl monoamine or a derivative thereof, the inventors have found that the object of the present invention can be achieved by employing a trinaphthyl monoamine or a derivative thereof having specified structures represented by any one of following general formulae (I) to (III). The present invention has been accomplished on the basis of the above finding.

Namely, the present invention provides a trinaphthyl monoamine or a derivative thereof represented by any one of the following general formulae (I) to (III):

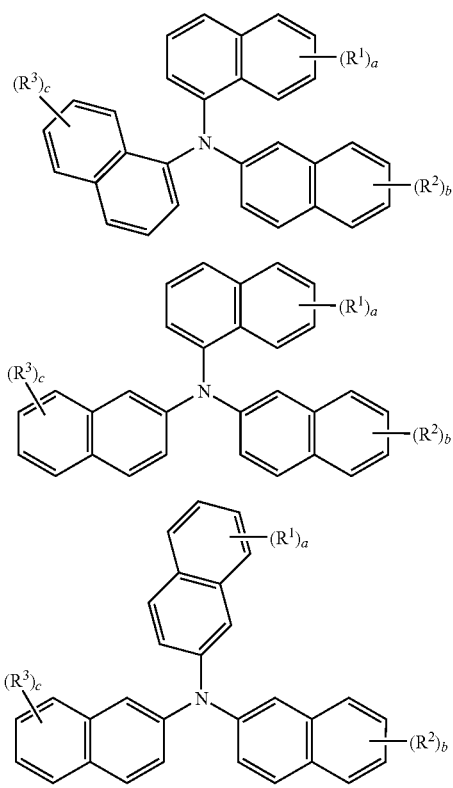

where: $R^1$ to $R^3$ each independently represents a substituted or unsubstituted alkyl group having 1 to 50 carbon atoms,
a substituted or unsubstituted aryl group having 6 to 50 carbon atoms,
a substituted or unsubstituted aralkyl group having 7 to 50 carbon atoms,
a substituted or unsubstituted cycloalkyl group having 3 to 50 carbon atoms,
a substituted or unsubstituted alkoxyl group having 1 to 50 carbon atoms,
a substituted or unsubstituted aryl alkenyl group having 8 to 50 carbon atoms,
a substituted or unsubstituted aryloxy group having 6 to 50 carbon atoms,
a substituted or unsubstituted silyl group having 1 to 20 carbon atoms,
a substituted or unsubstituted heterocyclic group having 5 to 50 carbon atoms, or
a substituent represented by the following structure (A):

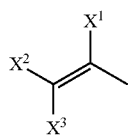

where: $X^1$ to $X^3$ each independently represents a hydrogen atom,
a substituted or unsubstituted alkyl group having 1 to 50 carbon atoms,
a substituted or unsubstituted aryl group having 6 to 50 carbon atoms,
a substituted or unsubstituted cycloalkyl group having 3 to 50 carbon atoms,
a substituted or unsubstituted heterocyclic group having 5 to 50 carbon atoms;
a, b, and c each independently represents an integer of 0 to 7;
when a is 2 or greater, plural $R^1$'s may be identical to or different from each other, and adjacent $R^1$'s may be bonded with each other to form an unsaturated ring;
when b is 2 or greater, plural $R^2$'s may be identical to or different from each other, and adjacent $R^2$'s may be bonded with each other to form an unsaturated ring; and
when c is 2 or greater, plural $R^3$'s may be identical to or different from each other, and adjacent $R^3$'s may be bonded with each other to form an unsaturated ring.

Further, the present invention provides an organic EL device which is composed of one or more organic thin film layers including at least one light emitting layer sandwiched between a cathode and an anode, wherein at least one of the organic thin film layers contains the above trinaphthyl monoamine or a derivative thereof singly or in combination of two or more.

Furthermore, the present invention provides an organic-electroluminescent-material-containing solution including the above trinaphthyl monoamine or a derivative thereof as the material for the organic EL and a solvent.

The organic EL device using the trinaphthyl monoamine or a derivative thereof according to the present invention can exhibit a practically sufficient luminance of light emission even upon applying a low voltage thereto, and has a high efficiency of light emission, and the device is free from deterioration in properties even after being used for a long period of time and, therefore, has a long lifetime.

PREFERRED EMBODIMENT TO CARRY OUT THE INVENTION

Figure 1:
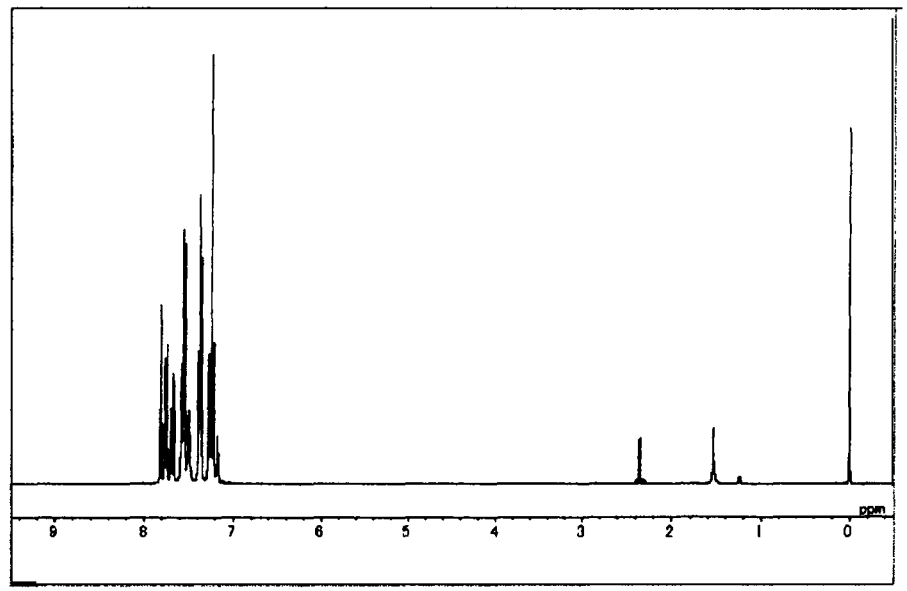
FIG. 1 is a diagram showing $^1$H-NMR spectrum of Compound D-12, which is obtained in Synthesis Example 1.

The trinaphthyl monoamine or a derivative thereof in the present invention is represented by any one of the following general formulae (I) to (III):

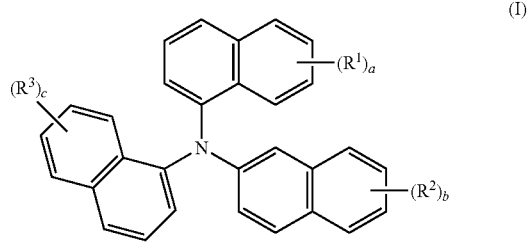

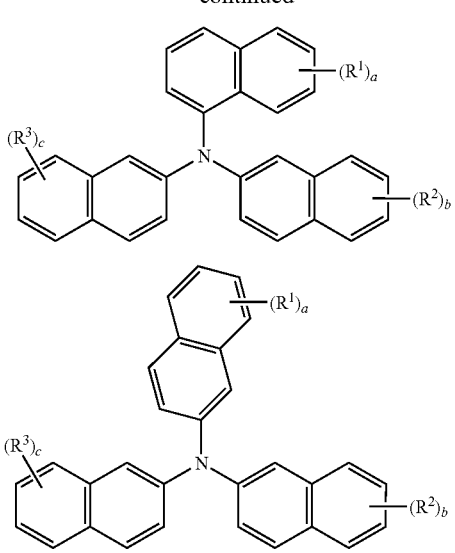

where: $R^1$ to $R^3$ each independently represents a substituted or unsubstituted alkyl group having 1 to 50 carbon atoms, a substituted or unsubstituted aryl group having 6 to 50 carbon atoms, a substituted or unsubstituted aralkyl group having 7 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted arylalkenyl group having 8 to 50 carbon atoms, a substituted or unsubstituted aryloxy group having 6 to 50 carbon atoms, a substituted or unsubstituted silyl group having 1 to 20 carbon atoms, a substituted or unsubstituted heterocyclic group having 5 to 50 carbon atoms or a substituent represented by the following structure (A):

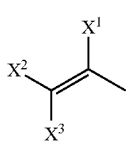

where $X^1$ to $X^3$ each independently represents a hydrogen atom, a substituted or unsubstituted alkyl group having 1 to 50 carbon atoms, a substituted or unsubstituted aryl group having 6 to 50 carbon atoms, a substituted or unsubstituted cycloalkyl group having 3 to 50 carbon atoms or a substituted or unsubstituted heterocyclic group having 5 to 50 carbon atoms.

Examples of the alkyl group having 1 to 50 carbon atoms represented by $R^1$ to $R^3$ and $X^1$ to $X^3$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, etc.

Examples of the aryl group having 6 to 50 carbon atoms represented by $R^1$ to $R^3$ and $X^1$ to $X^3$ include phenyl group, 2-methylphenyl group, 3-methylphenyl group, 4-methylphenyl group, 4-ethylphenyl group, biphenyl group, 4-methylbiphenyl group, 4-ethylbiphenyl group, 4-cyclohexylbiphenyl group, terphenyl group, 3,5-dichlorophenyl group, naphthyl group, 5-methylnaphthyl group, anthryl group, pyrenyl group, fluorenyl group, chrycenyl group, etc.

Examples of the substituted or unsubstituted aralkyl group having 7 to 50 carbon atoms represented by $R^1$ to $R^3$ include benzyl group, 1-phenylethyl group, 2-phenylethyl group, 1-phenylisopropyl group, 2-phenylisopropyl group, phenyl-t-butyl group, β-naphthylmethyl group, 1-α-naphthyl ethyl group, 2-α-naphthyl ethyl group, 1-α-naphthyl isopropyl group, 2-α-naphthyl isopropyl group, 6-naphthylmethyl group, 1-β-naphthyl ethyl group, 2-β-naphthyl ethyl group, 1-β-naphthyl isopropyl group, 2-β-naphthyl isopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group, etc.

Examples of the cycloalkyl group having 3 to 50 carbon atoms represented by $R^1$ to $R^3$ and $X^1$ to $X^3$ include cyclopropyl group, cyclobutyl group, cyclopentyl group, cyclohexyl group, cycloheptyl group, cyclooctyl group, cyclononyl group, bicycloheptyl group, bicyclooctyl group, tricycloheptyl group, adamantyl group, etc. Among those, cyclopentyl group, cyclohexyl group, cycloheptyl group, bicycloheptyl group, bicyclooctyl group, and adamantyl group are preferable.

Examples of the alkoxyl group having 1 to 50 carbon atoms represented by $R^1$ to $R^3$ include methoxy group, ethoxy group, propoxy group, isopropoxy group, butoxy group, isobutoxy group, sec-butoxy group, tert-butoxy group, various pentyloxy groups, various hexyloxy groups, etc.

Examples of the alkenyl group in the arylalkenyl group having 8 to 50 carbon atoms represented by $R^1$ to $R^3$ include vinyl group, allyl group, 2-butenyl group, 3-pentenyl group, etc.

Examples of the aryloxy group having 6 to 50 carbon atoms represented by $R^1$ to $R^3$ include phenoxy group, tolyloxy group, naphthyloxy group, etc.

Examples of the arylamino group having 6 to 50 carbon atoms represented by $R^1$ to $R^3$ include diphenylamino group, ditolylamino group, dinaphthylamino group, naphthylphenylamino group, etc.

Examples of the alkylamino group having 1 to 20 carbon atoms represented by $R^1$ to $R^3$ include dimethylamino group, diethylamino group, dihexylamino group, etc.

Examples of the silyl group having 1 to 20 carbon atoms represented by $R^1$ to $R^3$ include silyl group, trimethylsilyl group, triethylsilyl group, tripropylsilyl group, triphenylsilyl group, butyldimethylsilyl group, propyldimethylsilyl group, vinyldimethylsilyl group, t-butyldimethylsilyl group, etc.

Examples of the heterocyclic group having 5 to 50 carbon atoms represented by $R^1$ to $R^3$ and $X^1$ to $X^3$ include moieties of imidazole, benzimidazole, pyrrole, furan, thiophene, benzothiophene, oxadiazoline, indoline, carbazole, pyridine, quinoline, isoquinoline, benzoquinone, pyrazoline, imidazolidine, piperidine, etc.

Examples of the substituent groups of each group in the general formulae (I) to (III) include a substituted or unsubstituted aryl group having 6 to 50 carbon atoms forming a ring (ring carbon atoms), a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 6 to 50 ring carbon atoms, a substituted or unsubstituted arylthio group having 5 to 50 ring carbon atoms, a substituted or unsubstituted alkoxycarbonyl group having 2 to 50 carbon atoms, an amino group, a halogen atom, a cyano group, a nitro group, a hydroxyl group, a carboxyl group, etc.

In the general formulae (I) to (III), a, b and c each independently represents an integer of 0 to 7 respectively, and it is preferable that a is 1 to 3, b is 1 to 3, and c is 1 to 3, it is further preferable that a is 1 or 2, b is 1 or 2, and c is 1 or 2.

In the general formulae (I) to (III) when a is 2 or greater, plural $R^1$'s may be identical to or different from each other, and adjacent $R^1$'s may be bonded with each other to form an unsaturated ring. Further, in the case where both b and c are 2 or more, it is also the same as the above description.

Examples of the ring structure formed by bonding of $R^1$'s each other, $R^2$'s each other, and $R^3$'s each other include cycloalkane having 4 to 12 carbon atoms such as cyclobutane, cyclopentane, cyclohexane, etc.; cycloalkene having 4 to 12 carbon atoms such as cyclobutene, cyclopentene, cyclohexene, cycloheptene, cyclooctene, etc.; cycloalkadiene having 6 to 12 carbon atoms such as cyclohexadiene, cycloheptadiene, cyclooctadiene, etc.; and a heterocyclic hydrocarbon having 9 to 30 carbon atoms such as indene, phenalene, fluorene, etc.

The general formula (I) is preferably a trinaphthyl monoamine derivative represented by the following general formula (I'), and further preferably represented by the following general formula (I"):

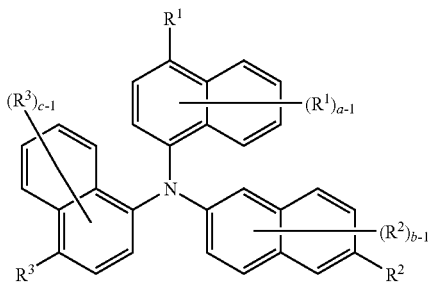
(I')

with the proviso that a, b and c each independently represents an integer of 1 to 7.

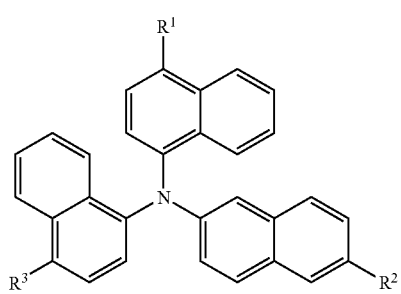
(I")

The general formula (II) is preferably a trinaphthyl monoamine derivative represented by the following general formula (II'), and further preferably represented by the following general formula (II").

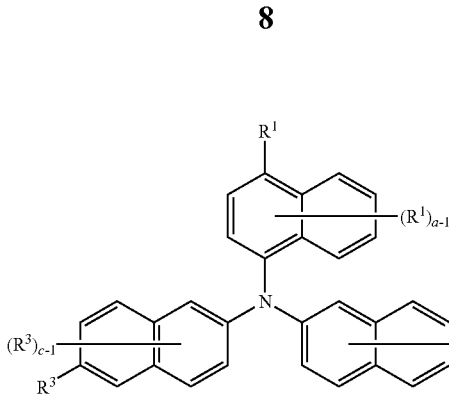
(II')

with the proviso that a, b and c each independently represents an integer of 1 to 7.

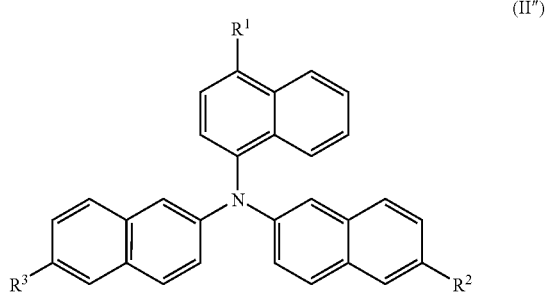
(II")

The general formula (III) is preferably a trinaphthyl monoamine derivative represented by the following general formula (III'), and further preferably represented by the following general formula (III"):

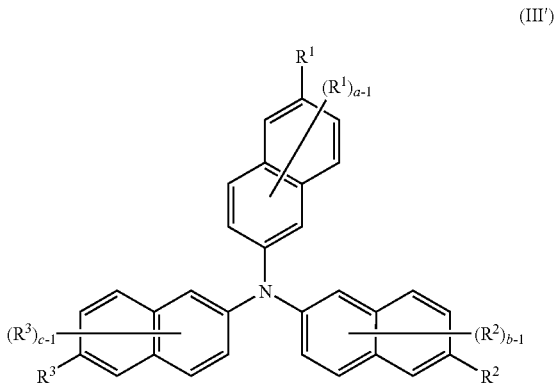
(III')

with the proviso that a, b and c each independently represents an integer of 1 to 7.

(III″)

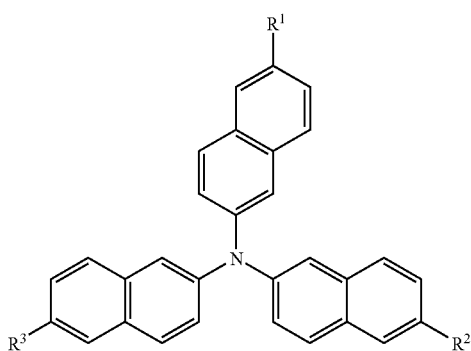

Regarding with the trinaphthyl monoamine derivative represented by the general formulae (I) to (III), it is preferable that $R^1$, $R^2$ and $R^3$ are identical to each other. Moreover, among previously explained structure (A), it is preferable that $X^1$ and $X^2$ are hydrogen atoms, and that $X^3$ is any one of a phenyl group, a naphthyl group and a fluorenyl group.

Specific examples of the trinaphthyl monoamine derivative represented by the general formulae (I) to (III) include the following compounds enumerated below, though not particularly limited thereto. Meanwhile, in the following compounds, Me represents a methyl group.

D-1

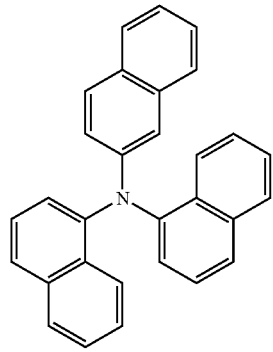

D-2

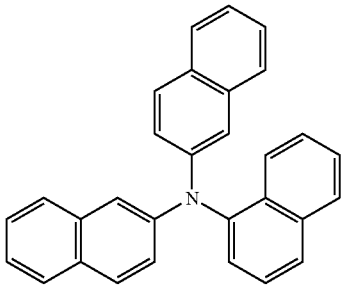

D-3

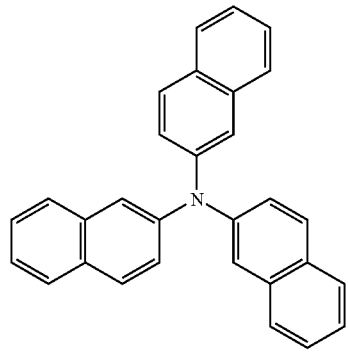

D-4

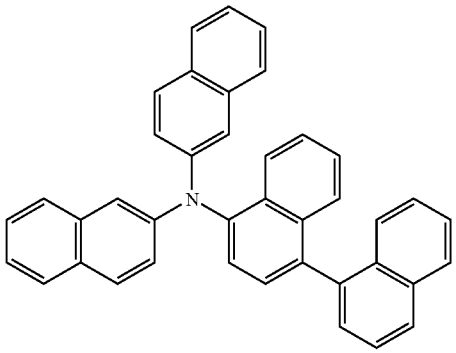

D-5

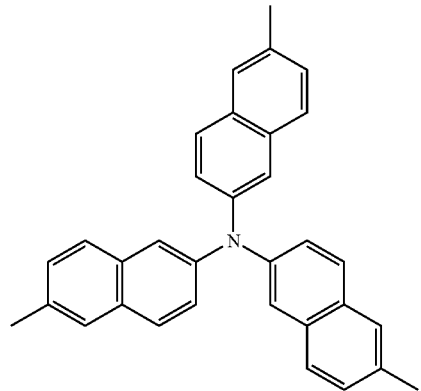

D-6

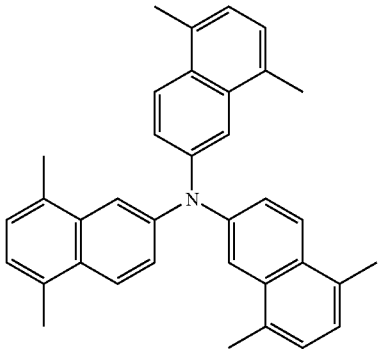

-continued
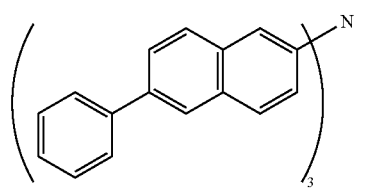
D-7
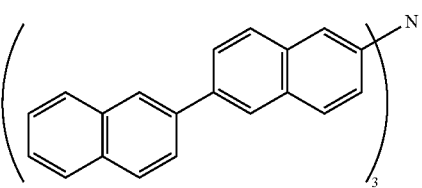
D-8
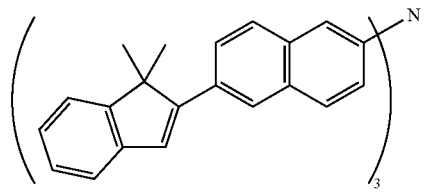
D-9
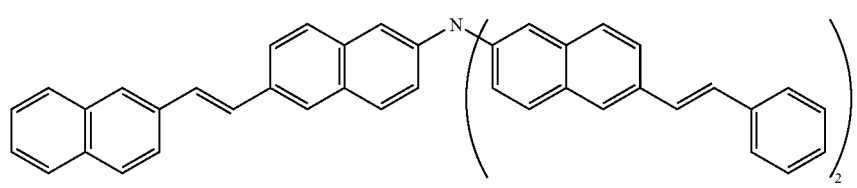
D-10
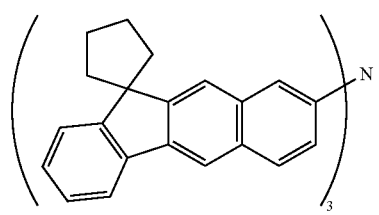
D-11
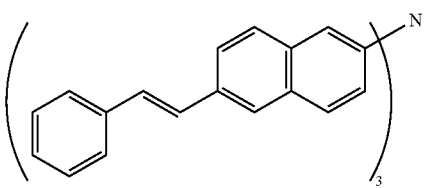
D-12
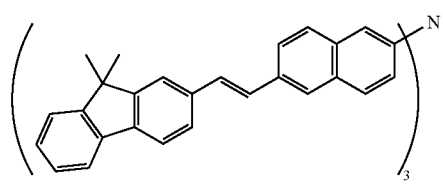
D-13
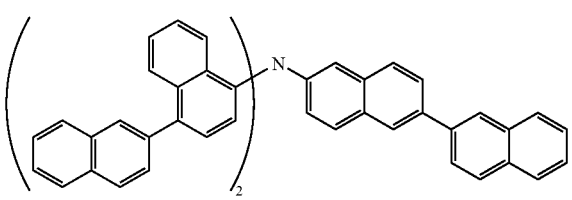
D-14
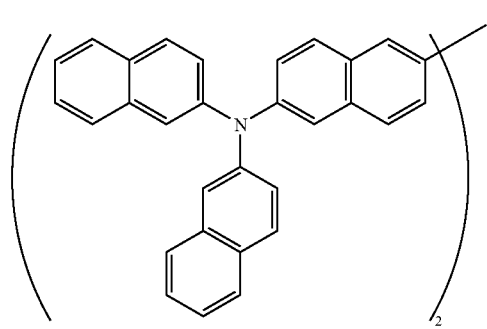
D-15
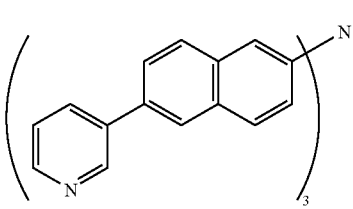
D-16
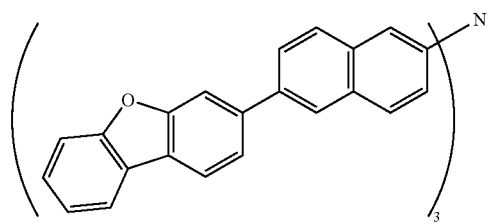
D-17
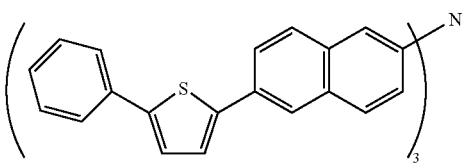
D-18

D-19
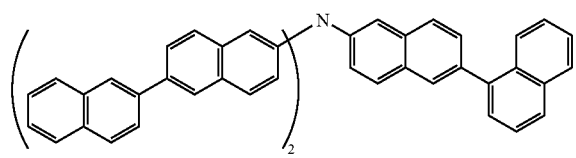

D-20
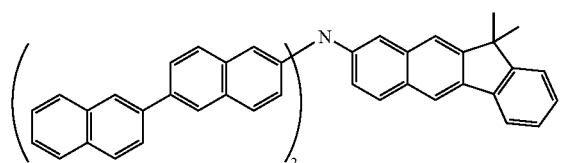

D-21
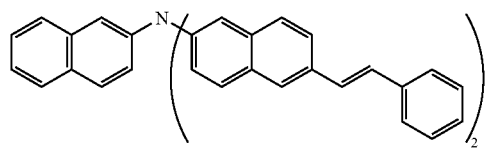

D-22
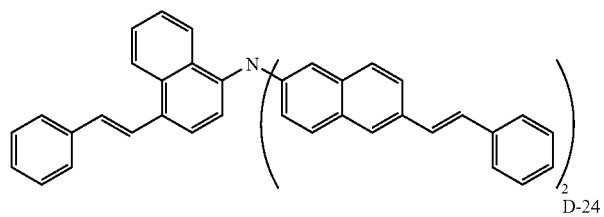

D-23
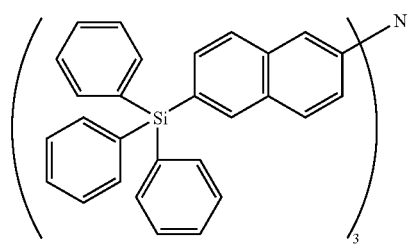

D-24
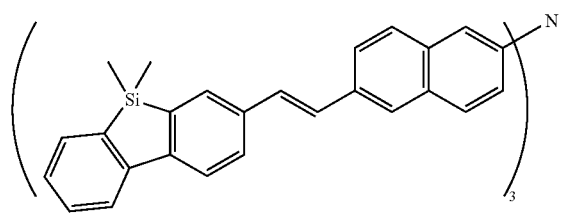

D-25
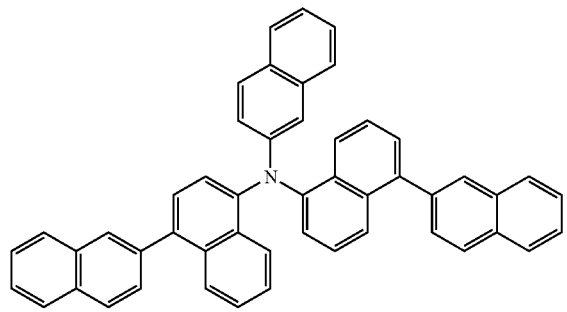

D-26
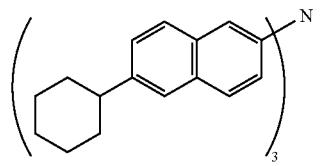

D-27
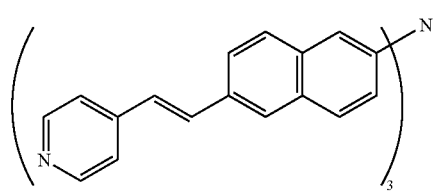

D-28

Next, an explanation about the manufacturing method of the trinaphthyl monoamine or a derivative thereof in the present invention will be described.

The manufacturing method of the trinaphthyl monoamine or the derivative thereof represented by the general formulae (I) to (III) in the present invention is not particularly limited, and it may be suitably produced in accordance with publicly known methods. For example, it can be produced in accordance with either a coupling reaction using a copper catalysis described in "Tetrahedron, 40 (1984) 1435-1456" with respect to a dinaphthylamine derivative and a brominated aromatic compounds, or a coupling reaction using a palladium catalyst described in "Journal of the American Chemical Society 123 (2001) 7727-7729" with respect to a dinaphthylamine derivative and a brominated aromatic compounds.

It is preferable for the trinaphthyl monoamine or the derivative thereof in the present invention to be used as a material for the organic EL device, more preferable to be used as a light emitting material for the organic EL device, and particularly, further preferable to be used as a doping material for the organic EL device.

The present invention provides an organic EL device which is composed of one or more organic compound layers including at least one light emitting layer sandwiched between a pair of electrodes, wherein at least one of the organic compound layers contains at least one kind of the trinaphthyl monoamine or the derivative thereof in the present invention.

In the organic EL device of the present invention, it is preferable that at least one kind of the trinaphthyl monoamine or the derivative thereof is contained, and that the light emitting layer preferably contains the trinaphthyl monoamine or the derivative thereof in an amount of 0.01 to 20% by weight, further preferably 0.5 to 20% by weight, particularly preferably 1 to 20% by weight, and the most preferably 5 to 20% by weight.

Further, in the case where the trinaphthyl monoamine or the derivative thereof in the present invention is employed as the light emitting material for the organic EL device, it is preferable that the light emitting layer contains at least one kind of the above trinaphthyl monoamine or the derivative thereof together with at least one kind selected from the compound represented by the following general formulae (2a) to (2d), and that at least one kind selected from the compound represented by the following general formulae (2a) to (2d) is a host material.

The general formulae (2a) to (2d) will be explained below.

General formula (2a):

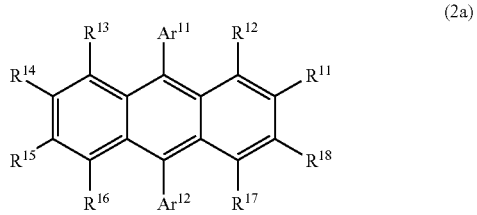

where: $Ar^{11}$ and $Ar^{12}$ each independently represents a group derived from a substituted or unsubstituted aromatic ring having 6 to 20 ring carbon atoms.

The aromatic ring may be substituted by 1 or more substituents.

The substituent of the aromatic ring is selected among a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group (having 6 to 50 carbon atoms in the aryl part, and having 1 to 5 carbon atoms in the alkyl part), a substituted or unsubstituted aryloxy group having 6 to 50 atoms forming a ring (ring atoms), a substituted or unsubstituted arylthio group having 6 to 50 carbon atoms, a substituted or unsubstituted alkoxycarbonyl group (having 1 to 50 carbon atoms in the alkoxy part), a substituted or unsubstituted silyl group, a carboxyl group, a halogen atom, a cyano group, a nitro group and a hydroxyl group; and is selected among a group to be described below as a specific example of $R^{11}$ to $R^{18}$.

When the aromatic ring is substituted by 2 or more substituents, the substituents may be identical to or different from each other and neighboring substituents may be bonded with each other to form a saturated or unsaturated cyclic structure.

$R^{11}$ to $R^{18}$ each independently represents one member selected from a hydrogen atom, a substituted or unsubstituted aryl group having 6 to 50 ring carbon atoms, a substituted or unsubstituted heteroaryl group having 4 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms (having 6 to 50 carbon atoms in the aryl part, and having 1 to 5 carbon atoms in the alkyl part), a substituted or unsubstituted aryloxy group having 5 to 50 ring atoms, a substituted or unsubstituted arylthio group having 5 to 50 ring atoms, a substituted or unsubstituted alkoxycarbonyl group having 2 to 50 carbon atoms (having 1 to 50 carbon atoms in the alkoxy part), a substituted or unsubstituted silyl group, a carboxyl group, a halogen atom, a cyano group, a nitro group and a hydroxyl group.

In the general formula (2a), it is preferable that $Ar^{11}$ and $A^{12}$ are the groups which are different from each other.

It is preferable that in the above general formula (2a), at least one of $Ar^{11}$ and $A^{12}$ corresponds to a substituent with substituted or unsubstituted aromatic fused ring groups having 10 to 30 ring atoms.

It is preferable that the substituted or unsubstituted fused ring group having 10 to 30 ring atoms corresponds to a substituted or unsubstituted naphthalene ring.

Examples of the group derived from the substituted or unsubstituted aromatic ring having 6 to 20 ring carbon atoms represented by $Ar^{11}$ and $Ar^{12}$ in the general formula 2(a) include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, etc.

Preferable examples are the groups derived from the substituted or unsubstituted aromatic ring having 10 to 14 ring carbon atoms and in particular, 1-naphthyl group, 2-naphthyl group and 9-phenanthryl group.

Examples of the substituted or unsubstituted aryl group having 6 to 50 ring carbon atoms represented by $R^{11}$ to $R^{18}$ in the general formula (2a) include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, etc.

Examples of the substituted or unsubstituted heteroaryl group having 4 to 50 ring atoms represented by $R^{11}$ to $R^{18}$ in the general formula 2(a) include 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1 indolyl group, 2-methyl-3-indolyl group, 4-methyl-3-indolyl group, 2-t-butyl-1-indolyl group, 4-t-butyl 1-indolyl group, 2-t-butyl 3-indolyl group, 4-t-butyl 3-indolyl group, etc.

Examples of the substituted or unsubstituted alkyl group having 1 to 50 carbon atoms represented by $R^{11}$ to $R^{18}$ in the general formula 2(a) and the substituent for the above aromatic ring include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitro isobutyl group, 1,2-dinitro ethyl group, 1,3-dinitroisopropyl group, 2,3-dinitro-t-butyl group, 1,2,3-trinitropropyl group, etc.

Examples of the substituted or unsubstituted cycloalkyl group having 3 to 50 carbon atoms represented by $R^{11}$ to $R^{18}$ in the general formula (2a) and the substituent for the above aromatic ring include cyclopropyl group, cyclobutyl group, cyclopentyl group, cyclohexyl group, 4-methylcyclohexyl group, 1-adamantyl group, 2-adamantyl group, 1-norbornyl group, 2-norbornyl group, etc.

Examples of the substituted or unsubstituted alkoxy group having 1 to 50 carbon atoms represented by $R^{11}$ to $R^{18}$ in the general formula (2a) and the substituent for the above aromatic ring is a group expressed by —OY and examples of Y are the same as described about the foregoing substituted or unsubstituted alkyl group having 1 to 50 carbon atoms represented by $R^{11}$ to $R^{18}$ and as the substituent for the above aromatic ring.

Examples of the substituted or unsubstituted aralkyl group (having 6 to 50 carbon atoms in the aryl part, and having 1 to 50 carbon atoms in the alkyl part) represented by $R^{11}$ to $R^{18}$ and the substituent for the above aromatic ring include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, 6-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group, etc.

The substituted or unsubstituted aryloxy group having 6 to 50 ring atoms and the substituted or unsubstituted arylthio group having 6 to 50 ring atoms both represented by $R^{11}$ to $R^{18}$ in the general formula (2a) and the substituent for the above aromatic ring is a group expressed by —OY' and SY" respectively and examples of Y' and Y" are the same as described about the foregoing substituted or unsubstituted aryl group having 6 to 50 ring atoms represented by $R_1$ to $R_8$ and as the substituent for the above aromatic ring.

The substituted or unsubstituted alkoxycarbonyl group having 2 to 50 carbon atoms represented by $R^{11}$ to $R^{18}$ in the general formula (2a) and the substituent for the above aromatic ring is a group expressed by —COOZ and examples of Z are the same as described about the foregoing substituted or unsubstituted alkyl group having 1 to 50 carbon atoms represented by $R^{11}$ to $R^{18}$ and as the substituent for the above aromatic groups.

Examples of the silyl group represented by $R^{11}$ to $R^{18}$ in the general formula (2a) and the substituent for the above aromatic ring include trimethylsilyl group, triethylsilyl group, t-butyldimethylsilyl group, vinyldimethylsilyl group, propyldimethylsilyl group, triphenylsilyl group, etc.

Examples of the halogen atom represented by $R^{11}$ to $R^{18}$ in the general formula (2a) and the substituent for the above aromatic ring include fluorine atom, chlorine atom, bromine atom, iodine atom, etc.

Examples of the aromatic ring represented by $R^{11}$ to $R^{18}$ and $Ar^{11}$ to $Ar^{12}$ include halogen atoms, hydroxyl groups, amino groups, nitro groups, cyano groups, alkyl groups, aryl groups, cycloalkyl groups, alkoxy groups, aromatic heterocyclic groups, aralkyl groups, aryloxy groups, arylthio groups, alkoxycarbonyl groups and carboxyl groups, etc.

It is preferable that the anthracene derivative represented by the general formula (2a) corresponds to a compound having a structure shown by the following general formula (2a'):

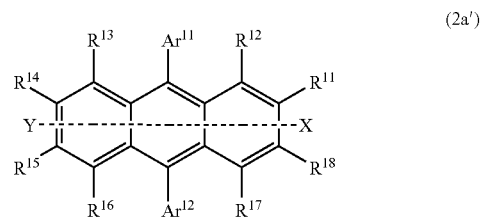

(2a')

where: $Ar^{11}$, $Ar^{12}$, and $R^{11}$ to $R^{18}$ each independently is the same as in the general formula (2a), and the specific examples include the same as those described above;
with the proviso that, in the general formula (2a'), the groups to be bonded to 9- and 10-positions of the central anthracene are not symmetrical with respect to the X-Y axis.

Specific examples of the anthracene derivative represented by the general formula (2a) employed for the organic EL device of the present invention include various kinds of publicly known anthracene derivative such as the anthracene derivative having two anthracene skeletons in its molecule which is disclosed in columns [0043] to [0063] of JP 2004-356033A, the compound having a single anthracene skeleton in itself which is disclosed on pages 27 and 28 of the International PCT publication WO 2005/061656 pamphlet, etc. Typical examples are shown below.

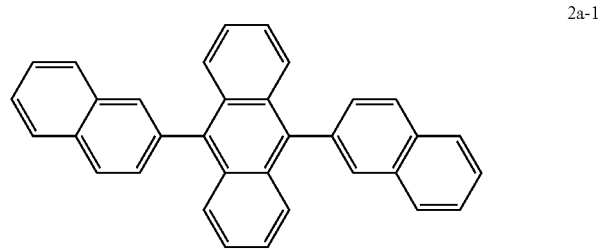

2a-1

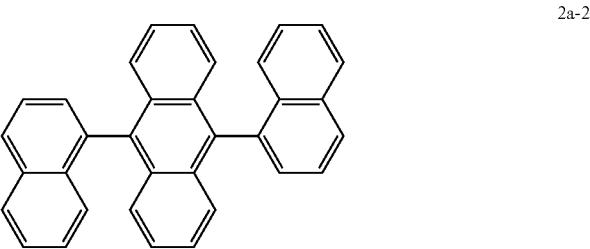

2a-2

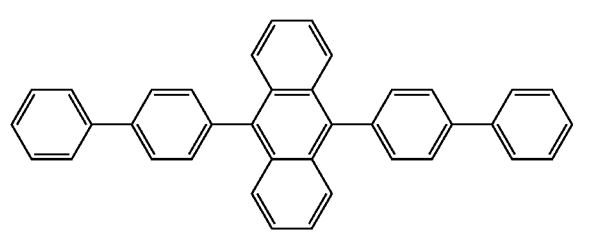

2a-3

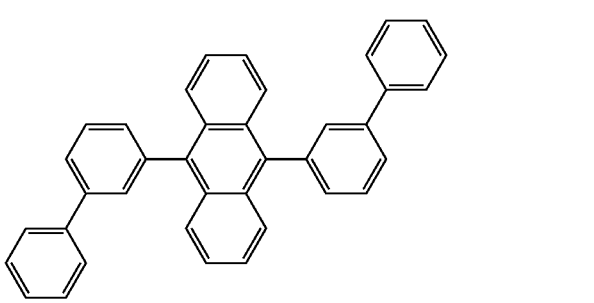

2a-4

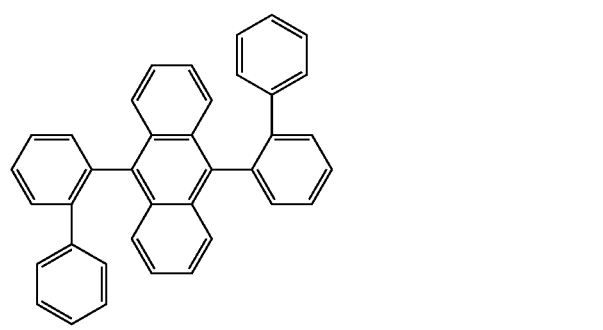

2a-5

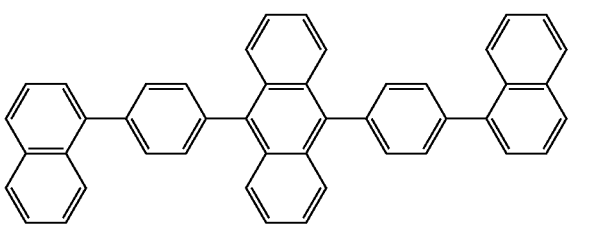

2a-6

-continued
2a-7
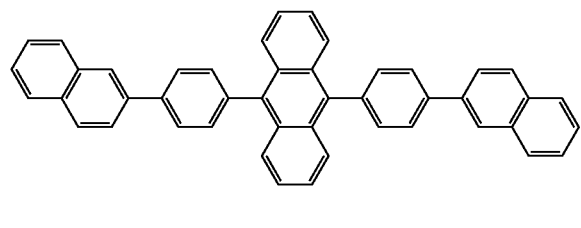
2a-8
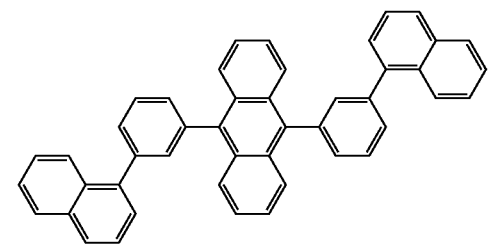
2a-9
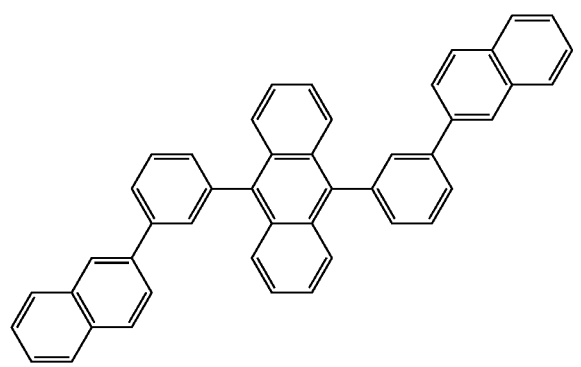
2a-10
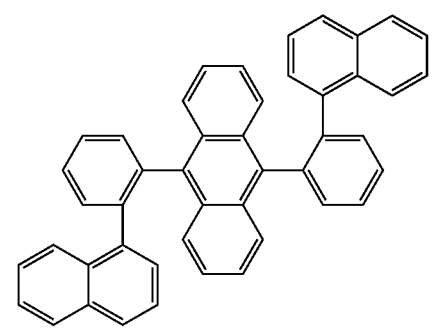
2a-11
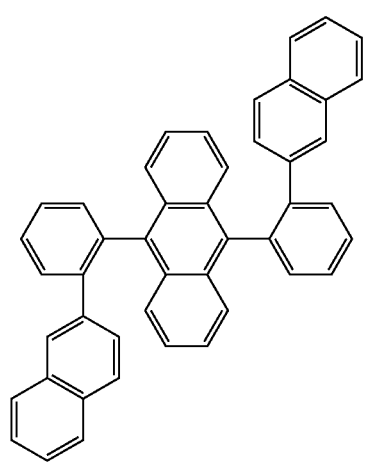
2a-12
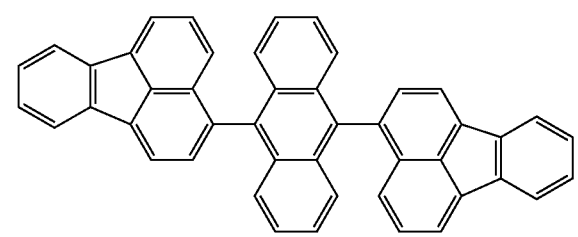
2a-13
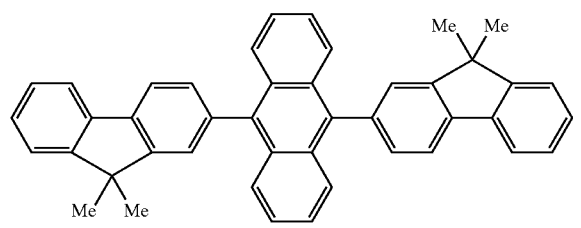
2a-14
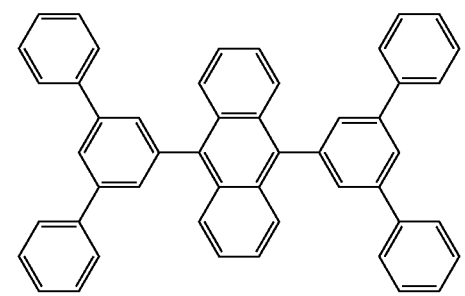

-continued
2a-15
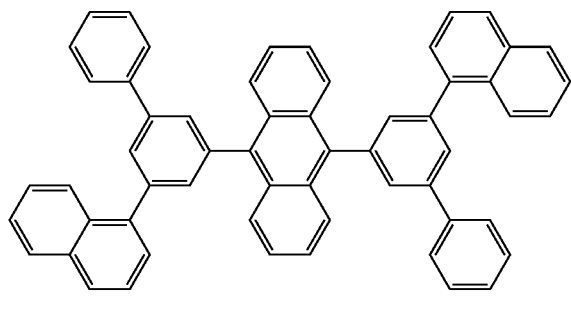
2a-16
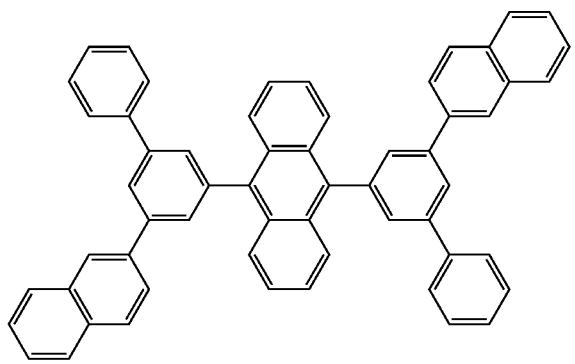
2a-17
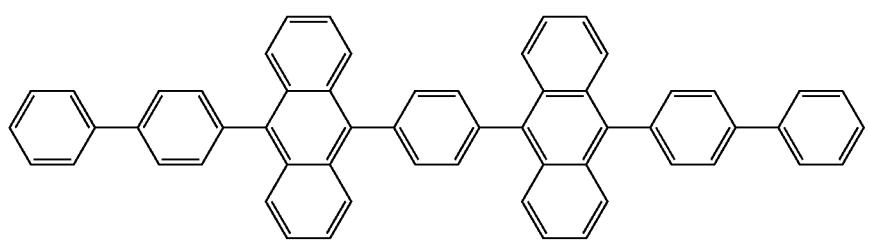
2a-18
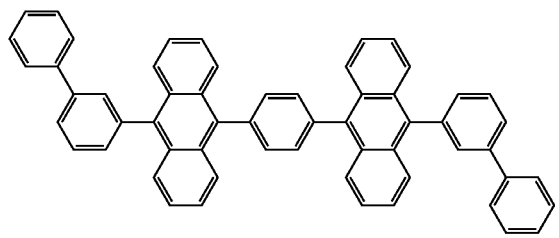
2a-19
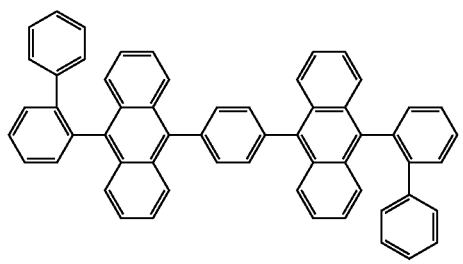
2a-20
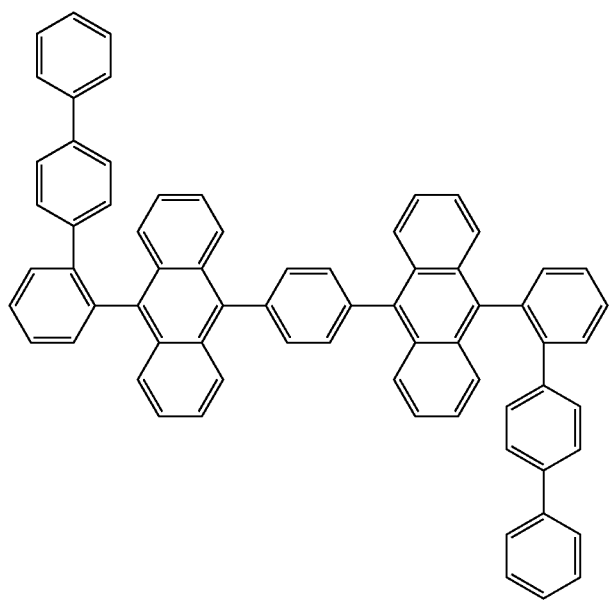

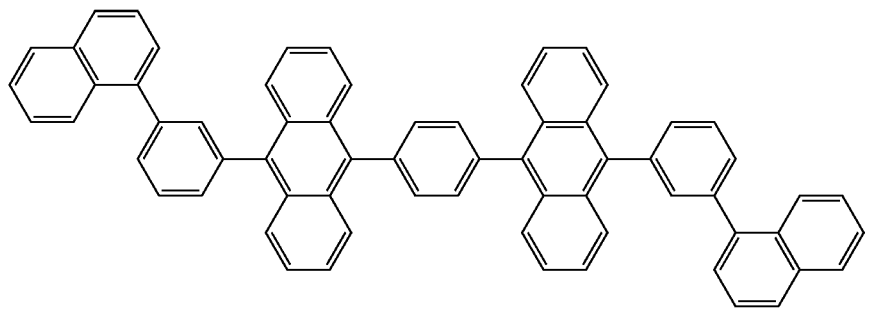

-continued
2a-27
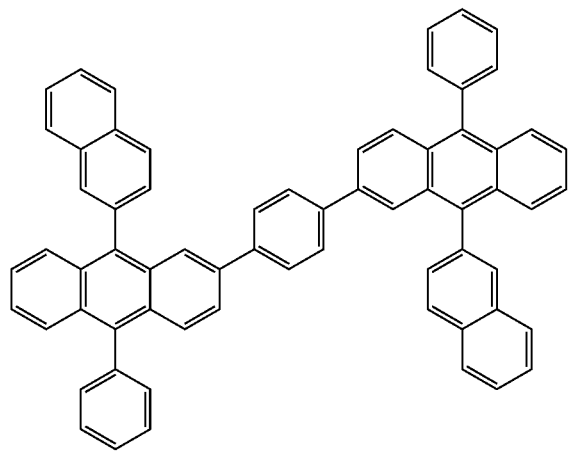
2a-28
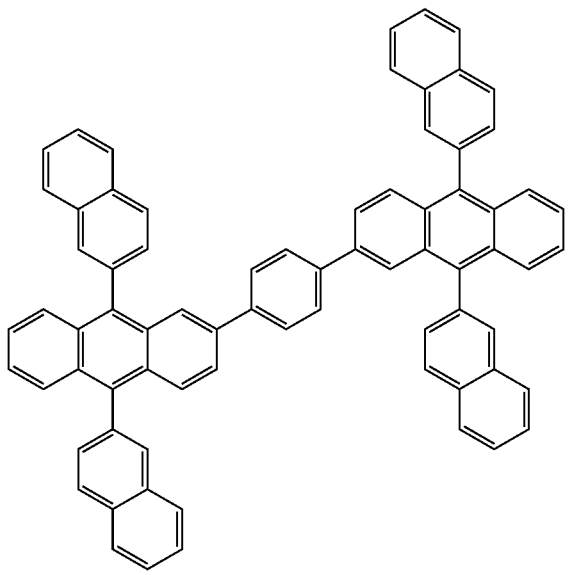
2a-29
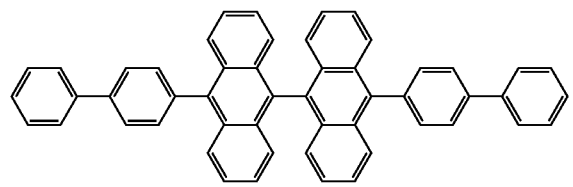
2a-30
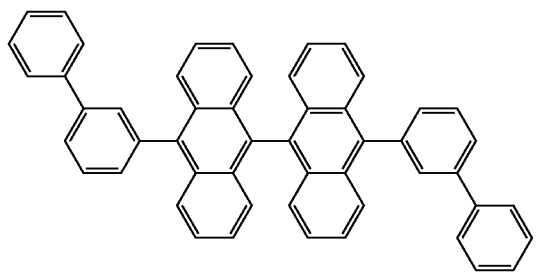
2a-31
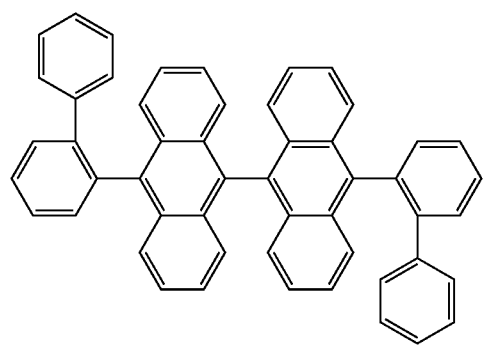
2a-32
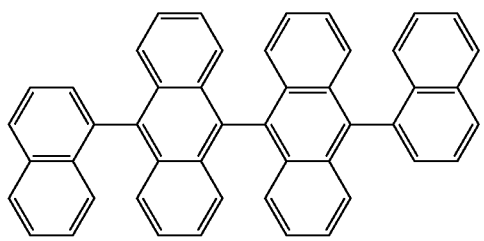

-continued
2a-33
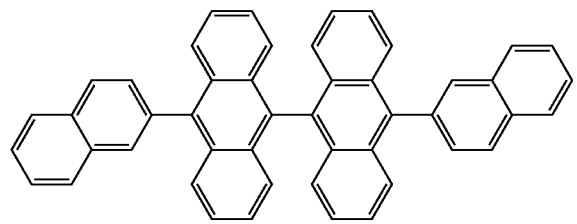
2a-34
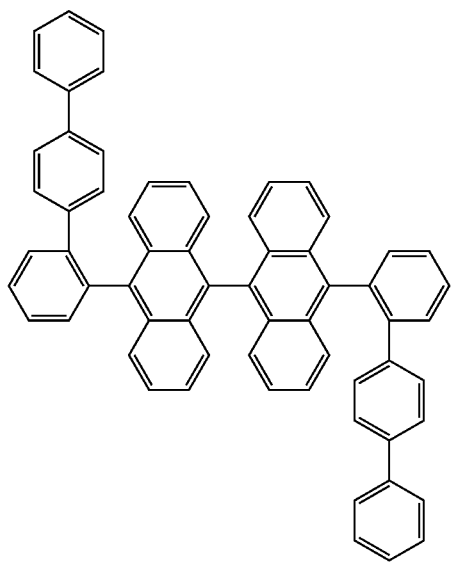
2a-35
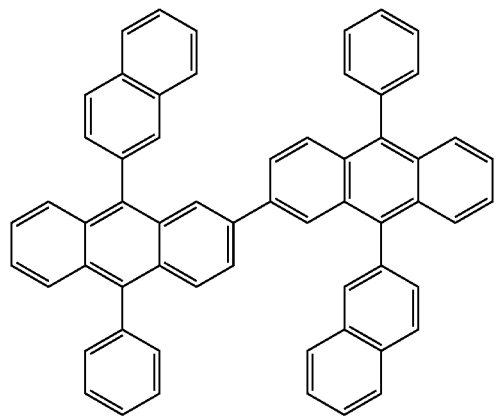
2a-36
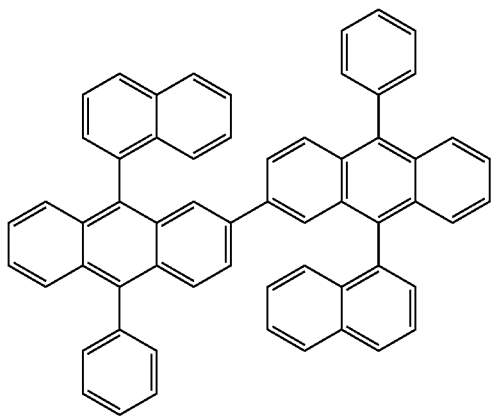
2a-37
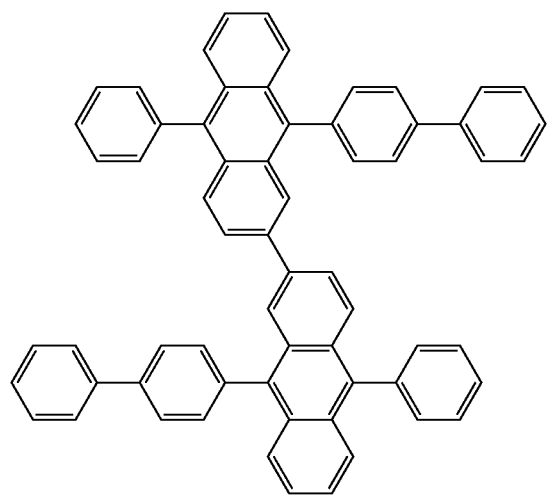
2a-38
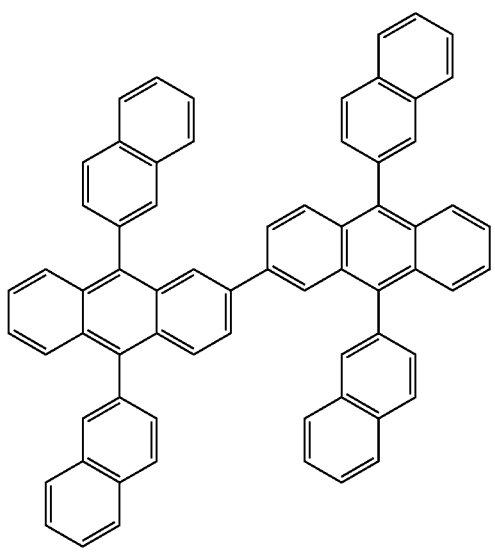

-continued
2a-39
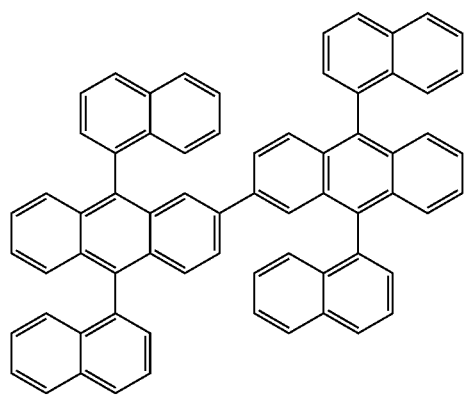
2a-40
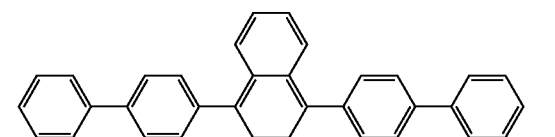
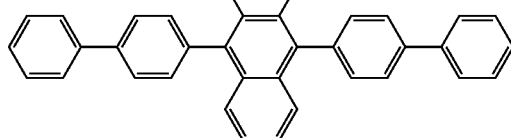
2a-41
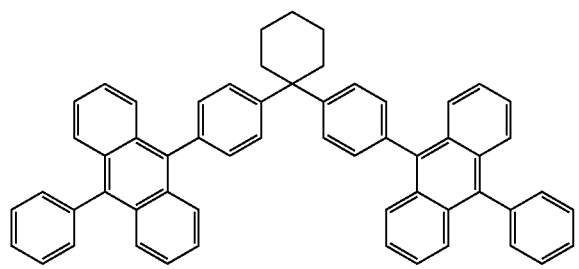
2a-42
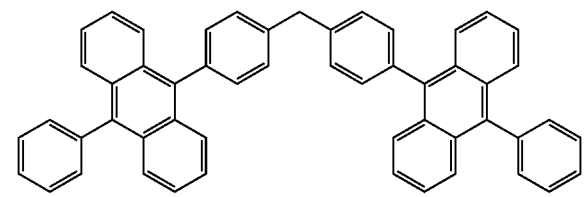
2a-43
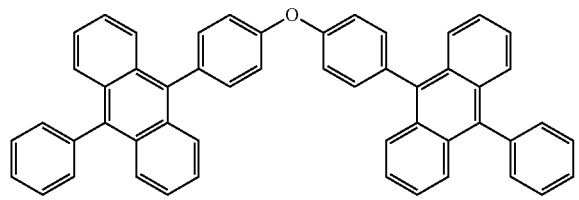
2a-44
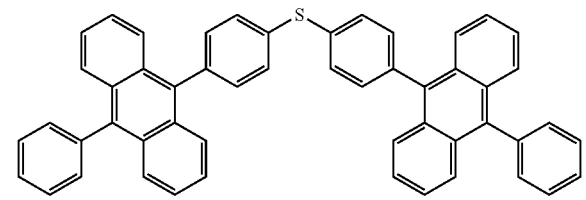
2a-45
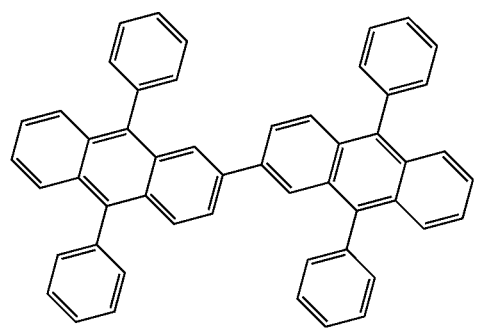
2a-46
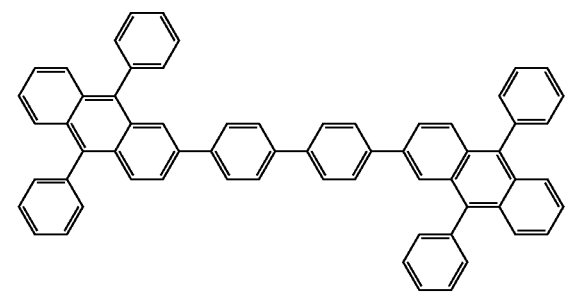
2a-47
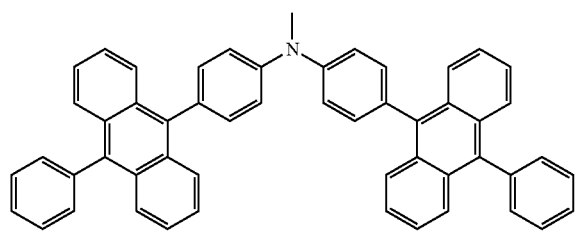
2a-48
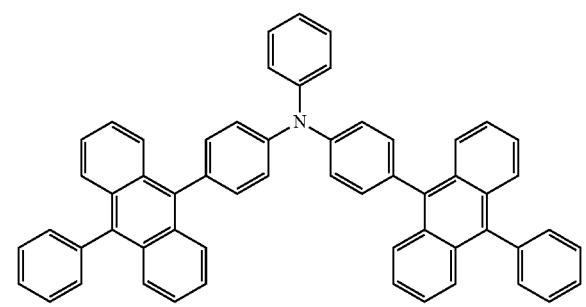

-continued
2a-49
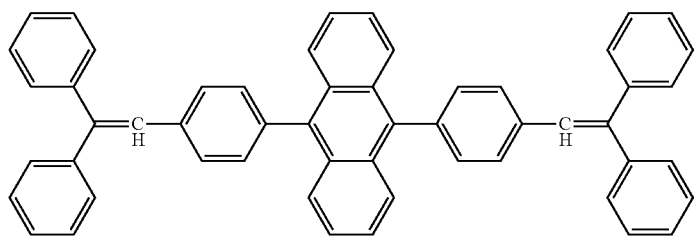
2a-50
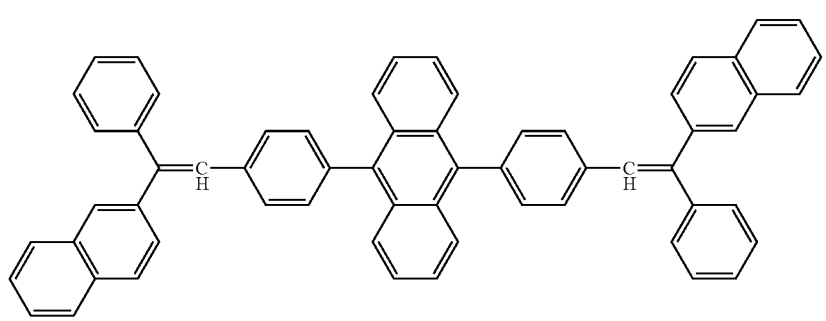
2a-51
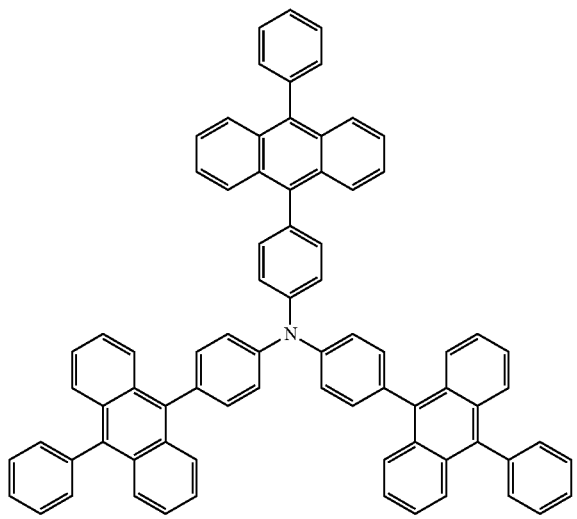
2a'-52
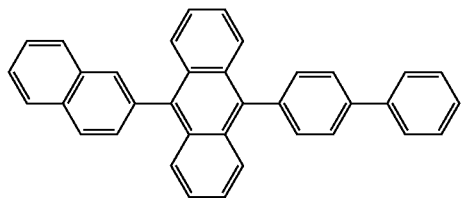
2a'-53
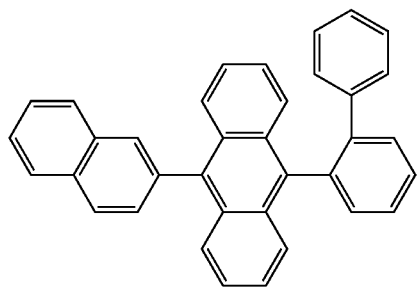
2a'-54
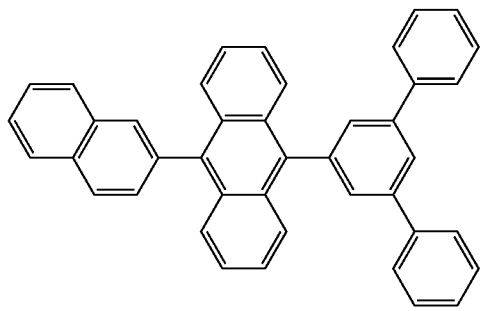

-continued
2a'-55
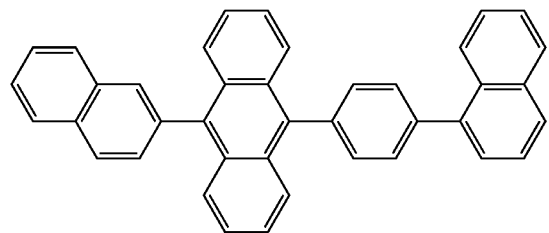
2a'-56
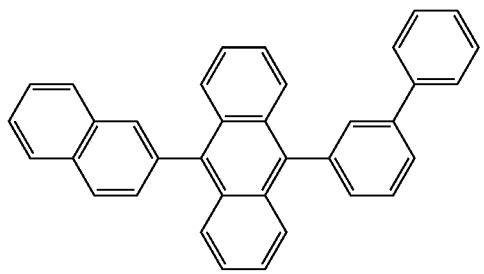
2a'-57
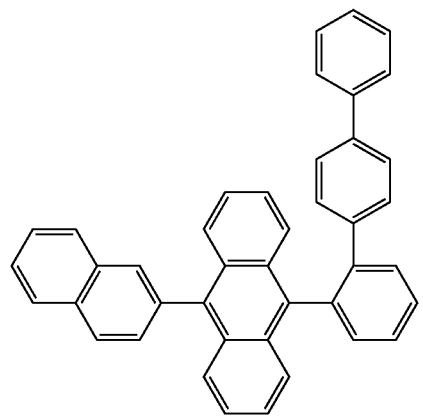
2a'-58
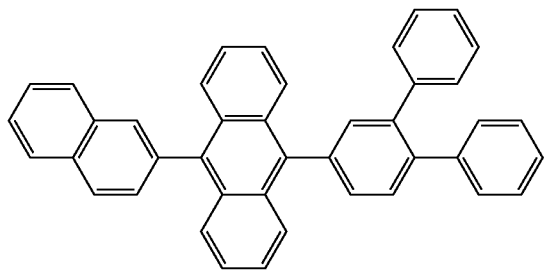
2a'-59
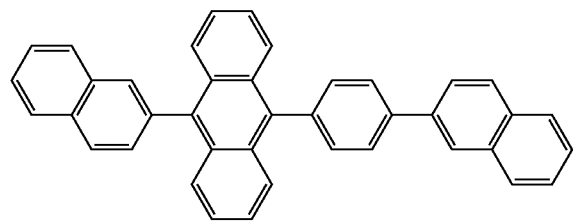
2a'-60
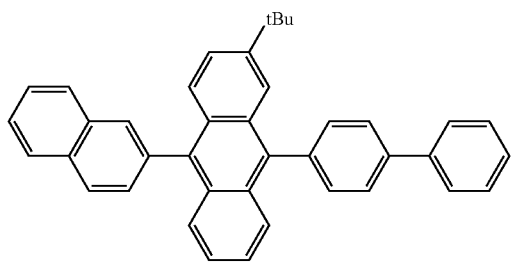
2a'-61
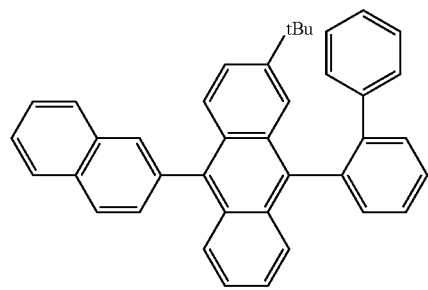
2a'-62
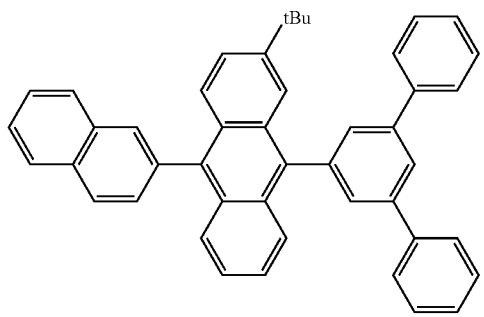

-continued
2a'-63
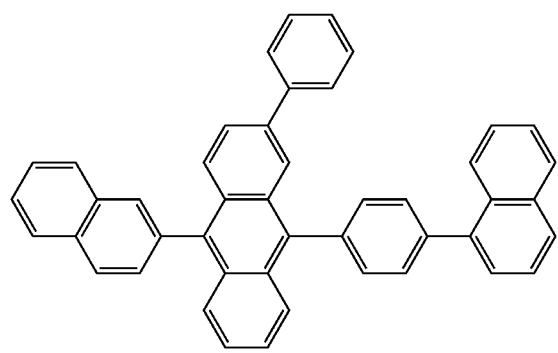
2a'-64
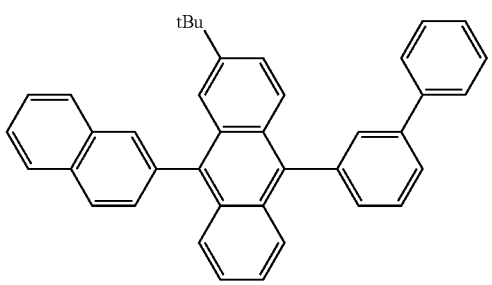
2a'-65
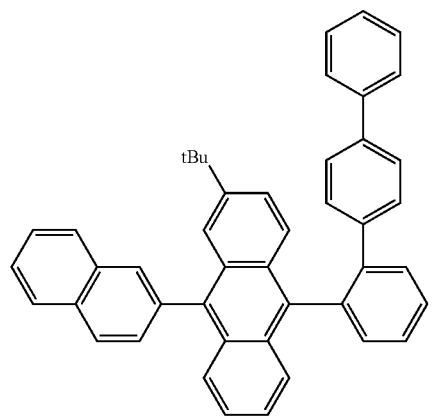
2a'-66
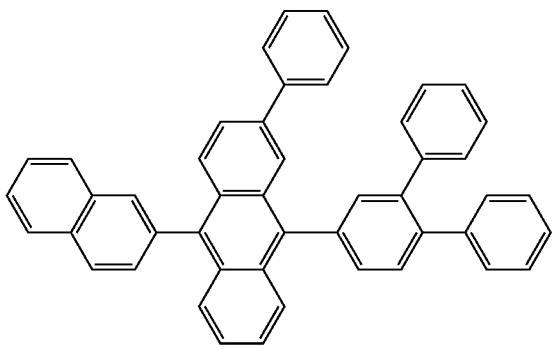
2a'-67
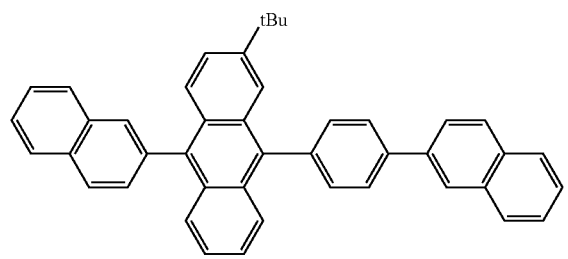
2a'-68
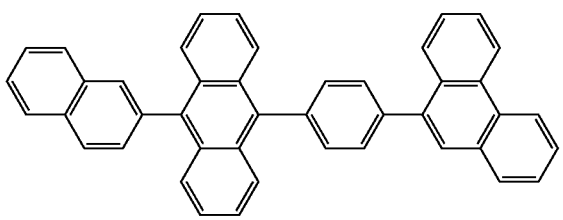
2a'-69
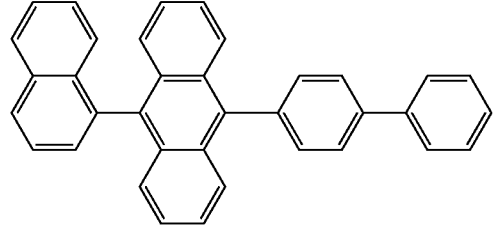
2a'-70
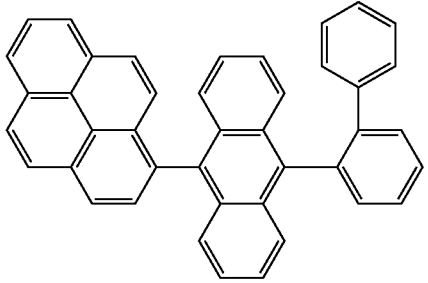

-continued
2a'-71
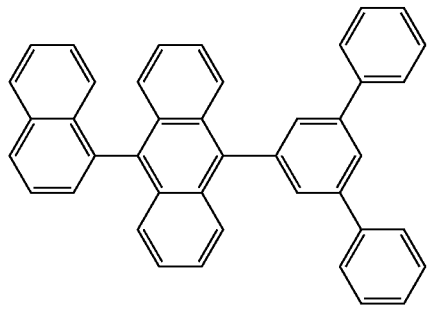
2a'-72
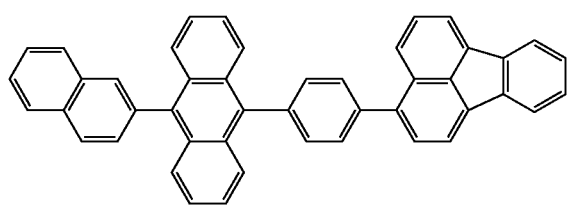
2a'-73
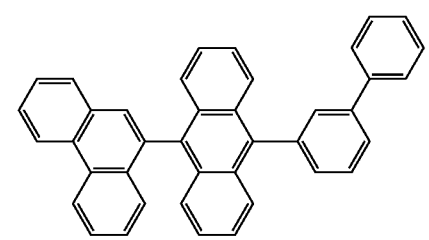
2a'-74
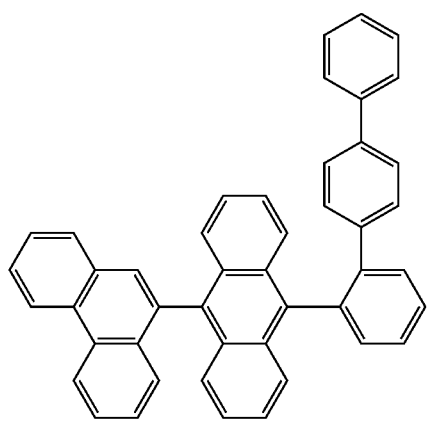
2a'-75
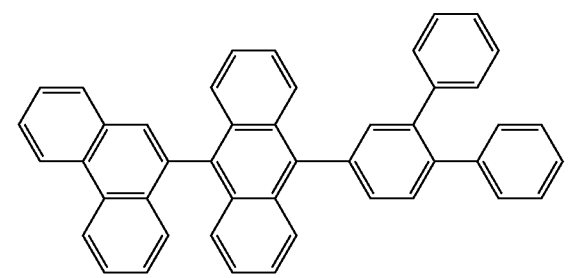
2a'-76
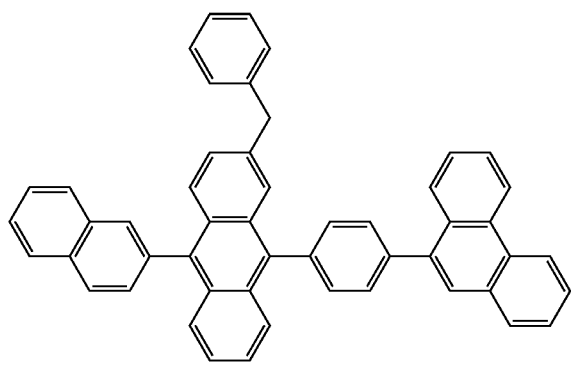
2a'-77
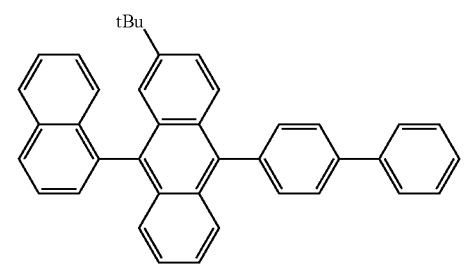

-continued
2a'-78
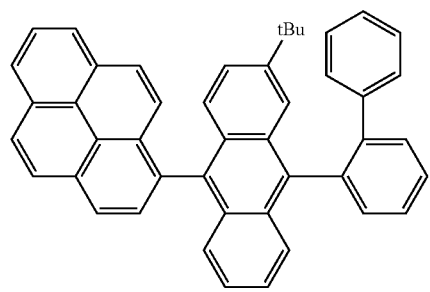
2a'-79
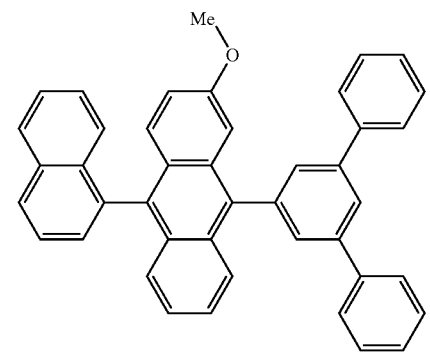
2a'-80
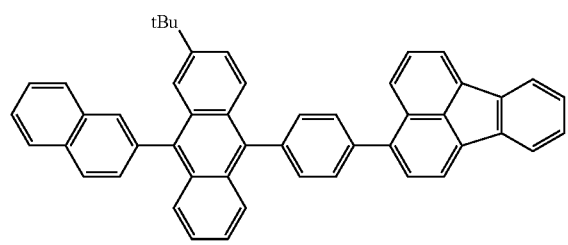
2a'-81
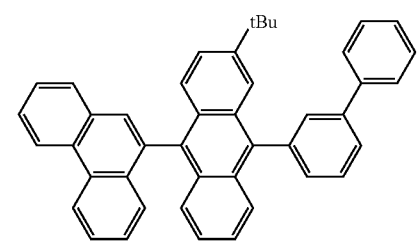
2a'-82
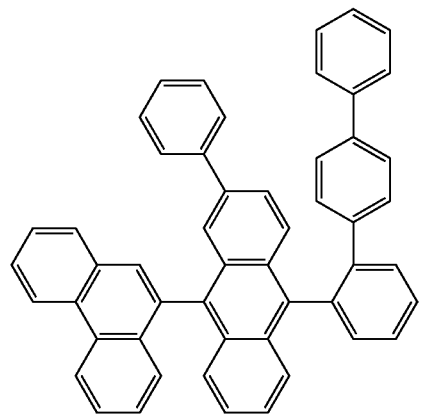
2a'-83
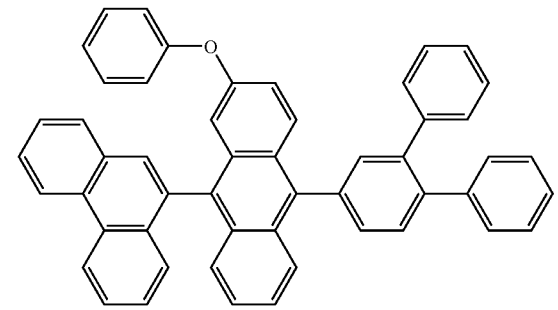
2a'-84
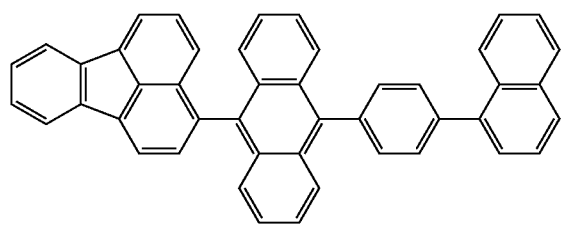
2a'-85
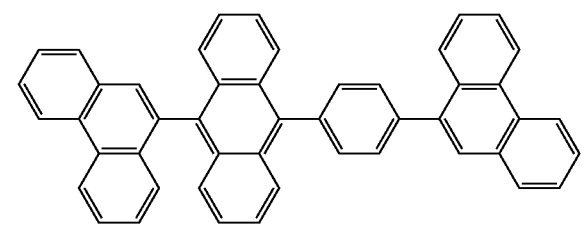

-continued
2a'-86
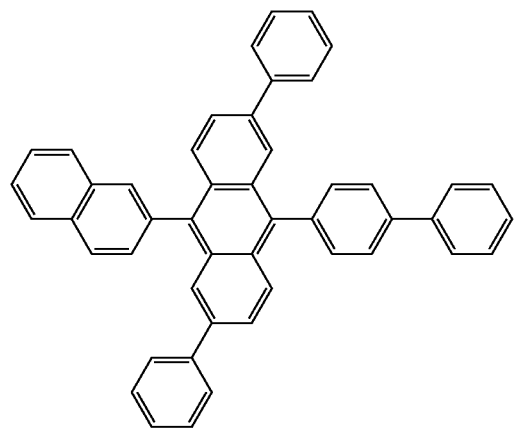
2a'-87
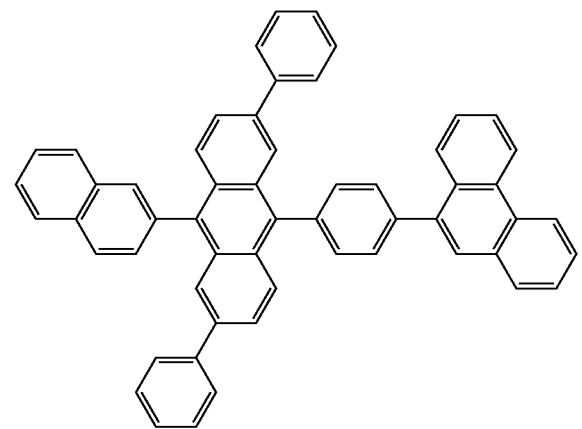
2a'-88
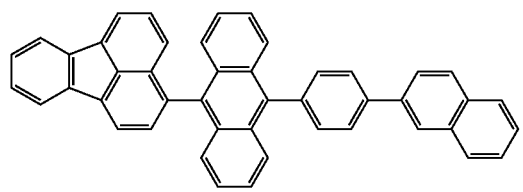
2a'-89
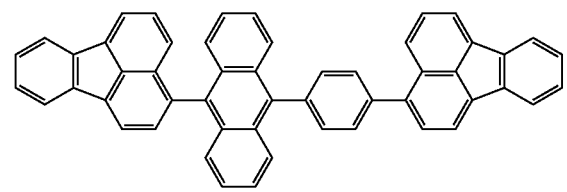
2a'-90
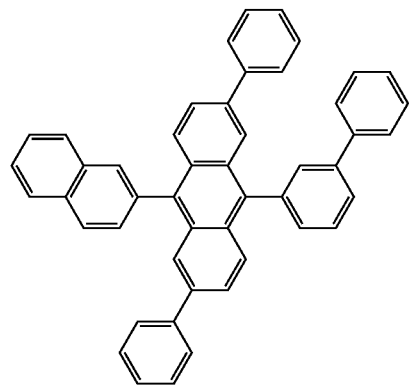
2a'-91
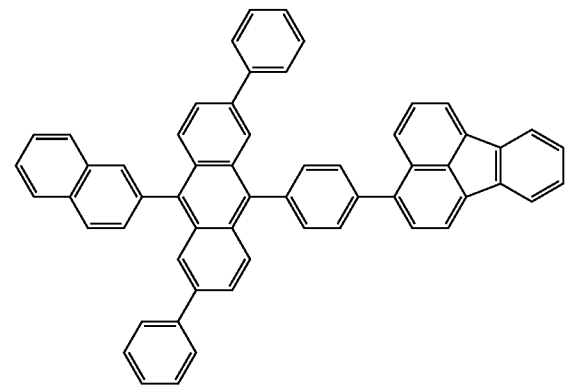
2a'-92
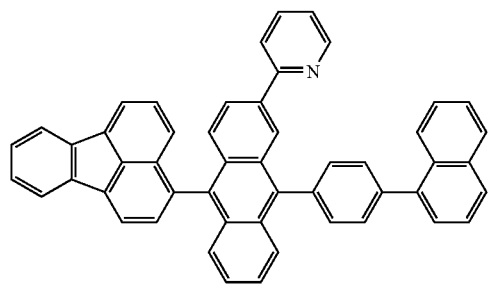
2a'-93
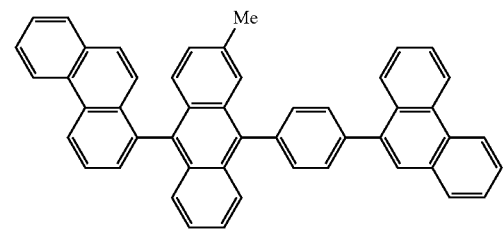

-continued
2a′-94
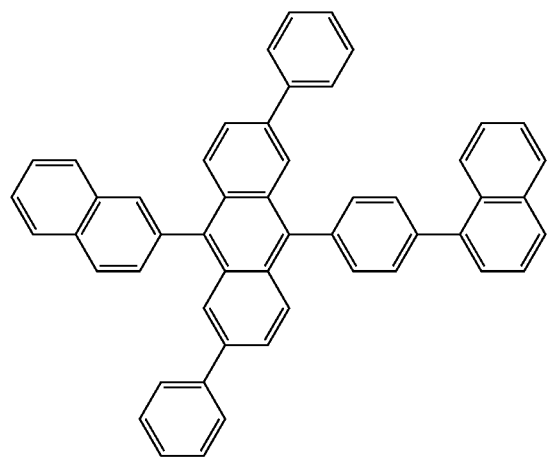
2a′-95
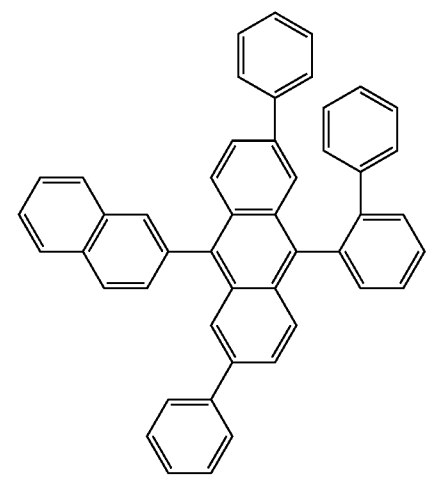
2a′-96
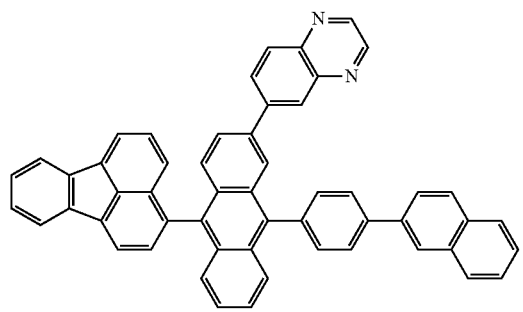
2a′-97
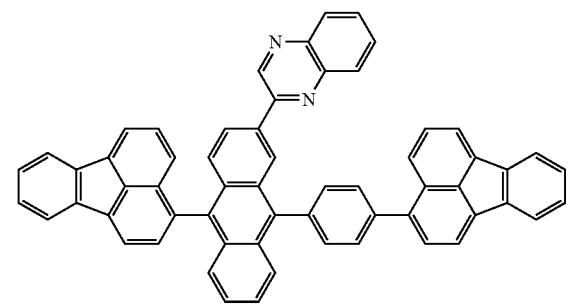
2a′-98
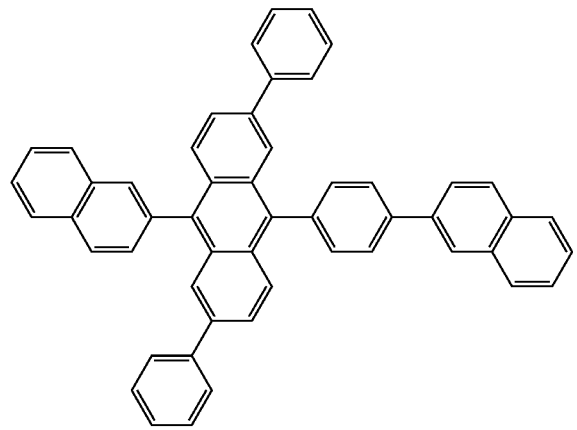
2a′-99
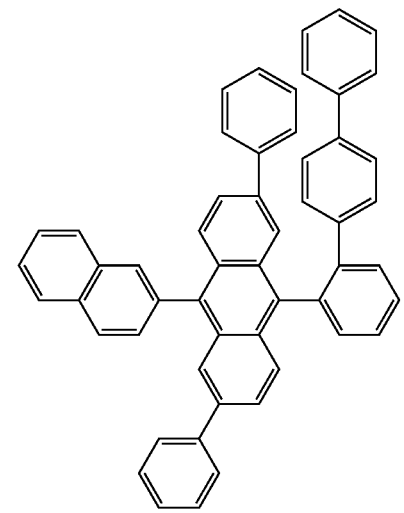
2a′-100
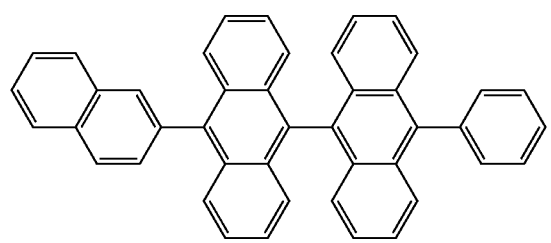
2a′-101
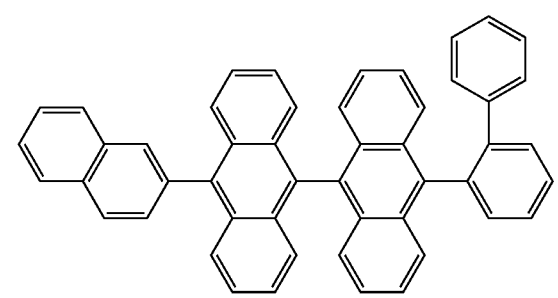

-continued
2a'-102
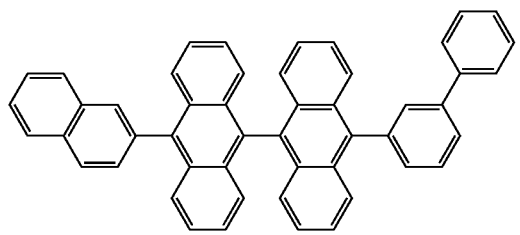
2a'-103
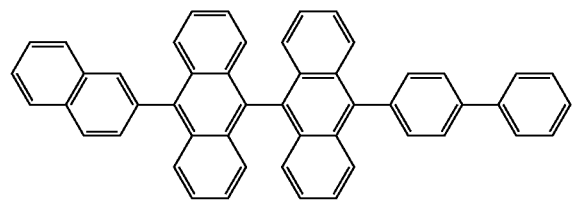
2a'-104
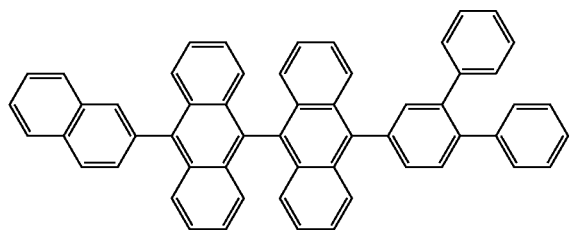
2a'-105
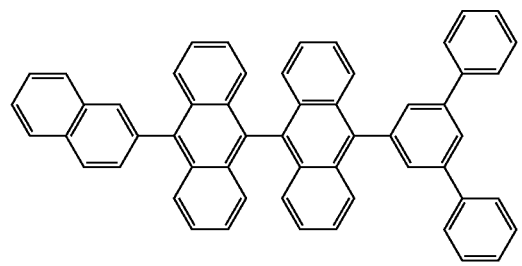
2a'-106
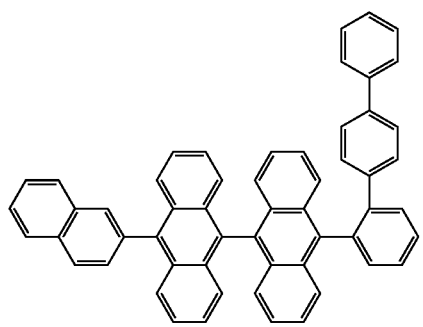
2a'-107
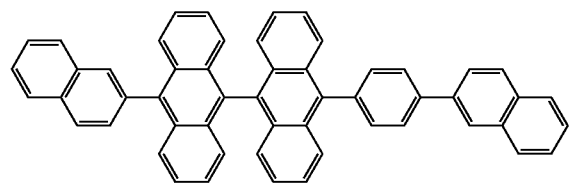
2a'-108
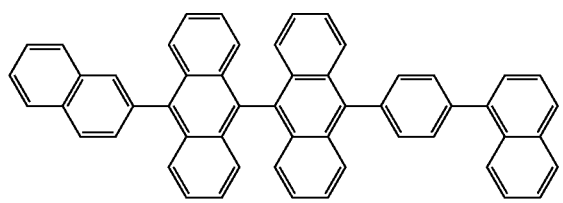
2a'-109
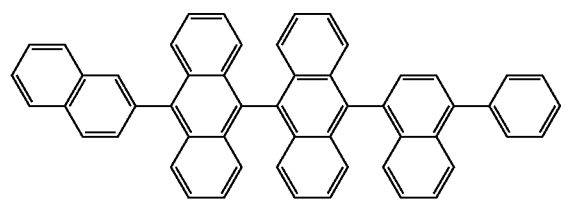
2a'-110
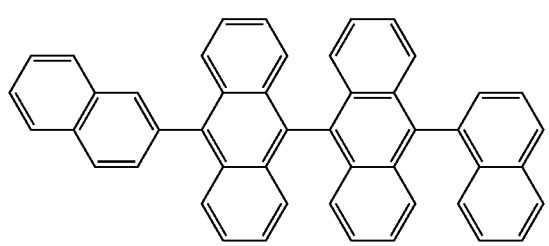
2a'-111
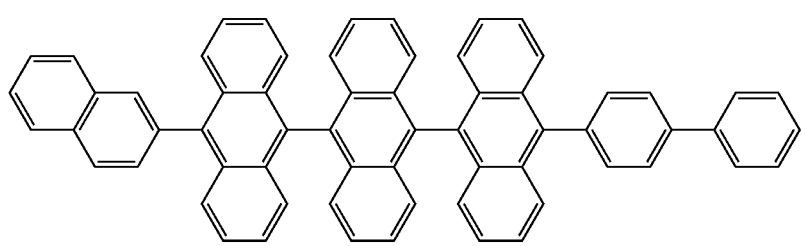

-continued
2a'-112
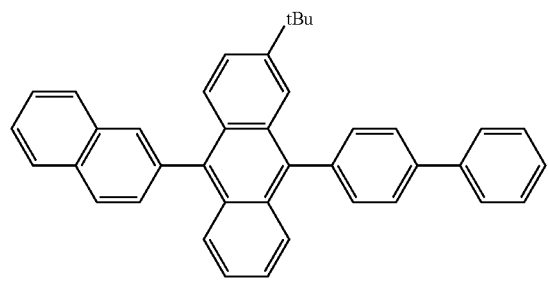
2a'-113
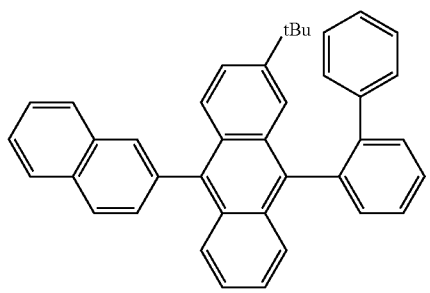
2a'-114
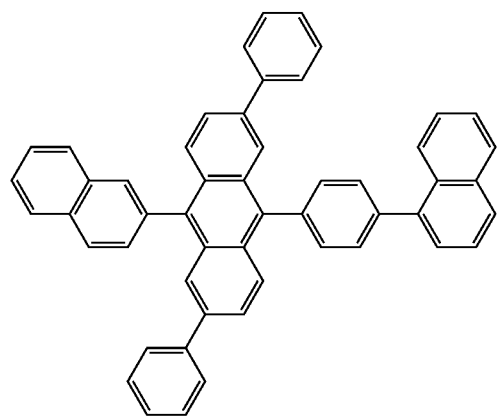
2a'-115
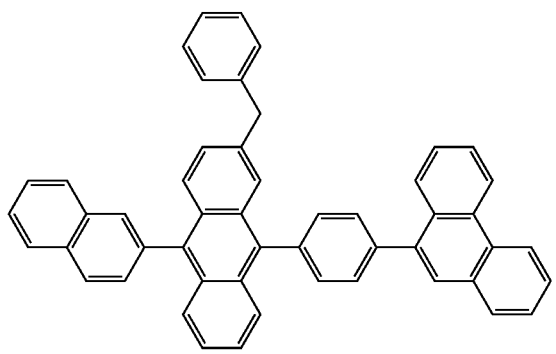
2a'-116
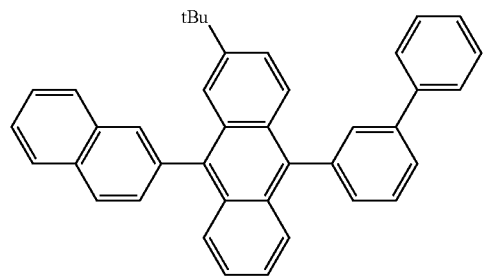
2a'-117
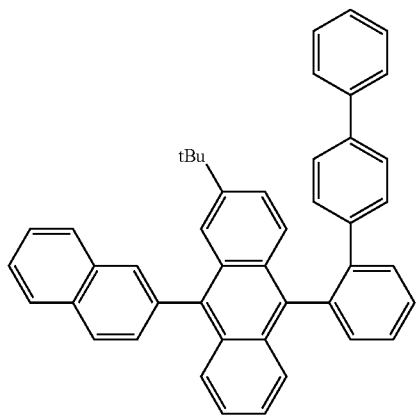
2a'-118
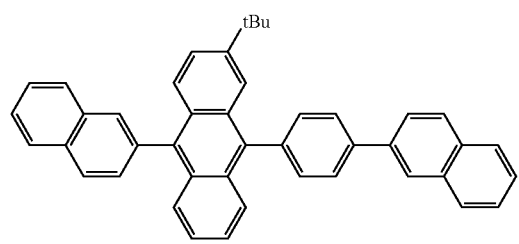
2a'-119
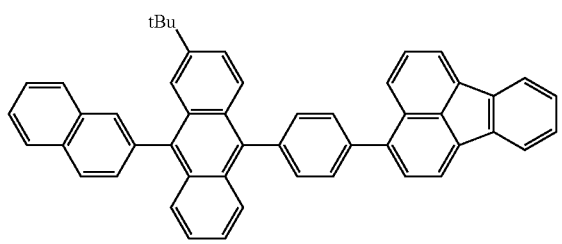

-continued
2a'-120
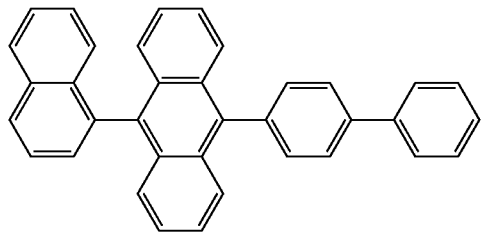
2a'-121
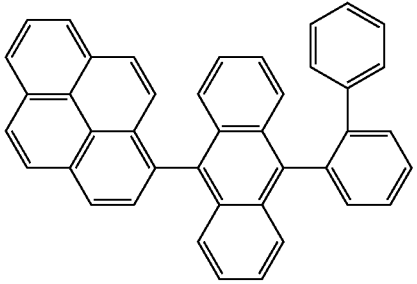
2a'-122
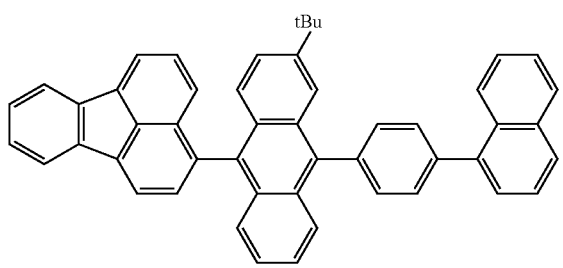
2a'-123
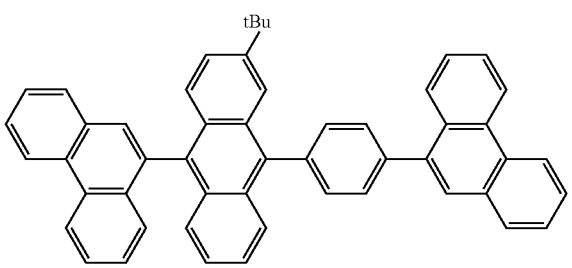
2a'-124
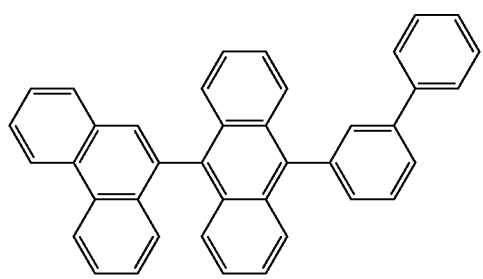
2a'-125
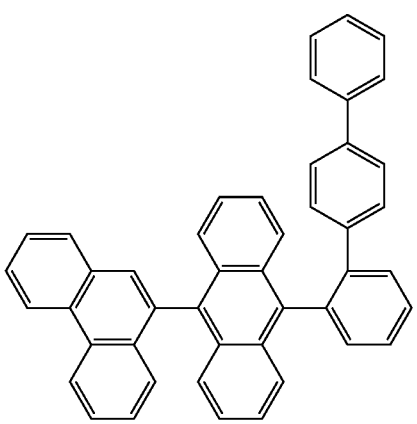
2a'-126
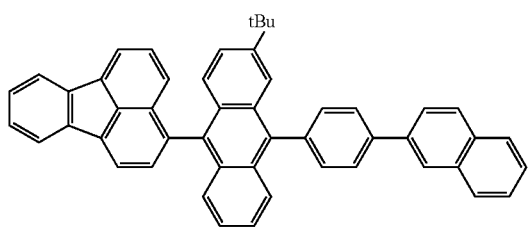
2a'-127
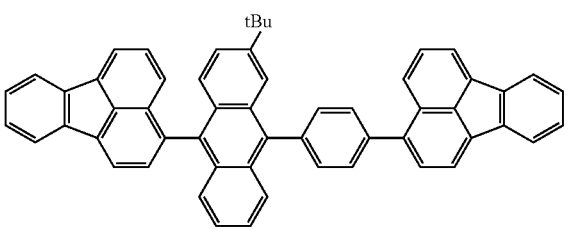
2a'-128
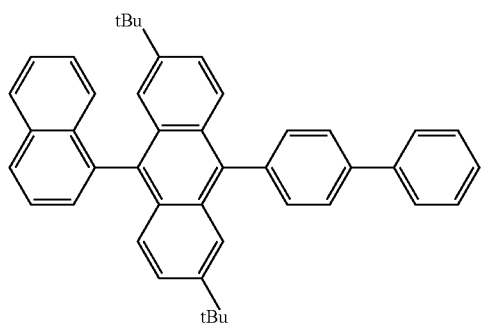
2a'-129
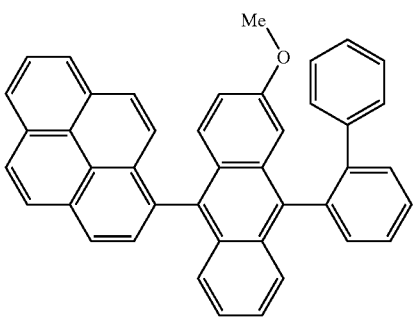

-continued
2a'-130
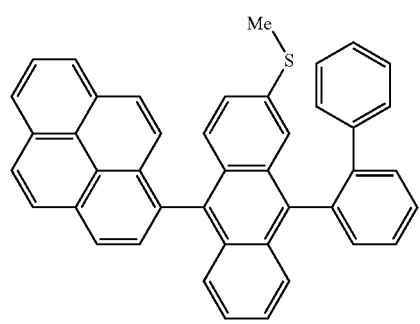
2a'-131
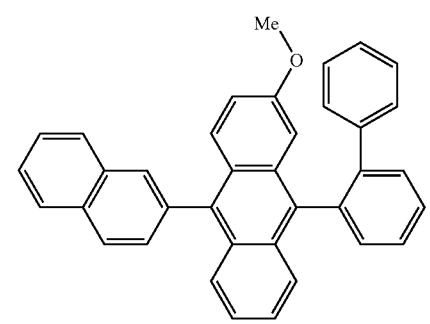
2a'-132
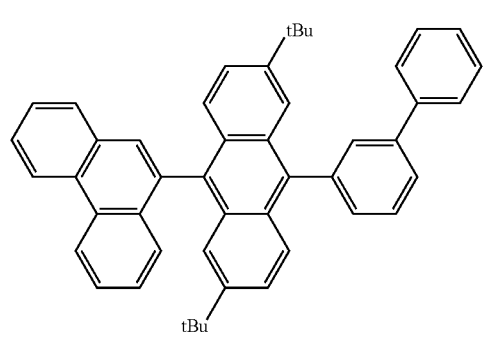
2a'-133
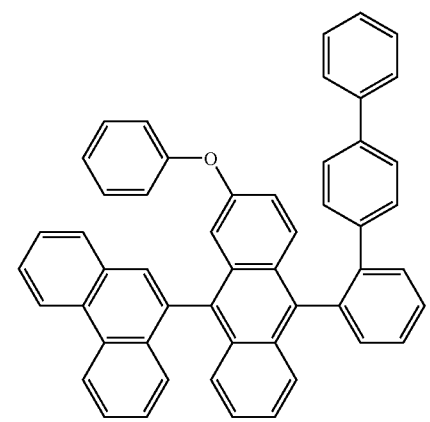
2a'-134
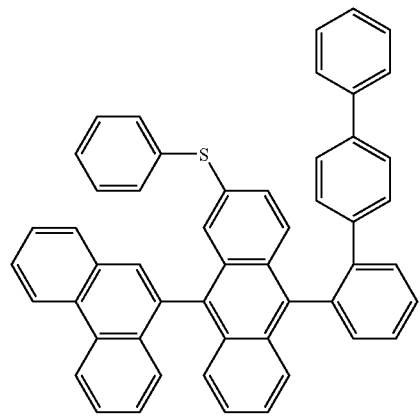
2a'-135
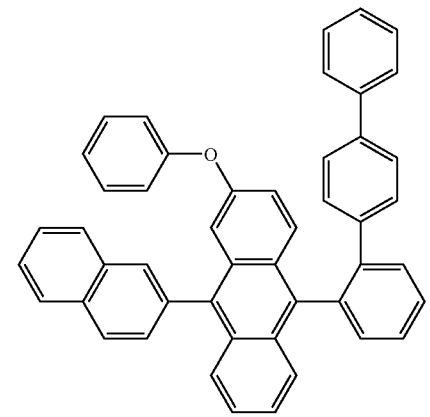
2a'-136
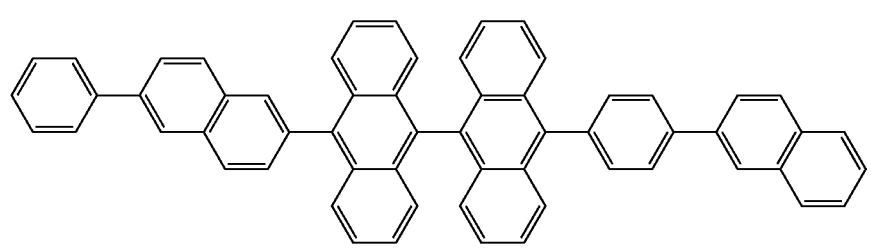
2a'-137
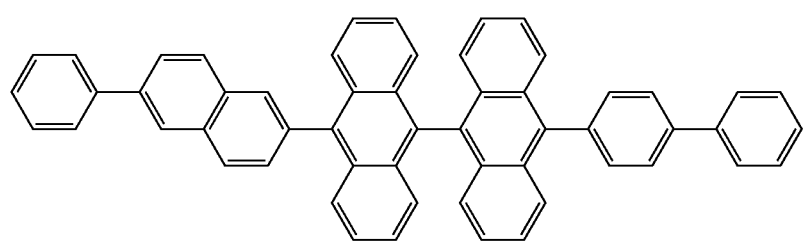

-continued
2a′-138
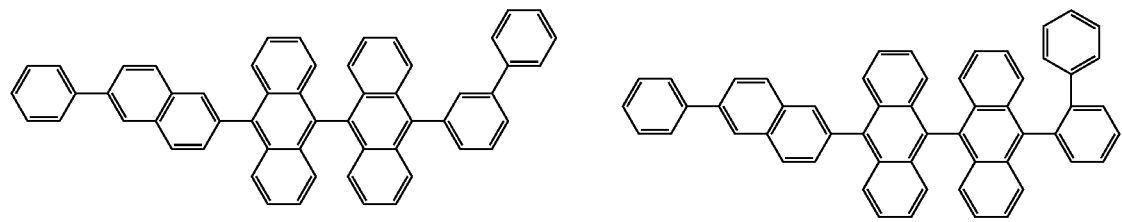
2a′-139
2a′-140
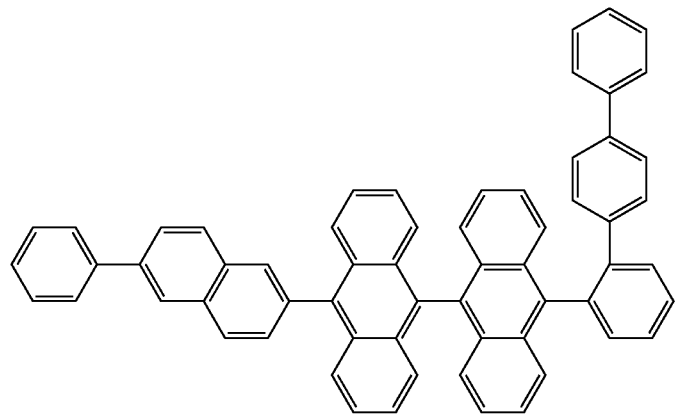
2a′-141
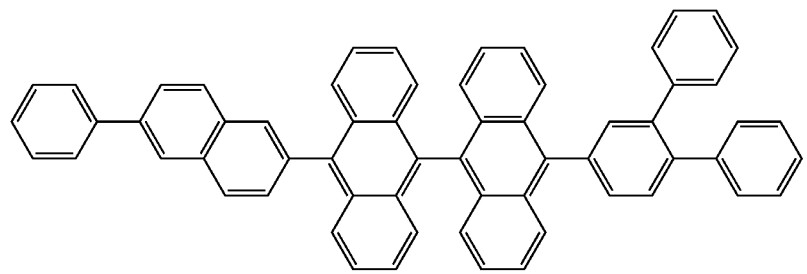
2a′-142
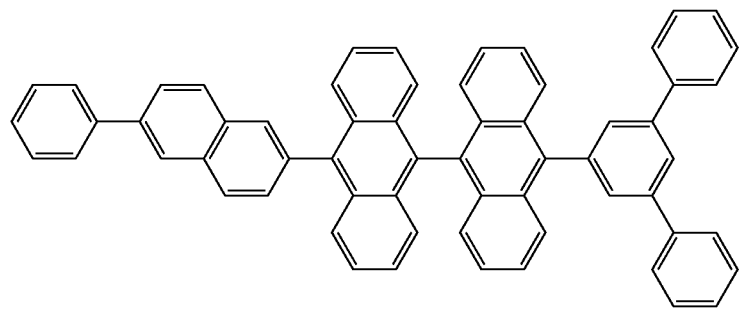
2a′-143
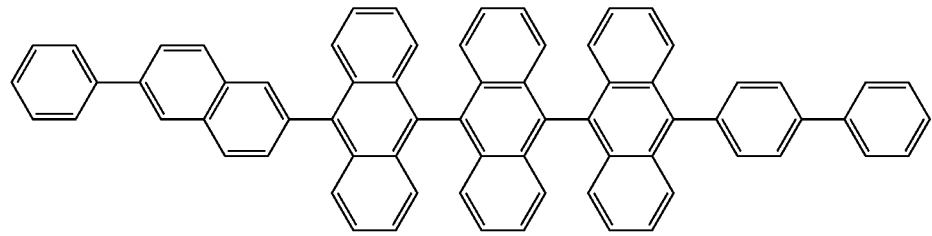

General formula (2b):

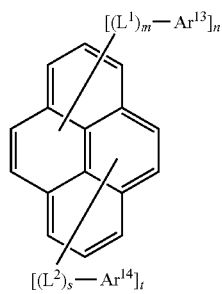

where: $Ar^{13}$ and $A^{14}$ each in dependently represents a substituted or unsubstituted aryl group having 6 to 50 ring carbon atoms;
$L^1$ and $L^2$ each independently selected from a substituted or unsubstituted phenylene group, a substituted or unsubstituted naphthalenylene group, a substituted or unsubstituted fluorenylene group and a substituted or unsubstituted dibenzosilolylene group;
m represents an integer of 0 to 2, n represents an integer of 1 to 4, s represents an integer of 0 to 2 and t represents an integer of 0 to 4; and
$L^1$ or $Ar^{13}$ is bonded to any of 1- to 5-positions of the pyrene ring, and $L^2$ or $Ar^{14}$ is bonded to any of the 6- to 10-positions of the pyrene ring.

Examples of the aryl group having 6 to 50 ring carbon atoms represented by $Ar^{13}$ and $Ar^{14}$ in the general formula (2b) include phenyl group, 1-naphthyl group, 2-naphthyl group, 1-anthryl group, 2-anthryl group, 9-anthryl group, 9-(10-phenyl)anthryl group, 9-(10-naphthyl-1-yl)anthryl group, 9-(10-naphthyl-2-yl)anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, 3-methyl-2-naphthyl group, 4-methyl-1-naphthyl group, 4-methyl-1-anthryl group, etc. Preferable examples are the aromatic ring group having 6 to 16 ring carbon atoms including particularly phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenyl group, 3-biphenylyl group, 4-biphenylyl group, o-tolyl group, m-tolyl group, p-tolyl group, p-t-butylphenyl group.

Further, the aryl group may be further substituted with a substituent, and examples of the substituent include alkyl group (methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamanthyl group, 2-adamanthyl group, 1-norbornyl group, 2-norbornyl group, etc.), an alkoxy group having 1 to 6 carbon atoms (ethoxy group, methoxy group, i-propoxy group, n-propoxy group, s-butoxy group, t-butoxy group, pentoxy group, hexyloxy group, cyclopentoxy group, cyclohexyloxy group, etc.), an aryl group having 6 to 40 ring atoms, an amino group substituted with aryl group having 6 to 40 ring atoms, an ester group with aryl group having 6 to 40 ring atoms, an ester group with alkyl group having 1 to 6 carbon atoms, a cyano group, a nitro group, a halogen atom, etc.

It is preferable for $L^1$ and $L^2$ in the general formula (2b) that they each independently represents one member selected from a substituted or unsubstituted phenylene group and a substituted or unsubstituted fluorenylene group.

Further, examples of the substituent are the same as described about the substituents for the above aromatic groups.

In the general formula (2b), m is preferably an integer of 0 or 1. In the general formula (2b), n is preferably an integer of 1 or 2. In the general formula (2b), s is preferably an integer of 0 or 1.

In the general formula (2b), t is preferably an integer of 0 to 2.

Specific examples of the pyrene derivative represented by the general formula (2b) employed for the organic EL device of the present invention include an asymmetric pyrene derivative which is disclosed in columns [0020] to [0023] of the International PCT publication WO 2005/115950 pamphlet. Besides, a symmetric pyrene derivative is also employable as a material for the organic EL device of the present invention. Typical examples are shown below.

2b-1
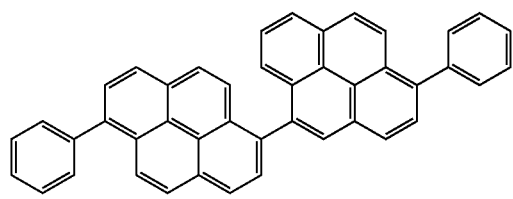
2b-2
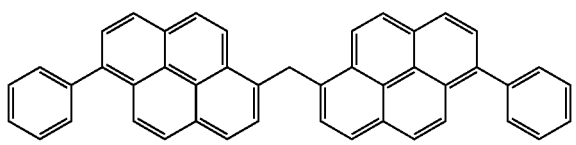
2b-3
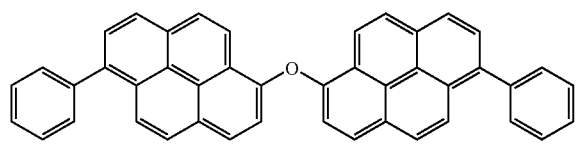
2b-4
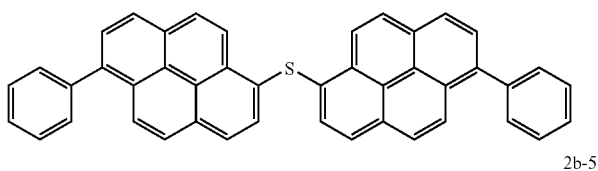
2b-5
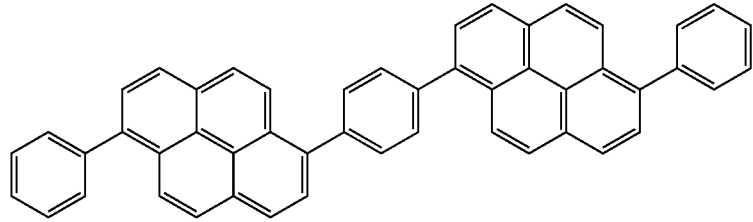
2b-6
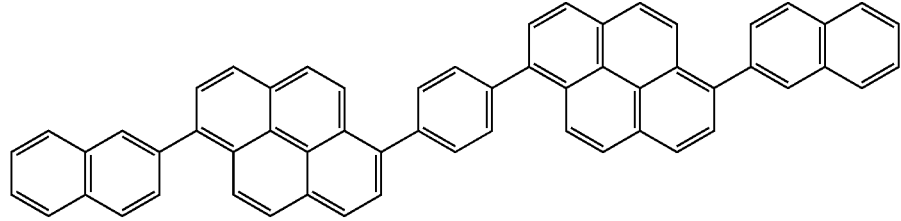
2b-7
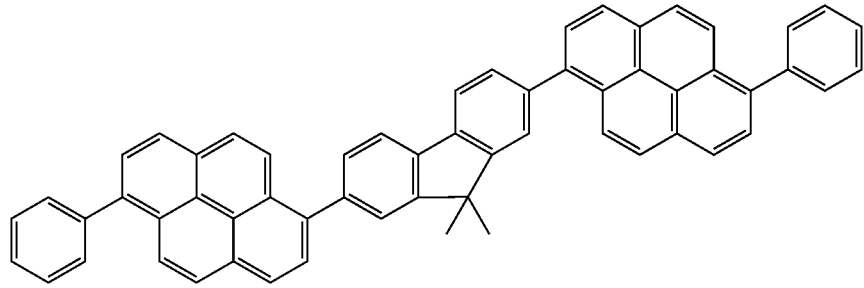
2b-8
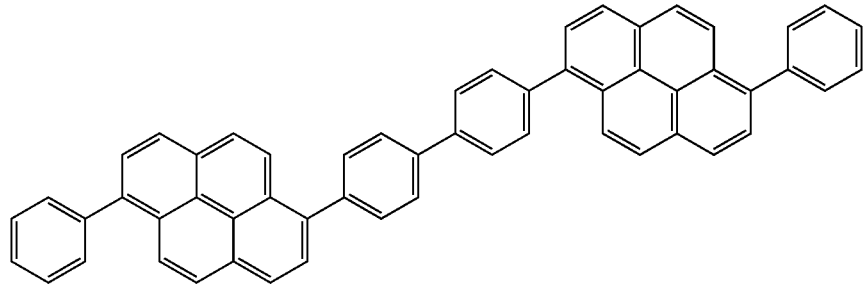

-continued
2b-9
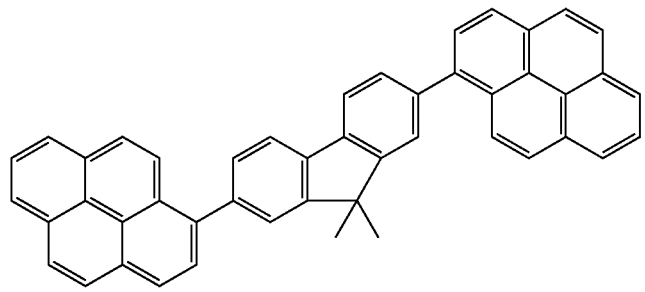
2b-10
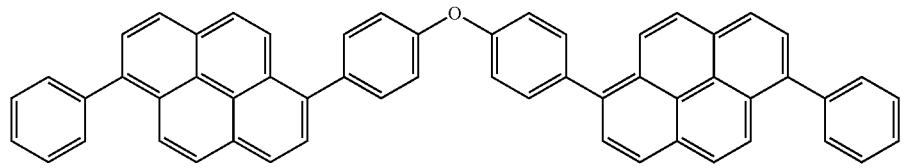
2b-11
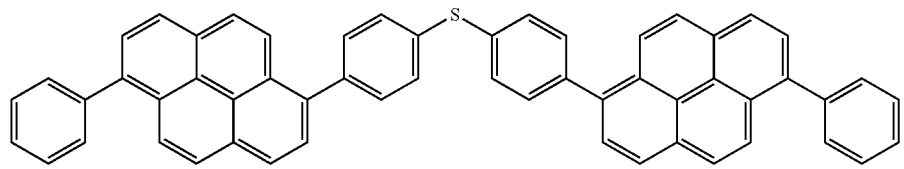
2b-12
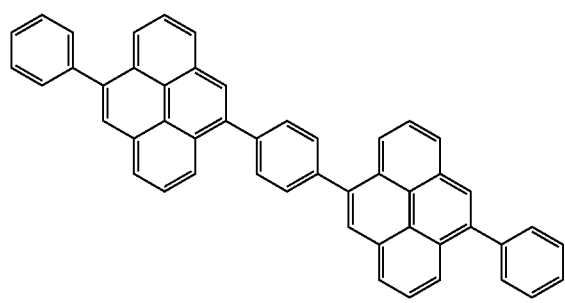
2b-13
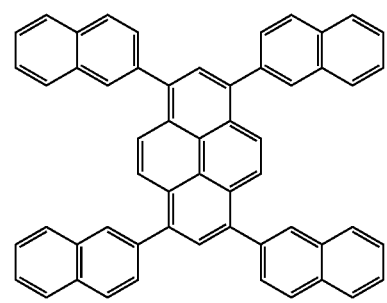
2b-14
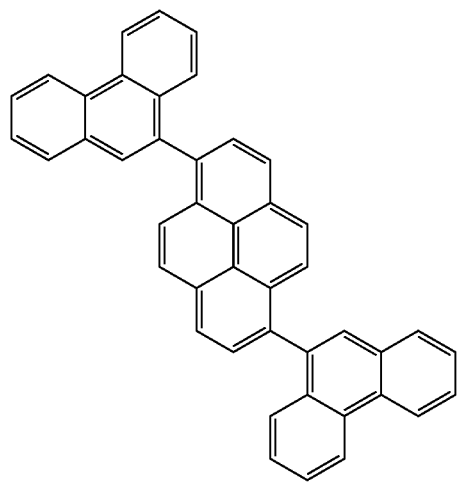
2b-15
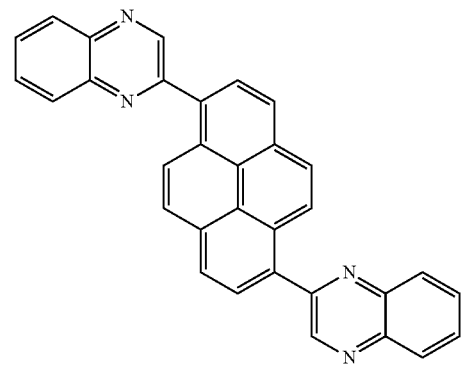

-continued
2b-16
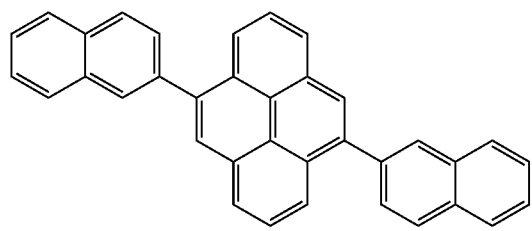
2b-17
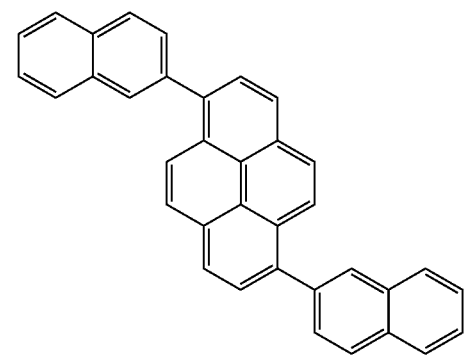
2b-18
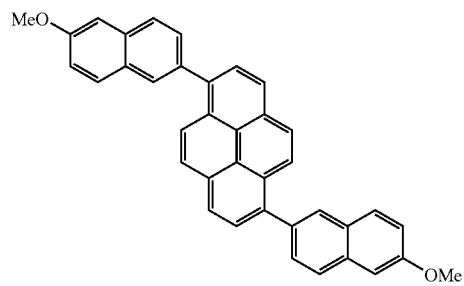
2b-19
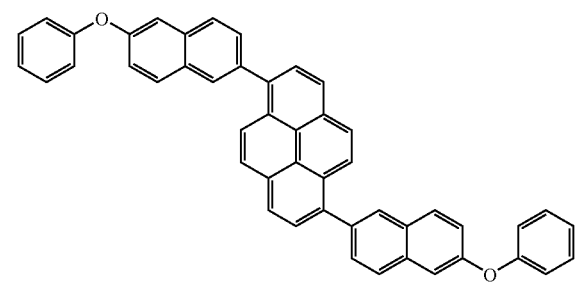
2b-20
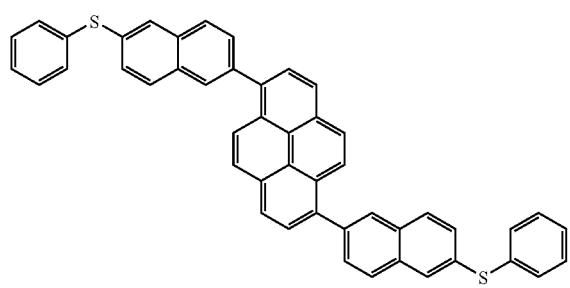
2b-21
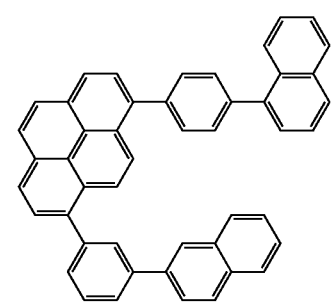
2b-22
2b-23
2b-24
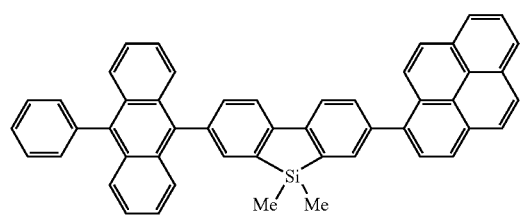
2b-25
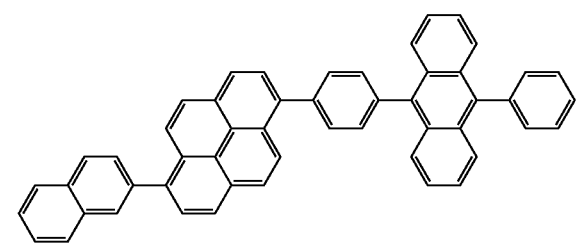

-continued
2b-26
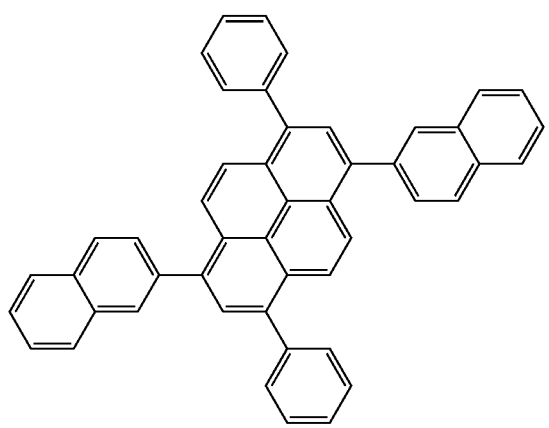
2b-27
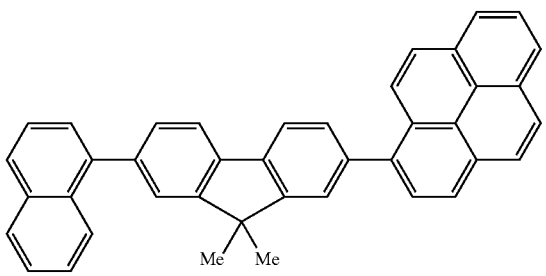
2b-28
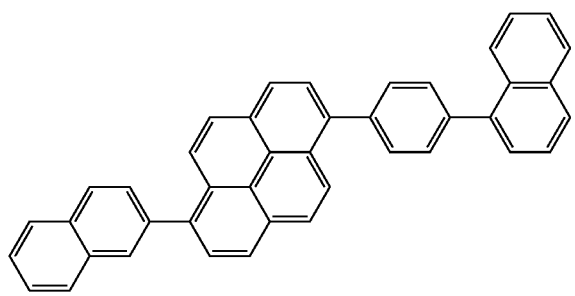
2b-29
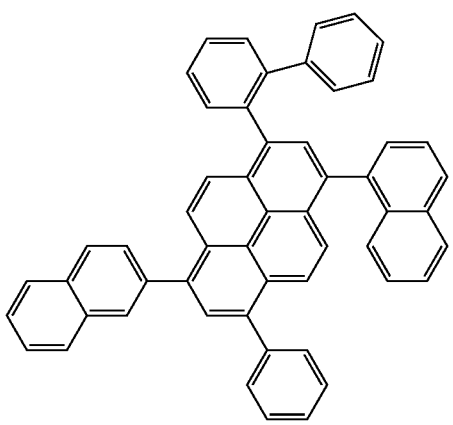
2b-30
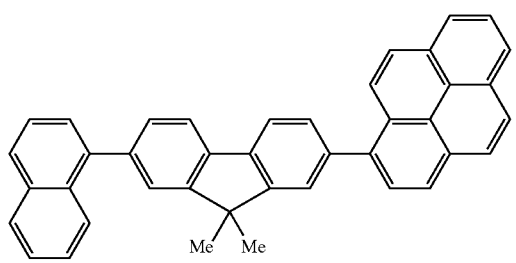
2b-31
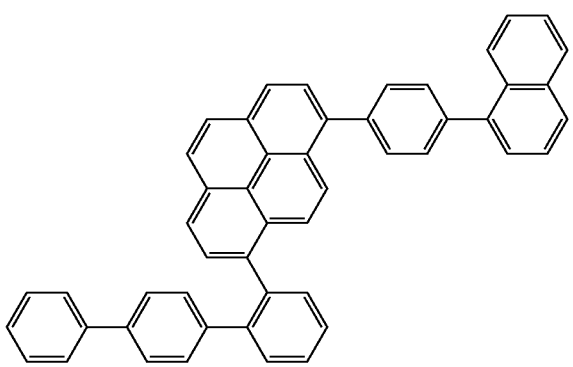

-continued
2b-32
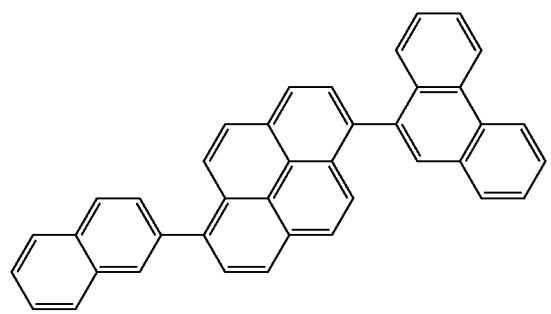
2b-33
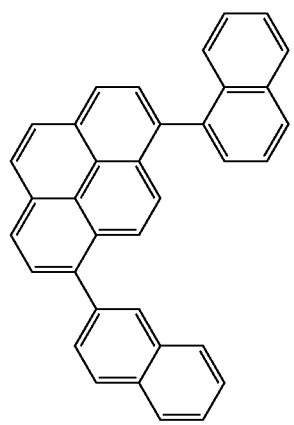
2b-34
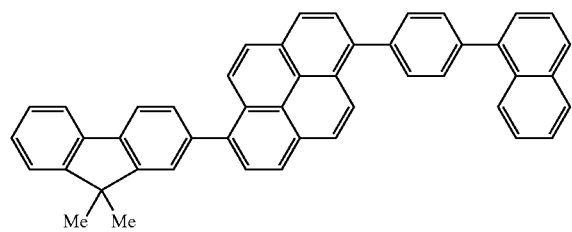
2b-35
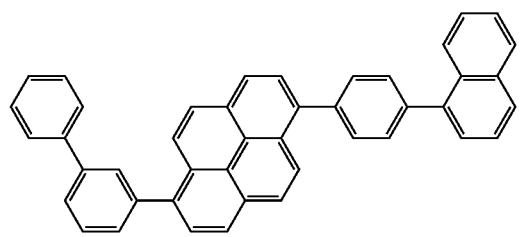
2b-36
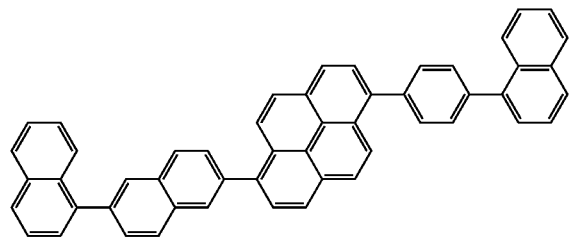
2b-37
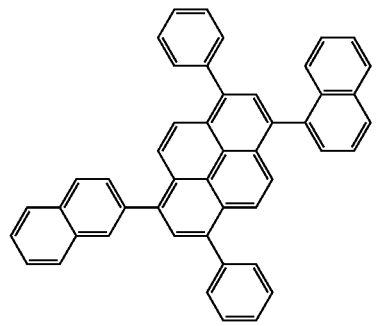
2b-38
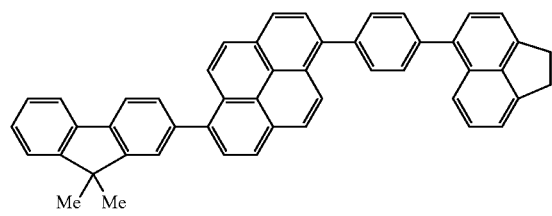
2b-39
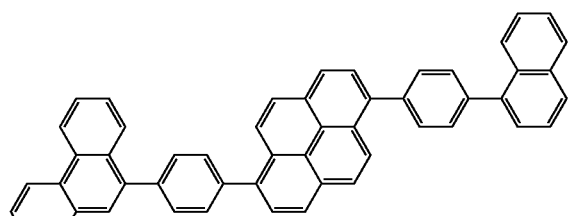
2b-40
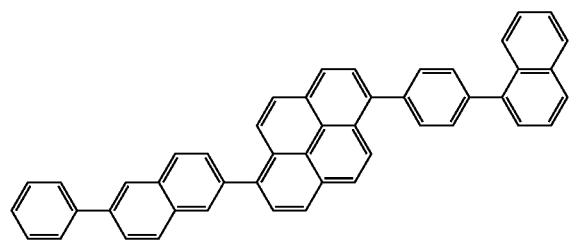
2b-41
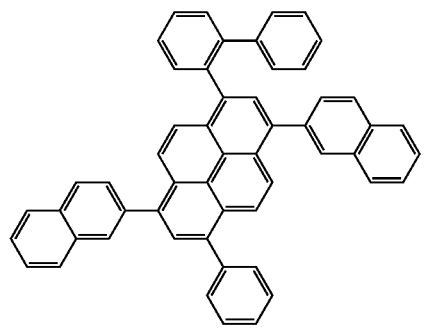

2b-42

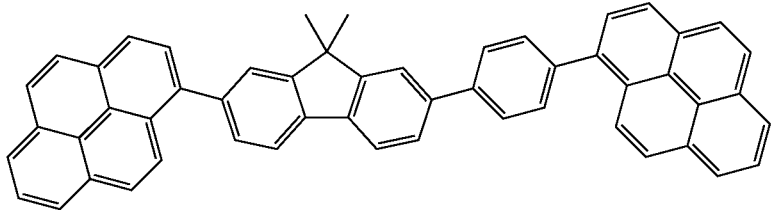

General formula (2c):

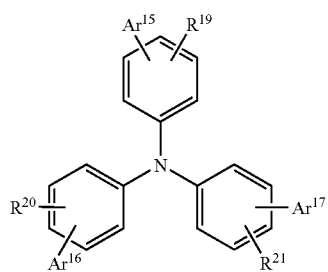

(2c)

where: $Ar^{15}$, $Ar^{16}$ and $Ar^{17}$ each independently is selected from a group having an anthracene structure, a group having a phenanthrene structure and a group having a pyrene structure respectively. $R^{19}$, $R^{20}$ and $R^{21}$ each independently represent a hydrogen atom or a substituent.

It is preferable for $Ar^{15}$, $Ar^{16}$ and $Ar^{17}$ in the general formula (2c) that they each independently represents one member selected from a substituted or unsubstituted anthrylphenyl group, an anthryl group, a phenanthrenyl group, a perilenyl group and a pyrenyl group; more preferably selected from an anthrylphenyl group substituted by alkyl group, an unsubstituted anthrylphenyl group, phenanthryl group and a pyrenyl group; particularly preferably selected from a pyrenyl group and a phenanthryl group.

Examples of $R^{19}$, $R^{20}$ and $R^{21}$ in the general formula (2c) include a hydrogen atom, alkyl group (alkyl group preferably having 1 to 30 carbon atoms, more preferably having 1 to 20 carbon atoms and particularly preferably having 1 to 10 carbon atoms; examples include methyl, ethyl, iso-propyl, tert-butyl, n-octyl, n-decyl, n-hexadecyl, cyclopropyl, cyclopentyl, cyclohexyl, etc.); alkenyl group (alkenyl group preferably having 2 to 30 carbon atoms, more preferably having 2 to 20 carbon atoms and particularly preferably having 2 to 10 carbon atoms; examples include vinyl, allyl, 2-butenyl, 3-pentenyl, etc.); alkynyl group (alkynyl group preferably having 2 to 30 carbon atoms, more preferably having 2 to 20 carbon atoms and particularly preferably having 2 to 10 carbon atoms; examples include propargyl, 3-pentynyl, etc.); aryl group (aryl group having 6 to 30 carbon atoms, more preferably having 6 to 20 carbon atoms and particularly preferably having 6 to 12 carbon atoms; examples include phenyl, p-methylphenyl, naphthyl, anthranyl, etc.); amino group (amino group preferably having 0 to 30 carbon atoms, more preferably having 0 to 20 carbon atoms and particularly preferably having 0 to 10 carbon atoms; examples include amino, methylamino, dimethylamino, diethylamino, dibenzylamino, diphenylamino, ditolylamino, etc.); alkoxy group (alkoxy group preferably having 1 to 30 carbon atoms, more preferably having 1 to 20 carbon atoms and particularly preferably having 1 to 10 carbon atoms; examples include methoxy, ethoxy, butoxy, 2-ethylhexyloxi, etc.); aryloxy group (aryloxy group preferably having 6 to 30 carbon atoms, more preferably having 6 to 20 carbon atoms and particularly preferably having 6 to 12 carbon atoms; examples include phenyloxy, 1-naphthyloxy, 2-naphthyloxy, etc.); heteroaryloxy group (heteroaryloxy group preferably having 1 to 30 carbon atoms, more preferably having 1 to 20 carbon atoms and particularly preferably having 1 to 12 carbon atoms; examples include pyridyloxy, pyrazyloxy, pyrimidyloxy, quinolyloxy, etc.); acyl group (acyl group preferably having 1 to 30 carbon atoms, more preferably having 1 to 20 carbon atoms and particularly preferably having 1 to 12 carbon atoms; examples include acetyl, benzoyl, formyl, pivaloyl, etc.); alkoxycarbonyl group (alkoxycarbonyl group preferably having 2 to 30 carbon atoms, more preferably having 2 to 20 carbon atoms and particularly preferably having 2 to 12 carbon atoms; examples include methoxycarbonyl, ethoxycarbonyl, etc.); aryloxycarbonyl group (aryloxycarbonyl group preferably having 7 to 30 carbon atoms, more preferably having 7 to 20 carbon atoms and particularly preferably having 7 to 12 carbon atoms; examples include phenyloxycarbonyl, etc.); acyloxy group (acyloxy group preferably having 2 to 30 carbon atoms, more preferably having 2 to 20 carbon atoms and particularly preferably having 2 to 10 carbon atoms; examples include acetoxy, benzoyloxy, etc.); acylamino group (acylamino group preferably having 2 to 30 carbon atoms, more preferably having 2 to 20 carbon atoms and particularly preferably having 2 to 10 carbon atoms; examples include acetylamino, benzoylamino, etc.); alkoxycarbonylamino group (alkoxycarbonylamino group preferably having 2 to 30 carbon atoms, more preferably having 2 to 20 carbon atoms and particularly preferably having 2 to 12 carbon atoms; examples include methoxycarbonylamino, etc.); aryloxycarbonylamino group (aryloxycarbonylamino group preferably having 7 to 30 carbon atoms, more preferably having 7 to 20 carbon atoms and particularly preferably having 7 to 12 carbon atoms; examples include phenyloxycarbonylamino, etc.); sulfonylamino group (sulfonylamino group preferably having 1 to 30 carbon atoms, more preferably having 1 to 20 carbon atoms and particularly preferably having 1 to 12 carbon atoms; examples include methanesulfonylamino, benzensulfonylamino, etc.); sulfamoyl group (sulfamoyl group preferably having 0 to 30 carbon atoms, more preferably having 0 to 20 carbon atoms and particularly preferably having 0 to 12 carbon atoms; examples include sulfamoyl, methylsulfamoyl, dimethylsulfamoyl, phenylsulfamoyl, etc.); carbamoyl group (carbamoyl group preferably having 1 to 30 carbon atoms, more preferably having 1 to 20 carbon atoms and particularly preferably having 1 to 12 carbon atoms; examples include carbamoyl, methylcarbamoyl, diethylcarbamoyl, phenylcarbamoyl, etc.); alkylthio group (alkylthio group preferably having 1 to 30 carbon atoms, more preferably having 1 to 20 carbon atoms and particularly preferably having 1 to 12 carbon atoms; examples include methylthio, ethylthio, etc.); arylthio group (arylthio group preferably having 6 to 30 carbon atoms, more preferably having 6 to 20 carbon atoms and particularly preferably having 6 to 12 carbon atoms; examples include phenylthio, etc.); heteroarylthio group (heteroarylthio group preferably having 1 to 30 carbon atoms, more preferably having 1 to 20 carbon atoms and particularly preferably having 1 to 12 carbon atoms; examples include pyridylthio, 2-benzimidazolylthio, 2-benzoxazolylthio, 2-benzthiazolylthio, etc.); sulfonyl group (sulfonyl group preferably having 1 to 30 carbon atoms, more preferably having 1 to 20 carbon atoms and particularly preferably having 1 to 12 carbon atoms; examples include mesyl, tosyl, etc.); sulfinyl group (sulfinyl group preferably having 1 to 30 carbon atoms, more preferably having 1 to 20 carbon atoms and particularly preferably having 1 to 12 carbon atoms; examples include methanesulfinyl, benzenesulfinyl, etc.); ureide group (ureide group preferably having 1 to 30 carbon atoms, more preferably having 1 to 20 carbon atoms and particularly preferably having 1 to 12 carbon atoms; examples include ureide, methylureide, phenylureide, etc.); phosphoric acid amide group (phosphoric acid amide group preferably having 1 to 30 carbon atoms, more preferably having 1 to 20 carbon atoms and particularly preferably having 1 to 12 carbon atoms; examples include diethylphosphoric acid amide, phenylphosphateamide, etc.); hydroxy group; mercapto group; halogen atoms (for example, a fluorine atom, a chlorine atom, a bromine atom and an iodine atom); cyano group; sulfo group; carboxyl group; nitro group; hydroxamic acid group; sulfino group; hydrazino group; imino group; heterocyclic group (heterocyclic group preferably having 1 to 30 carbon atoms, more preferably having 1 to 12 carbon atoms; examples of hetero atoms include a nitrogen atom, an oxygen atom, a sulfur atom; specific examples of the heterocyclic group include imidazolyl, pyridyl, quinolyl, furyl, thienyl, piperidyl, morpholino, benzoxazolyl, benzimidazolyl, benzothiazolyl, etc.); silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted.

The substituents of $R^{17}$, $R^{20}$ and $R^{21}$ in the general formula (2c) are preferably selected from alkyl group and aryl group.

Specific examples of the amine derivative represented by the general formula (2c) employed for the organic EL device of the present invention include various kinds of publicly known amine derivatives which are disclosed in columns [0079] to [0083] of JP 2002-324678A. Typical examples are shown below.

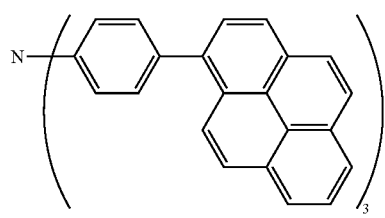

2c-1

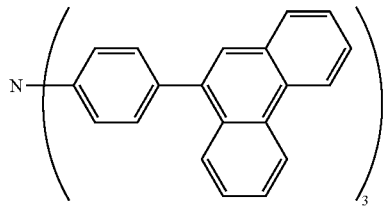

2c-2

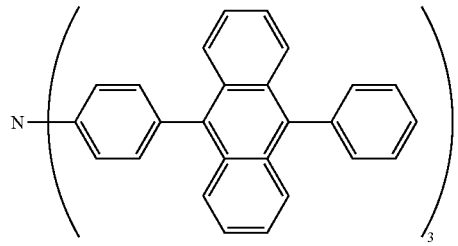

2c-3

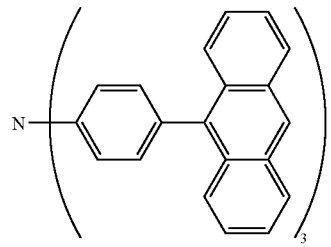

2c-4

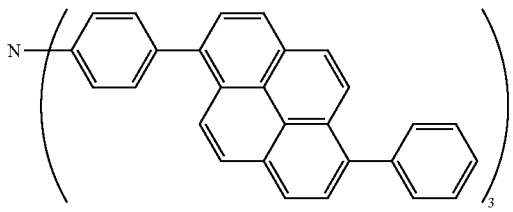

2c-5

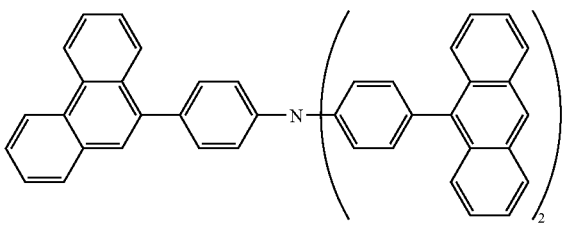

2c-6

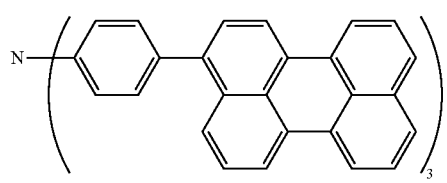

2c-8

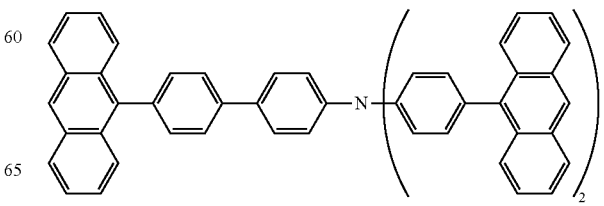

2c-10

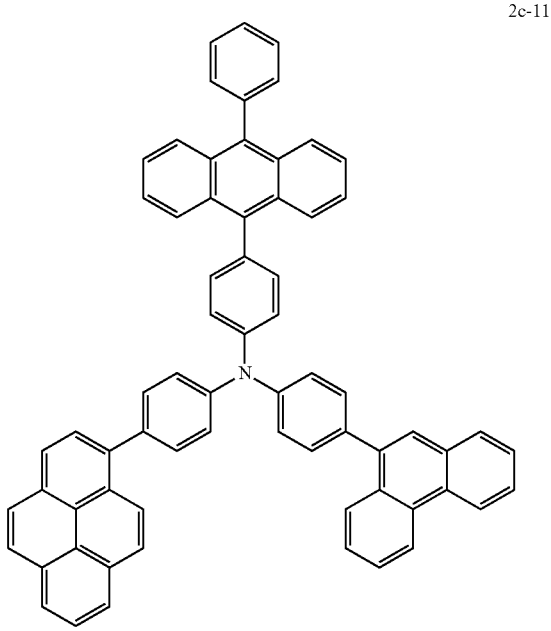

2c-11

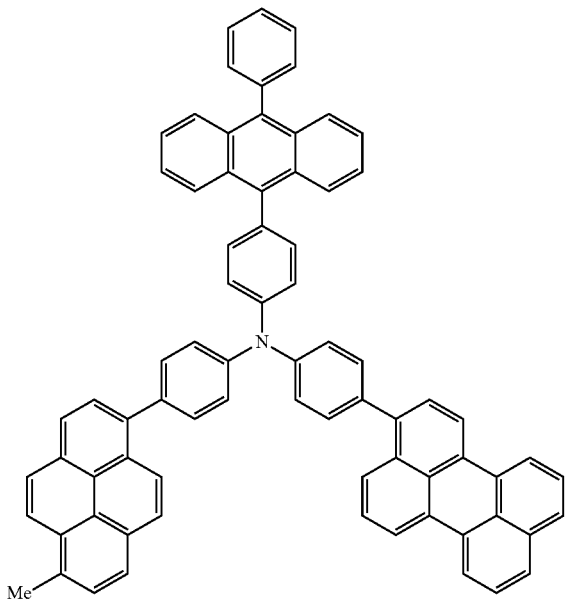

2c-12

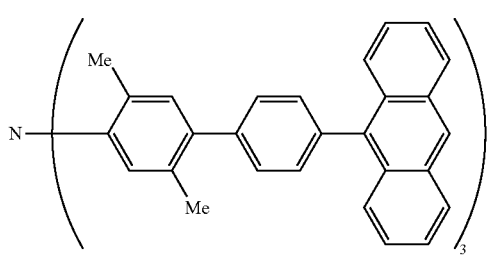

2c-13

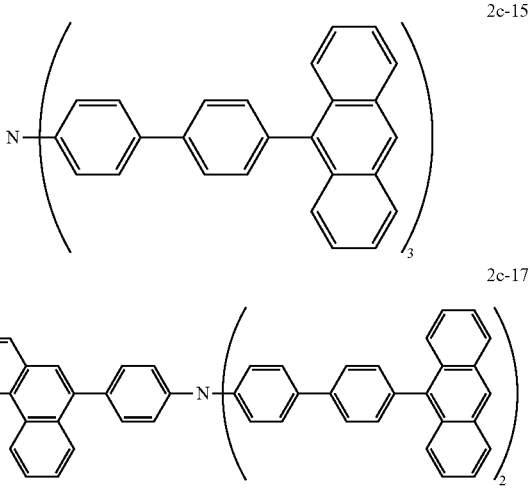

2c-15

2c-17

General formula (2d):

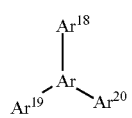

(2d)

where: $Ar^{18}$, $Ar^{19}$ and $Ar^{20}$ each independently represents an aryl group having 6 to 50 ring carbon atoms;

the aryl group may be substituted by 1 or more substituents; at least one of the aryl groups represented by $Ar^{18}$, $Ar^{19}$, $Ar^{20}$, and those substituents has a fused ring aryl structure having 10 to 20 ring carbon atoms or a fused ring heteroaryl structure having 6 to 20 ring carbon atoms; and Ar represents a trivalent group derived from an aromatic ring or a heteroaromatic ring.

The aryl group having 6 to 50 ring carbon atoms represented by $Ar^{18}$, $Ar^{19}$ and $Ar^{20}$ of the general formula (2d) has preferably 6 to 30 ring carbon atoms, more preferably 6 to 20 ring carbon atoms, and further preferably 6 to 16 ring carbon atoms. Examples of the aryl group include phenyl group, naphthyl group, anthryl group, phenanthrenyl group, pyrenyl group, perilenyl group, fluorenyl group, biphenylyl group, terphenylyl group, rubrenyl group, crycenyl group, triphenylenyl group, benzanthryl group, benzphenanthrenyl group, diphenylanthryl group, etc., and those aryl groups may be further substituted.

Examples of the substituents on the aryl groups include alkyl group (alkyl group preferably having 1 to 30 carbon atoms, more preferably having 1 to 20 carbon atoms and particularly preferably having 1 to 10 carbon atoms; examples include methyl, ethyl, iso-propyl, tert-butyl, n-octyl, n-decyl, n-hexadecyl, cyclopropyl, cyclopentyl, cyclohexyl, etc.); alkenyl group (alkenyl group preferably having 2 to 30 carbon atoms, more preferably having 2 to 20 carbon atoms and particularly preferably having 2 to 10 carbon atoms; examples include vinyl, allyl, 2-butenyl, 3-pentenyl, etc.); alkynyl group (alkynyl group preferably having 2 to 30 carbon atoms, more preferably having 2 to 20 carbon atoms and particularly preferably having 2 to 10 carbon atoms; examples include propargyl, 3-pentynyl, etc.); aryl group (aryl group having 6 to 30 carbon atoms, more preferably having 6 to 20 carbon atoms and particularly preferably having 6 to 12 carbon atoms; examples include phenyl, p-methylphenyl, naphthyl, anthranyl, etc.); amino group (amino group preferably having 0 to 30 carbon atoms, more preferably having 0 to 20 carbon atoms and particularly preferably having 0 to 10 carbon atoms; examples include amino, methylamino, dimethylamino, diethylamino, dibenzylamino, diphenylamino, ditolylamino, etc.); alkoxy group (alkoxy group preferably having 1 to 30 carbon atoms, more preferably having 1 to 20 carbon atoms and particularly preferably having 1 to 10 carbon atoms; examples include methoxy, ethoxy, butoxy, 2-ethylhexyloxy, etc.); aryloxy group (aryloxy group preferably having 6 to 30 carbon atoms, more preferably having 6 to 20 carbon atoms and particularly preferably having 6 to 12 carbon atoms; examples include phenyloxy, 1-naphthyloxy, 2-naphthyloxy, etc.); heteroaryloxy group (heteroaryloxy group preferably having 1 to 30 carbon atoms, more preferably having 1 to 20 carbon atoms and particularly preferably having 1 to 12 carbon atoms; examples include pyridyloxy, pyrazyloxy, pyrimidyloxy, quinolyloxy, etc.); acyl group (acyl group preferably having 1 to 30 carbon atoms, more preferably having 1 to 20 carbon atoms and particularly preferably having 1 to 12 carbon atoms; examples include acetyl, benzoyl, formyl, pivaloyl, etc.); alkoxycarbonyl group (alkoxycarbonyl group preferably having 2 to 30 carbon atoms, more preferably having 2 to 20 carbon atoms and particularly preferably having 2 to 12 carbon atoms; examples include methoxycarbonyl, ethoxycarbonyl, etc.); aryloxycarbonyl group (aryloxycarbonyl group preferably having 7 to 30 carbon atoms, more preferably having 7 to 20 carbon atoms and particularly preferably having 7 to 12 carbon atoms; examples include phenyloxycarbonyl, etc.); acyloxy group (acyloxy group preferably having 2 to 30 carbon atoms, more preferably having 2 to 20 carbon atoms and particularly preferably having 2 to 10 carbon atoms; examples include acetoxy, benzoyloxy, etc.); acylamino group (acylamino group preferably having 2 to 30 carbon atoms, more preferably having 2 to 20 carbon atoms and particularly preferably having 2 to 10 carbon atoms; examples include acetylamino, benzoylamino, etc.); alkoxycarbonylamino group (alkoxycarbonylamino group preferably having 2 to 30 carbon atoms, more preferably having 2 to 20 carbon atoms and particularly preferably having 2 to 12 carbon atoms; examples include methoxycarbonylamino, etc.); aryloxycarbonylamino group (aryloxycarbonylamino group preferably having 7 to 30 carbon atoms, more preferably having 7 to 20 carbon atoms and particularly preferably having 7 to 12 carbon atoms; examples include phenyloxycarbonylamino, etc.); sulfonylamino group (sulfonylamino group preferably having 1 to 30 carbon atoms, more preferably having 1 to 20 carbon atoms and particularly preferably having 1 to 12 carbon atoms; examples include methanesulfonylamino, benzensulfonylamino, etc.); sulfamoyl group (sulfamoyl group preferably having 0 to 30 carbon atoms, more preferably having 0 to 20 carbon atoms and particularly preferably having 0 to 12 carbon atoms; examples include sulfamoyl, methylsulfamoyl, dimethylsulfamoyl, phenylsulfamoyl, etc.); carbamoyl group (carbamoyl group preferably having 1 to 30 carbon atoms, more preferably having 1 to 20 carbon atoms and particularly preferably having 1 to 12 carbon atoms; examples include carbamoyl, methylcarbamoyl, diethylcarbamoyl, phenylcarbamoyl, etc.); alkylthio group (alkylthio group preferably having 1 to 30 carbon atoms, more preferably having 1 to 20 carbon atoms and particularly preferably having 1 to 12 carbon atoms; examples include methylthio, ethylthio, etc.); arylthio group (arylthio group preferably having 6 to 30 carbon atoms, more preferably having 6 to 20 carbon atoms and particularly preferably having 6 to 12 carbon atoms; examples include phenylthio, etc.); heteroarylthio group (heteroarylthio group preferably having 1 to 30 carbon atoms, more preferably having 1 to 20 carbon atoms and particularly preferably having 1 to 12 carbon atoms; examples include pyridylthio, 2-benzimidazolylthio, 2-benzoxazolylthio, 2-benzthiazolylthio, etc.); sulfonyl group (sulfonyl group preferably having 1 to 30 carbon atoms, more preferably having 1 to 20 carbon atoms and particularly preferably having 1 to 12 carbon atoms; examples include mesyl, tosyl, etc.); sulfinyl group (sulfinyl group preferably having 1 to 30 carbon atoms, more preferably having 1 to 20 carbon atoms and particularly preferably having 1 to 12 carbon atoms; examples include methanesulfinyl, benzenesulfinyl, etc.); ureide group (ureide group preferably having 1 to 30 carbon atoms, more preferably having 1 to 20 carbon atoms and particularly preferably having 1 to 12 carbon atoms; examples include ureide, methylureide, phenylureide, etc.); phosphoric acid amide group (phosphoric acid amide group preferably having 1 to 30 carbon atoms, more preferably having 1 to 20 carbon atoms and particularly preferably having 1 to 12 carbon atoms; examples include diethyl phosphoric acid amide, phenylphosphateamide, etc.); hydroxy group; mercapto group; halogen atoms (for example, a fluorine atom, a chlorine atom, a bromine atom, an iodine atom, etc.); cyano group; sulfo group; carboxyl group; nitro group; hydroxamic acid group; sulfino group; hydrazino group; imino group; heterocyclic group (heterocyclic group preferably having 1 to 30 carbon atoms, more preferably having 1 to 12 carbon atoms; examples of the hetero atoms include a nitrogen atom, an oxygen atom, a sulfur atom; specific examples of the hetero atoms include imidazolyl, pyridyl, quinolyl, furyl, thienyl, piperidyl, morpholino, benzoxazolyl, benzimidazolyl, benzothiazolyl, carbazolyl group, azepinyl group, etc.); silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted.

Examples of the fused ring aryl structure having 10 to 20 ring carbon atoms held by at least one substituent of $Ar^{18}$, $Ar^{19}$, $Ar^{20}$ in the general formula (2d) and those aryl groups include naphthalene structure, anthracene structure, phenanthrene structure, pyrene structure, perylene structure, etc.; preferably naphthalene structure, anthracene structure, pyrene structure and phenanthrene structure; more preferably phenanthrene structure and aryl structure having 4 or more rings; particularly preferably pyrene structure.

Examples of the fused ring heteroaryl structure having 6 to 20 ring carbon atoms held by at least one substituent of $Ar^{18}$, $Ar^{19}$, and $Ar^{20}$ in the general formula (2d) and those aryl groups include quinoline structure, quinoxaline structure, quinazoline structure, acridine structure, phenanthridine structure, phthalazine structure, phenanthroline structure, etc.; preferably quinoline structure, quinoxaline structure, quinazoline structure, phthalazine structure and phenanthroline structure.

Trivalent groups derived from the aromatic ring represented by Ar of the general formula (2d) have preferably 6 to 30 carbon atoms, more preferably 6 to 20 carbon atoms, and further preferably 6 to 16 carbon atoms. Specific examples include the trivalent groups derived from benzene, naphthalene, anthran, phenanthrene, pyrene, triphenylene, etc.

Trivalent groups derived from the heteroaromatic ring represented by Ar in the general formula (2d) preferably include an atom selected from a nitrogen atom, a sulfur atom and an oxygen atom as hetero atoms, and more preferably include a nitrogen atom. Moreover, it has preferably 2 to 30 carbon atoms, more preferably 3 to 20 carbon atoms, and further preferably 3 to 16 carbon atoms. Specific examples include the trivalent groups derived from pyridine, pyrazine, thiopyran, quinoline, quinoxaline and triazine.

Trivalent groups derived from those aromatic rings or heteroaromatic rings may be substituted by a substituent except $Ar^{18}$, $Ar^{19}$ and $Ar^{20}$. Examples of the substituent include the groups described about the substituent on the aryl group represented by the substituent $Ar^{18}$. Ar is preferably a trivalent group derived from benzenetriyl, naphthalenetriyl, anthracenetriyl, pyrenetriyl, triphenylene; more preferably from benzenetriyl; and further preferably from unsubstituted (with the proviso that $Ar^{18}$, $Ar^{19}$ and $Ar^{20}$ are substituted) benzenetriyl and benzenetriyl substituted by alkyl.

Specific examples of the benzene derivative represented by the general formula (2d) employed for the organic EL device of the present invention include various kinds of publicly known benzene derivatives which are disclosed in columns [0079] to [0083] of JP 2002-324678A. Typical examples are shown below.

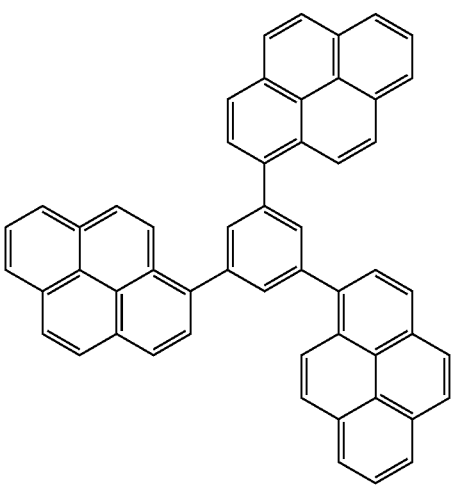

2d-1

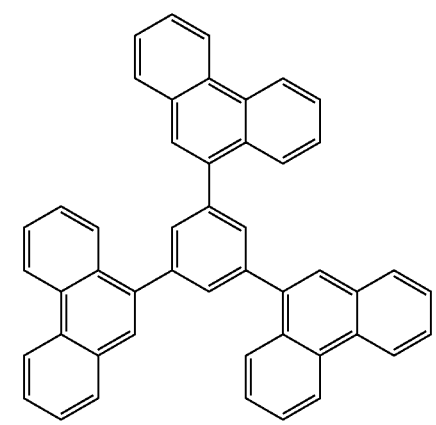

2d-2

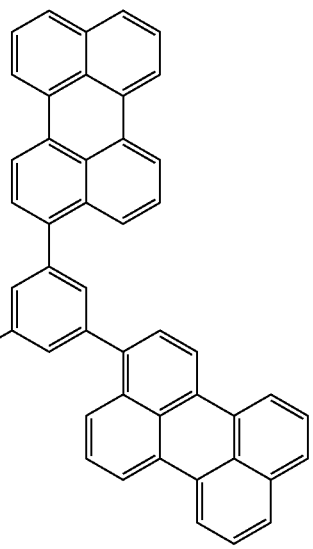

2d-3

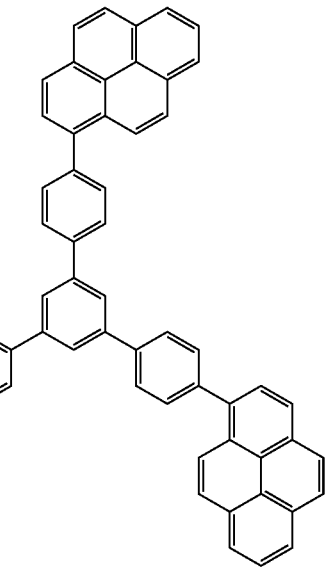

2d-4

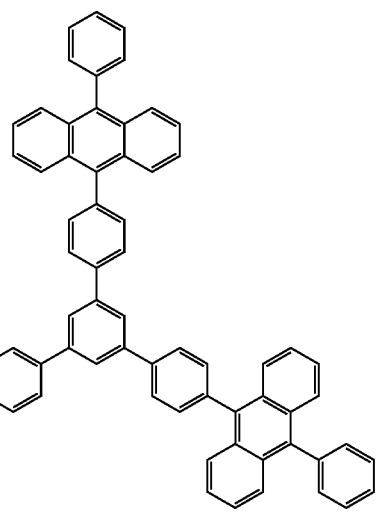

2d-5

2d-6
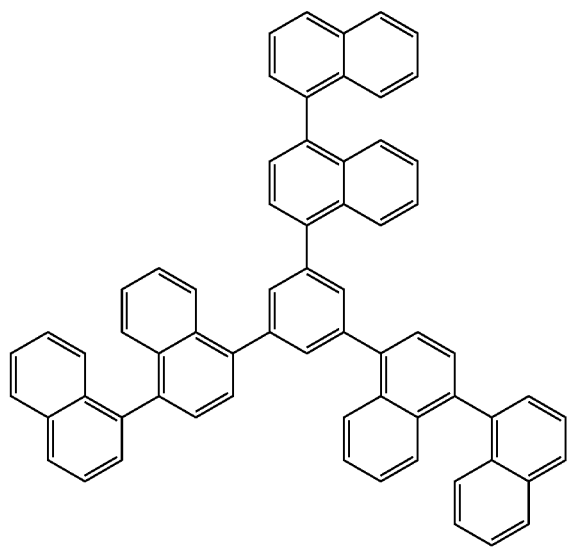
2d-7
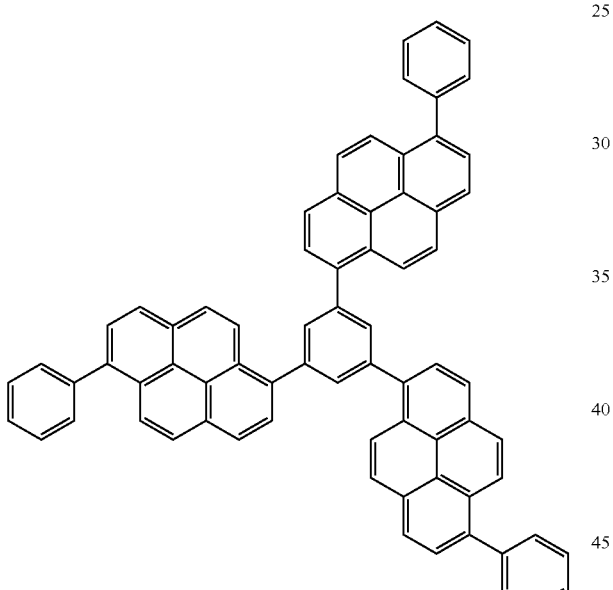
2d-8
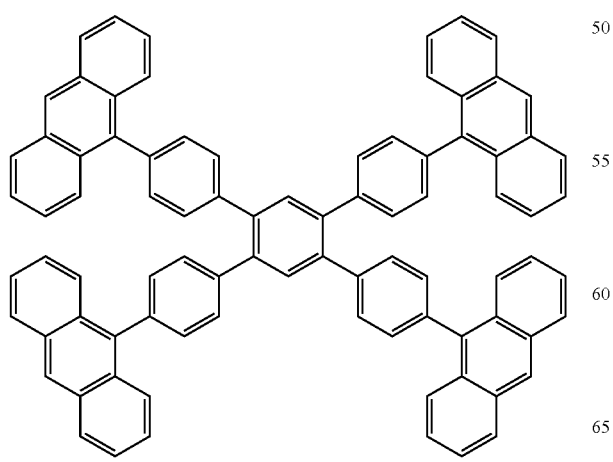
2d-9
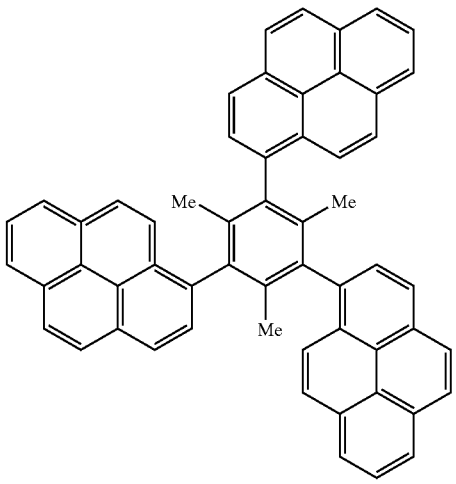
2d-10
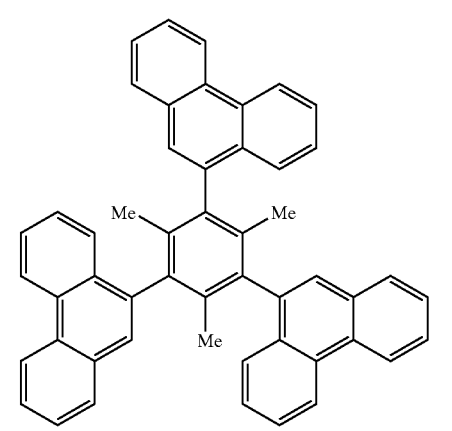
2d-11
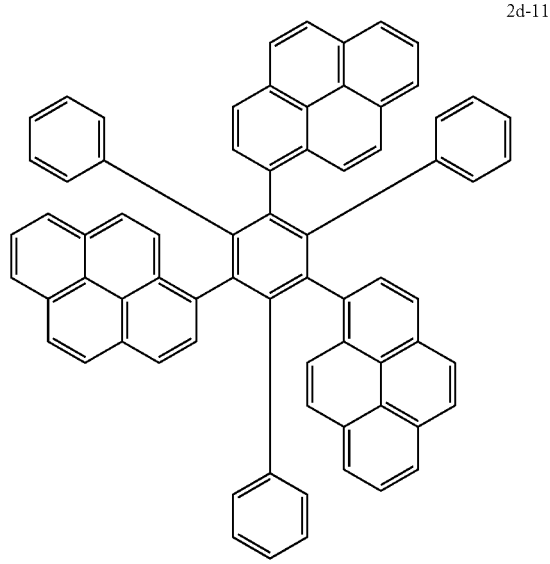

2d-12
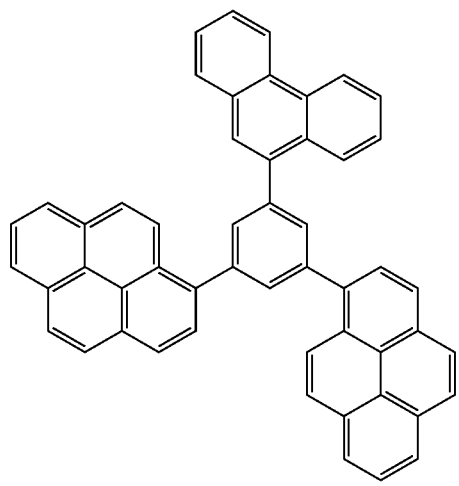
2d-15
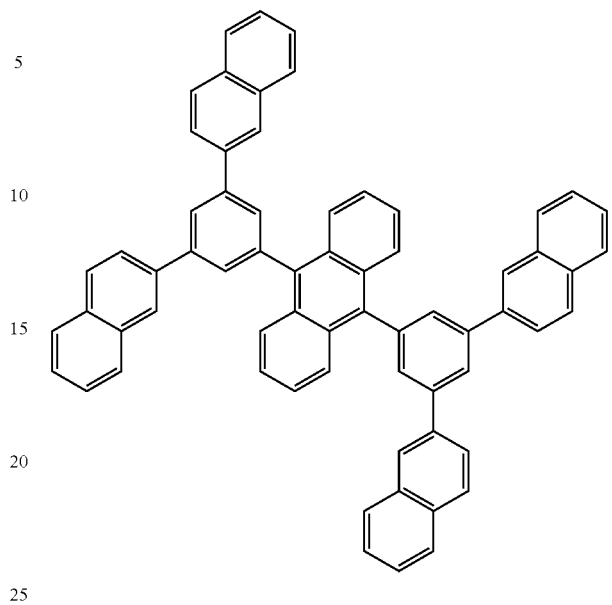
2d-13
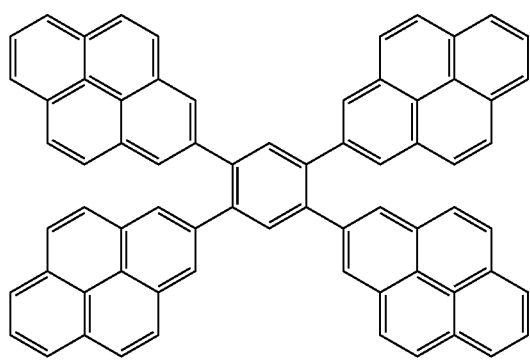
2d-16
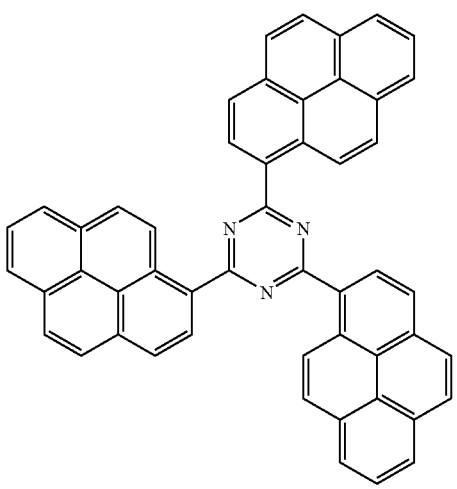
2d-14
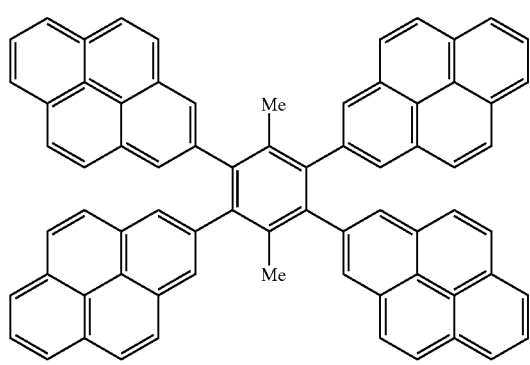
2d-17
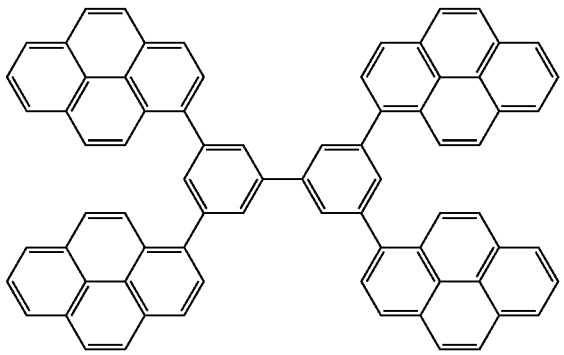

2d-18

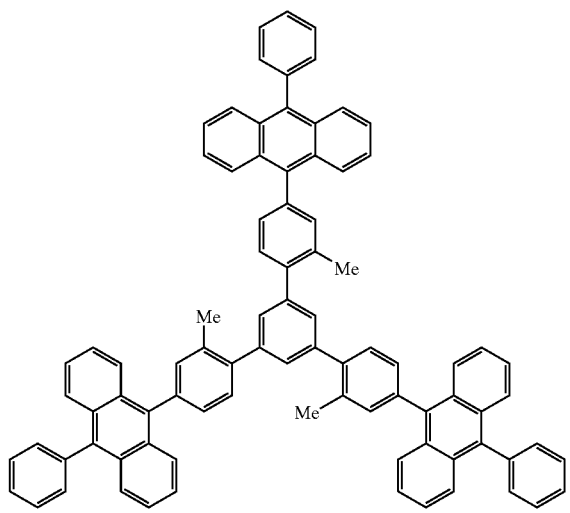

Examples of the organic EL device having plural organic thin film layers include those having a multilayer structure such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The respective plural organic thin film layers may also optionally contain, in addition to the trinaphthyl monoamine or a derivative thereof in the present invention, publicly known light emitting materials, doping materials, hole injecting materials and electron injecting materials as occasion demands. The organic EL device having such plural organic thin film layers can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance of light emission and efficiency of light emission, and further emit a red color light or a blue color light. Further, in the organic EL device of the present invention, the hole injecting layer, the light emitting layer and the electron injecting layer may respectively have a laminated structure including two or more layers. In this occasion, the multi-layer hole injecting layer may be constituted from a hole injecting layer into which holes are injected from the electrode, and a hole transporting layer for accepting the holes from the hole injecting layer and transporting the holes to the light emitting layer. Also, the multi-layer electron injecting layer may be constituted from an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the other organic thin film layers or the metal electrodes.

Examples of the host material or the doping material except the foregoing general formulae (2a) to (2d) employable for the light emitting layer together with the trinaphthyl monoamine or a derivative thereof in the present invention include fused mass aromatic compound such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, 1,4-bis(9'-ethynylanthracenyl)benzene; those derivatives; organometallic complex such as tris(8-quinolinolato)aluminum, bis-(2-methyl-8-quinolinolato)-4-(phenylphenolinato)aluminum, etc.; triarylamine derivatives, styrylamine derivatives, stilbene derivatives, coumarin derivatives, pyran derivatives, oxazone derivatives, benzothiazole derivatives, benzoxazole derivatives, benzimidazole derivatives, pyrazine derivatives, cinnamate ester derivatives, diketopyrrolopyrrole derivatives, acridone derivatives, quinacridone derivatives, etc.; though not particularly limited thereto.

The hole injecting material is preferably made of compounds which have a good hole transportability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the compound include, but are not limited to, phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a electrically conductive polymer.

Of these hole injecting materials usable in the organic EL device of the present invention, more effective hole injecting materials are aromatic tertiary amine derivatives and phthalocyanine derivatives.

Specific examples of the aromatic tertiary amine derivatives include triphenylamine, tritolylamine, tolyldiphenylamine, N,N'-diphenyl-N,N'(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O—GaPc, as well as naphthalocyanine derivatives, though not particularly limited thereto.

Also, in the organic EL device of the present invention, between the light emitting layer and the anode, there is preferably provided a layer containing these aromatic tertiary amine derivatives and/or phthalocyanine derivatives, for example, the above hole transporting layer or hole injecting layer.

The electron injecting material is preferably made of compounds which have a good electron transportability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. Further, an electron accepting substance and an electron donating substance may be added to the hole injecting material and the electron injecting material, respectively, for enhancing sensitization thereof.

In the organic EL device of the present invention, more effective electron injecting materials are metal complex compounds and nitrogen-containing five-membered ring derivatives.

Specific examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato)beryllium, bis(10-hydroxybenzo[h]quinolinato) zinc, bis(2-methyl-8-quinolinato) chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, though not particularly limited thereto.

Examples of the preferred nitrogen-containing five-membered ring derivatives include derivatives of oxazole, thiazole, oxadiazole, thiadiazole or triazole. Specific examples of the derivative include, 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-t-butylphenyl)-5-(4'-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-t-butylbenzene], 2-(4'-tertbutylphenyl)-5-(4'-biphenyl)-1,3,4-thiadiazole, 2,5-bis(1-naphthyl)-1,3,4-thiadiazole, 1,4-bis[2-(5-phenylthiadiazolyl)]benzene, 2-(4'-t-butylphenyl)-5-(4'-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain at least one material selected from the group consisting of light emitting materials, doping materials, hole injecting materials and electron injecting materials, in addition to the trinaphthyl monoamine or a derivative thereof represented by at least one selected from the general formulae (I) to (III), In addition, the surface of the organic EL device obtained in accordance with the present invention can be provided with a protective layer, or the entire device can be protected with silicone oil, a resin, or the like with a view to improving the stability of the device against temperature, humidity, an atmosphere, or the like.

The anode of the organic EL device according to the present invention may be suitably made of an electrically conductive material having a work function of exceeding 4 eV. Examples of the electrically conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic electrically conductive resins such as polythiophene and polypyrrole. The cathode of the organic EL device according to the present invention may be suitably made of a conductive material having a work function of 4 eV or less. Examples of the electrically conductive material for the cathode include magnesium, calcium, tin, lead, titanium, yttrium, lithium, ruthenium, manganese, aluminum, lithium fluoride and alloys thereof, though not particularly limited thereto. Representative examples of the alloys include, but are not limited to, a magnesium/silver alloy, a magnesium/indium alloy, and a lithium/aluminum alloy. A composition ratio of an alloy is controlled depending on, for example, the temperature of a deposition source, an atmosphere, and the degree of vacuum, and is selected to be an appropriate ratio. The anode and the cathode may be respectively constituted of two or more layers, as occasion demand.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is produced from the above electrically conductive material by vapor deposition method, sputtering method, etc., so as to ensure a desirable transparency thereof. The electrode disposed on a light emitting surface of the device preferably has a light transmittance of 10% or more. The substrate is not particularly limited as long as it has a good mechanical and thermal strength as well as a good transparency. Examples of the transparent films include films of resins such as polyethylene, copolymers of ethylene and vinyl acetate, copolymers of ethylene and vinyl alcohol, polypropylene, polystyrene, polymethylmethacrylate, polyvinyl chloride, polyvinyl alcohol, polyvinyl butyral, nylon, polyether ether ketone, polysulfone, polyethersulfone, copolymers of tetrafluoroethylene and perfluoroalkyl vinyl ethers, polyvinyl fluoride, copolymers of tetrafluoroethylene and ethylene, copolymers of tetrafluoroethylene and hexafluoropropylene, polychlorotrifluoroethylene, polyvinylidene fluoride, polyesters, polycarbonates, polyurethanes, polyimide, polyether imides, polyimide polypropylene, etc.

The respective layers of the organic EL device of the present invention may be formed by either a dry film-forming method such as vacuum deposition, sputtering, plasma and ion-plating, or a wet film-forming method such as spin-coating, dipping and flow-coating. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, so sufficient luminance of light emission cannot be obtained even when an electric field is applied. The suitable thickness of the respective layers is usually in the range of from 5 nm to 10 μm and preferably from 10 nm to 0.2 μm.

In the wet film-forming method, materials for forming the respective layers are dissolved or dispersed in a suitable solvent such as ethanol, chloroform, tetrahydrofuran and dioxane to form a thin film thereof. The solvent used for forming the respective layers is not particularly limited.

As a solution suited for such a wet process of film formation, an organic-electroluminescent-material-containing solution containing the trinaphthyl monoamine or a derivative thereof as the material for the organic EL and a solvent can be used.

Further, it is preferable that the material for the organic EL contains the host material and the dopant material, that the dopant material is the trinaphthyl monoamine or the derivative thereof in the present invention, and that the host material is at least one kind selected among a compound represented by the general formula (2a), general formula (2b), general formula (2c) and general formula (2d).

Also, suitable resins or additives may be added to the respective organic thin film layers for the purposes of improving a film-forming property, preventing formation of pinholes in the resultant film, etc.

Examples of the resins usable for the above purposes include electrically insulating resins such as polystyrenes, polycarbonates, polyarylates, polyesters, polyamides, polyurethanes, polysulfones, polymethylmethacrylate, polymethylacrylate and celluloses as well as copolymers thereof, photoconductive resins such as poly-N-vinyl carbazole and polysilanes, and electrically conductive resins such as polythiophene and polypyrrole. Examples of the additive include antioxidants, ultraviolet light absorbents and plasticizers.

The organic EL device of the present invention can find use in applications including: a flat luminous member such as a flat panel display of a wall hanging television; a light source for the backlight, meters, or the like of a copying machine, a printer, or a liquid crystal display; a display panel; and a signal lamp. Further, the material of the present invention can be used not only for organic EL devices but also in other applications such as electrophotographic members, photoelectric converters, solar cells, image sensors, etc.

EXAMPLES

Synthesis 1 (Synthesis of D-12)

(1) Synthesis of 2-bromo-6-styrylnaphthalene

Under an atmospheric argon gas flow, 23.5 g (100 mmol) of 2-bromo-naphthaldehyde, 7.7 g (100 mmol) of benzyl diethoxy phosphoric acid ester, 13.5 g (120 mmol) of potassium tert-butoxide, and 200 mL of desiccated tetrahydrofuran were placed into a three neck flask equipped with a cooling pipe and having a capacity of 500 mL, and the resultant mixture solution was stirred at a room temperature for 1 night. After completion of the reaction, adding 200 ml of water into the resultant solution, crystals were separated by filtration. After washing the resultant crude product using water and methanol, 17.9 g of an desired compound (2-bromo-6-styrylnaphthalene) (white crystal) was obtained (58% yield).

(2) Bis(2-styrylnaphthalene)amine

Under an atmospheric argon gas flow, 15.4 g (50 mmol) of 2-bromo-6-styrylnaphthalene, 1.7 g (30 mmol) of acetamide, 0.48 g (2.5 mmol) of copper iodide, 13.8 g (100 mmol) of potassium carbonate and 500 mL of desiccated xylene were placed into a three neck flask equipped with a cooling pipe and having a capacity of 1 L, and the resultant solution was refluxed under heating for 3 days. After completion of the reaction, adding 500 ml of water into the resultant solution, crystals were separated by filtration. The resultant crude product was re-crystallized through ethyl acetate to obtain 17.9 g of amide compound.

Subsequently, 17.9 g of amide compound, 3.4 g (60 mmol) of potassium hydroxide, 10 mL of water, 200 mL of ethanol and 200 mL of xylene were placed into an eggplant flask equipped with a cooling pipe and having a capacity of 1 L, the resultant mixture solution was refluxed under heating for 8 hours. After completion of the reaction, crystals were separated by filtration and washed with methanol. The resultant crude product was re-crystallized through toluene to obtain 8.3 g of the desired compound (bis(2-styrylnaphthalene) amine) (35% yield).

(3) Synthesis of Compound (D-12)

Under an atmospheric argon gas flow, 3.1 g (10 mmol) of 2-bromo-6-styrylnaphthalene, 4.7 g (10 mmol) of bis(2-styrylnaphthalene)amine, 0.03 g (1.5 mol %) of palladium acetate, 0.06 g (3 mol %) of tri-tert-butylphosphine, 1.2 g (12 mmol) of sodium tert-butoxide, and 100 mL of desiccated toluene were placed into a three-neck flask equipped with a cooling pipe and having a capacity of 300 mL, and the resultant mixture solution was stirred under heating at 100° C. for 1 night. After completion of the reaction, the precipitated crystals were separated from the reaction solution by filtration, and washed with 50 mL of toluene and 100 mL of methanol, to obtain 4.2 g of a light yellow powder. The pale yellow powders were identified as Compound (D-12) from the result in accordance with Field Desorption Mass Spectrum (FD-MS) measurement and $^1$H-NMR measurement (yield: 60%). $^1$H-NMR spectrum is shown in FIG. 1.
[Peak absorption wavelength: 403 nm, Greatest fluorescent wavelength: 457 nm (toluene solution)]

Synthesis 2 (Synthesis of D-10)

Figure 2:
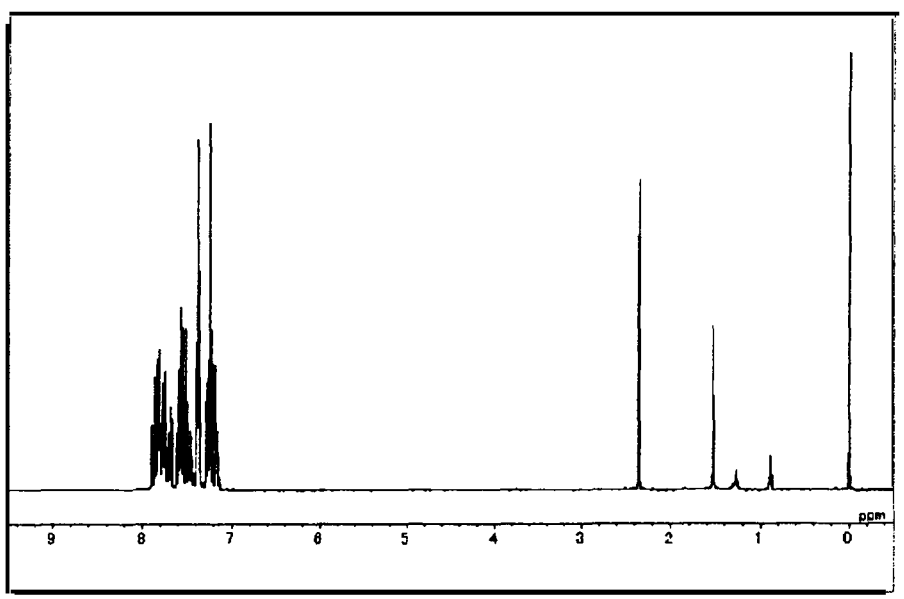
FIG. 2 is a diagram showing $^1$H-NMR spectrum of Compound D-10, which is obtained in Synthesis Example 2.

Under an atmospheric argon gas flow, 3.6 g (10 mmol) of 2-((E)-2-(2-bromonaphthalene)vinyl)naphthalene, 4.7 g (10 mmol) of bis(2-styrylnaphthalene)amine, 0.03 g (1.5 mol %) of palladium acetate, 0.06 g (3 mol %) of tri-tert-butylphosphine, 1.2 g (12 mmol) of sodium tert-butoxide, and 100 mL of desiccated toluene were placed into a three-neck flask equipped with a cooling pipe and having a capacity of 300 mL, and the resultant mixture solution was stirred under heating at 100° C. for 1 night. After completion of the reaction, the precipitated crystals were separated from the reaction solution by filtration, and washed with 50 mL of toluene and 100 mL of methanol, thereby obtaining 3.8 g of a light yellow powder. The pale yellow powders were identified as Compound (D-10) from the result in accordance with Field Desorption Mass Spectrum (FD-MS) measurement and $^1$H-NMR measurement (yield: 50%). $^1$H-NMR spectrum is shown in FIG. 2.
[Peak absorption wavelength: 405 nm, Greatest fluorescent wavelength: 459, 482 nm (toluene solution)]

Example 1

A 120 nm-thick transparent electrode made of indium tin oxide was formed on a glass substrate having a size of 25 mm×75 mm×1.1 mm. The transparent electrode functions as an anode.

The glass substrate with the transparent electrode was cleaned by irradiation of Ultra Violet ray and ozone. The thus cleaned glass substrate with the transparent electrode was mounted to a vacuum vapor deposition apparatus.

First, N',N"-bis[4-(diphenylamino)phenyl]-N',N"-diphenylbiphenyl-4,4'-diamine was vapor-deposited to form a hole injecting layer having a thickness of 60 nm, and then N,N,N', N'-tetrakis(4-biphenyl)-4,4'-benzidine was vapor-deposited on the hole injecting layer to form a hole transporting layer having a thickness of 20 nm. Then, anthracene derivative (2a-1) being a host material and trinaphthyl monoamine derivative (D-8) being a doping material were simultaneously deposited in such a manner that a weight ratio between them would be 40:2, a light emitting layer with the thickness of 40 nm was formed.

Next, tris(8-hydroxyquinolinato)aluminum was vapor-deposited on the light emitting layer to form an electron injecting layer having a thickness of 20 nm.

Subsequently, lithium fluoride was deposited up to 1 nm in thickness and then, aluminum was deposited up to 150 nm in thickness. The aluminum/lithium fluoride functions as a cathode.

Measured results of a device performance (luminance of light emission) driven at current density of 10 mA/cm² and a half lifetime from initial brightness of 100 cd/cm² about the resultant organic EL device are shown in Table 1 below.

Examples 2 to 5

Organic EL devices were fabricated in the same manner as Example 1 using trinaphthyl monoamine derivatives shown in Table 1 below instead of trinaphthyl monoamine derivative (D-8), and the evaluation results in the same manner as Example 1 are shown in Table 1.

Examples 6 and 7

Organic EL devices were fabricated in the same manner as Example 1 using the compounds shown in Table 1 below instead of anthracene derivative (2a-1), and the evaluation results in the same manner as Example 1 are shown in Table 1.

Comparative Examples 1 to 3

Organic EL devices were fabricated in the same manner as Example 1 selecting the compounds below as described in Table 1 instead of trinaphthyl monoamine derivative (D-8), and the evaluation results in the same manner as Example 1 are shown in Table 1.

(A)

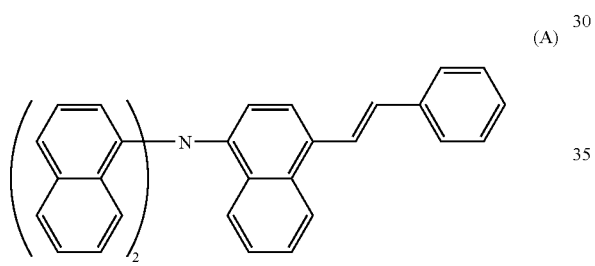

(B)

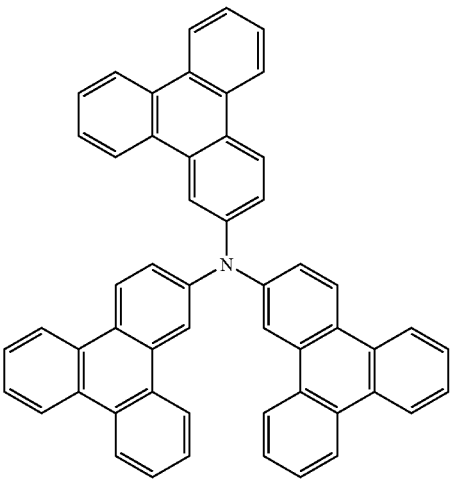

(C)

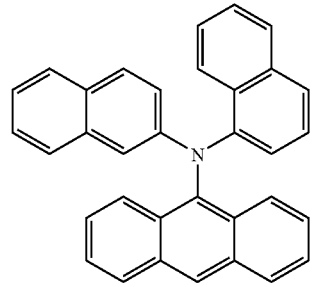

TABLE 1

|  | Example 1 | Example 2 | Example 3 | Example 4 | Example 5 |
|---|---|---|---|---|---|
| Host | 2a-1 | 2a-1 | 2a-1 | 2a-1 | 2a-1 |
| Dopant | D-8 | D-10 | D-12 | D-13 | D-15 |
| Driving voltage (V) | 6.5 | 6.5 | 6.5 | 6.5 | 6.5 |
| Color of light emission | Blue | Blue | Blue | Blue | Blue |
| Luminance of light emission (cd/m²) | 300 | 400 | 380 | 430 | 500 |
| Luminescence half life (hours) | 8,000 | 9,000 | >10,000 | >10,000 | >10,000 |

|  | Example 6 | Example 7 | Comparative Example 1 | Comparative Example 2 | Comparative Example 3 |
|---|---|---|---|---|---|
| Host | 2b-9 | 2d-1 | 2a-1 | 2a-1 | 2a-1 |
| Dopant | D-12 | D-12 | (A) | (B) | (C) |
| Driving voltage (V) | 6.5 | 6.5 | 6.5 | 6.5 | 6.5 |
| Color of light emission | Blue | Blue | Blue | Bluish green | Bluish green |
| Luminance of light emission (cd/m²) | 330 | 340 | 200 | 800 | 700 |
| Luminescence half life (hours) | 9,000 | 8,000 | 3,000 | >10,000 | >10,000 |

Table 1 verifies the observation of blue light emission about the organic EL devices using trinaphthyl monoamine. However, when the substitution site of naphthyl groups are entirely 1-positions (Comparative Example 1), degradation about the efficiency of light emission was observed. Further, employments of fused aromatic ring having more carbon atoms than naphthyl group (Comparative Examples 2 and 3) changed colors of light emission into bluish green, and reduction of blue purity was observed.

INDUSTRIAL APPLICABILITY

As explained above in detail, the organic EL device using the tri naphthyl monoamine or the derivative thereof according to the present invention exhibits excellent luminance of light emission under a low applied voltage, obtaining an enhanced efficiency of light emission and further, the device is free from deterioration in properties even after being used for a long period of time and, therefore, has a prolonged lifetime. Thus, the organic EL device is useful as a surface light-emitting member for wall-type televisions or a light source such as a backlight for displays.

The invention claimed is:
1. A trinaphthyl monoamine or a derivative thereof according to any one of formulae (I) to (III):

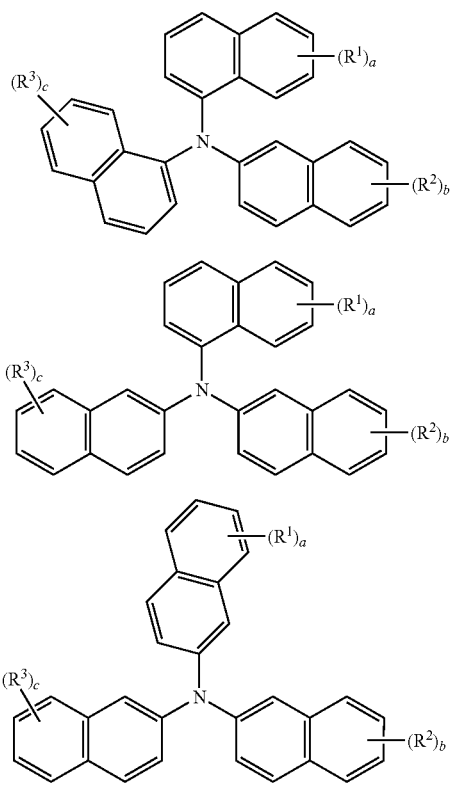

wherein:
each of $R^1$ to $R^3$ is independently selected from the group consisting of:
a substituted or unsubstituted alkyl group having 1 to 50 carbon atoms;
a substituted or unsubstituted aryl group having 6 to 50 carbon atoms;
a substituted or unsubstituted aralkyl group having 7 to 50 carbon atoms;
a substituted or unsubstituted cycloalkyl group having 3 to 50 carbon atoms;
a substituted or unsubstituted alkoxyl group having 1 to 50 carbon atoms;
a substituted or unsubstituted arylalkenyl group having 8 to 50 carbon atoms;
a substituted or unsubstituted aryloxy group having 6 to 50 carbon atoms;
a substituted or unsubstituted silyl group having 1 to 20 carbon atoms;
a substituted or unsubstituted heterocyclic group having 5 to 50 carbon atoms; and
a substituent represented by the structure (A):

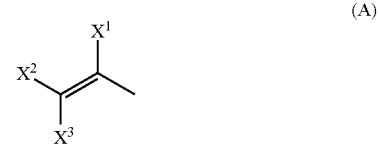

wherein:
each of $X^1$ to $X^3$ is independently selected from the group consisting of:
a hydrogen atom;
a substituted or unsubstituted alkyl group having 1 to 50 carbon atoms;
a substituted or unsubstituted aryl group having 6 to 50 carbon atoms;
a substituted or unsubstituted cycloalkyl group having 3 to 50 carbon atoms; and
a substituted or unsubstituted heterocyclic group having 5 to 50 carbon atoms;
a, b, and c each independently represents an integer of 0 to 7;
when a is 2 or greater, plural $R^1$'s may be identical to or different from each other, and adjacent $R^1$'s are not bonded with each other;
when b is 2 or greater, plural $R^2$'s may be identical to or different from each other, and adjacent $R^2$'s are not bonded with each other; and
when c is 2 or greater, plural $R^3$'s may be identical to or different from each other, and adjacent $R^3$'s are not bonded with each other.

2. The trinaphthyl monoamine or derivative thereof according to claim 1, wherein the trinaphthyl monoamine or derivative thereof is a trinaphthyl monoamine or derivative thereof according to formula (I'):

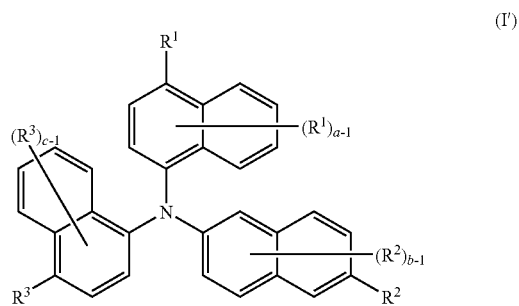

with the proviso that a, b and c each independently represents an integer of 1 to 7.

3. The trinaphthyl monoamine or derivative thereof according to claim 1, wherein the trinaphthyl monoamine or derivative thereof is a trinaphthyl monoamine or derivative thereof according to formula (II'):

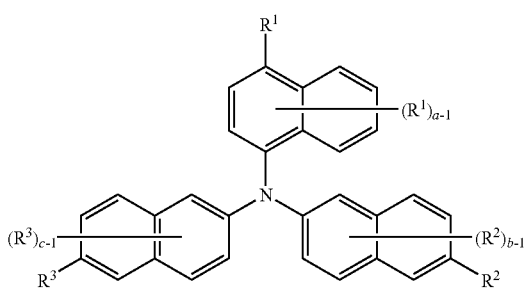

with the proviso that a, b and c each independently represents an integer of 1 to 7.

4. The trinaphthyl monoamine or derivative thereof according to claim 1, wherein the trinaphthyl monoamine or derivative thereof is a trinaphthyl monoamine or derivative thereof according to formula (III'):

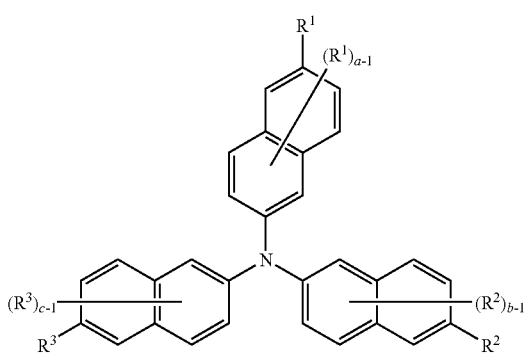

with the proviso that a, b and c each independently represents an integer of 1 to 7.

5. The trinaphthyl monoamine or derivative thereof according to claim 2, wherein the trinaphthyl monoamine or derivative thereof is a trinaphthyl monoamine or derivative thereof according to formula (I"):

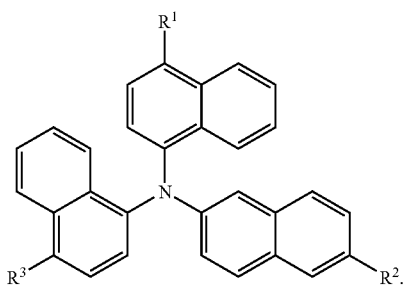

6. The trinaphthyl monoamine or derivative thereof according to claim 3, wherein the trinaphthyl monoamine or derivative thereof is a trinaphthyl monoamine or derivative thereof according to formula (II"):

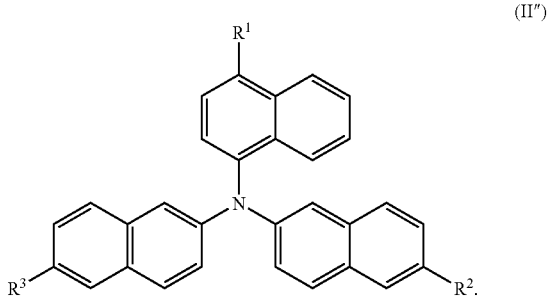

7. The trinaphthyl monoamine or derivative thereof according to claim 4, wherein the trinaphthyl monoamine or derivative thereof is a trinaphthyl monoamine or derivative thereof according to formula (III"):

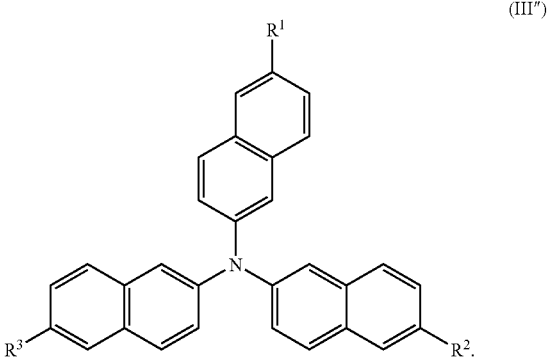

8. An organic electroluminescence device comprising a dopant material, wherein the dopant material comprises the trinaphthyl monoamine or a derivative thereof according to claim 1.

9. An organic electroluminescence device, comprising:
a cathode;
an anode: and
at least one organic thin film layer sandwiched between the cathode and the anode;
wherein:
the at least one organic thin film layer comprises at least one light emitting layer; and
the at least one organic thin film layer comprises the trinaphthyl monoamine or derivative thereof according to claim 1.

10. An organic electroluminescence device, comprising:
a cathode;
an anode; and
at least one organic thin film layer sandwiched between the cathode and the anode;
wherein:
the at least one organic thin film layer comprises at least one light emitting layer; and
the at least one the light emitting layer comprises the trinaphthyl monoamine or a derivative thereof according to claim 1.

11. The organic electroluminescence device according to claim 9, wherein the at least one light emitting layer comprises the trinaphthyl monoamine or derivative thereof and a compound according to formula (2a):

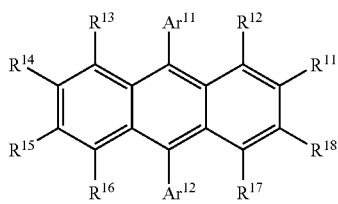

wherein:
each of $Ar^{11}$ and $Ar^{12}$ independently represents a group derived from a substituted or unsubstituted aromatic ring having 6 to 20 carbon atoms forming a ring, the aromatic ring being optionally substituted by 1 or more substituents selected from the group consisting of:
a substituted or unsubstituted aryl group having 6 to 50 carbon atoms forming a ring;
a substituted or unsubstituted alkyl group having 1 to 50 carbon atoms;
a substituted or unsubstituted cycloalkyl group having 3 to 50 carbon atoms;
a substituted or unsubstituted alkoxy group having 1 to 50 carbon atoms;
a substituted or unsubstituted aralkyl group having 6 to 50 carbon atoms;
a substituted or unsubstituted aryloxy group having 6 to 50 ring atoms;
a substituted or unsubstituted arylthio group having 6 to 50 ring atoms;
a substituted or unsubstituted alkoxycarbonyl group having 2 to 50 carbon atoms;
a substituted or unsubstituted silyl group;
a carboxyl group;
a halogen atom;
a cyano group; a nitro group; and
a hydroxyl group;
when the aromatic ring is substituted by 2 or more substituents, the substituents may be identical to or different from each other and neighboring substituents may be bonded with each other to form a saturated or unsaturated cyclic structure; and
each of $R^{11}$ to $R^{18}$ is independently selected from the group consisting of:
a hydrogen atom;
a substituted or unsubstituted aryl group having 6 to 50 carbon atoms forming a ring;
a substituted or unsubstituted heteroaryl group having 5 to 50 ring atoms;
a substituted or unsubstituted alkyl group having 1 to 50 carbon atoms;
a substituted or unsubstituted cycloalkyl group having 3 to 50 carbon atoms;
a substituted or unsubstituted alkoxy group having 1 to 50 carbon atoms;
a substituted or unsubstituted aralkyl group having 6 to 50 carbon atoms;
a substituted or unsubstituted aryloxy group having 6 to 50 ring atoms;
a substituted or unsubstituted arylthio group having 6 to 50 ring atoms;
a substituted or unsubstituted alkoxycarbonyl group having 2 to 50 carbon atoms;
a substituted or unsubstituted silyl group;
a carboxyl group;
a halogen atom;
a cyano group;
a nitro group; and
a hydroxyl group.

12. The organic electroluminescence device according to claim 11, wherein $Ar^{11}$ and $Ar^{12}$ are different groups.

13. The organic electroluminescence device according to claim 9, wherein the at least one light emitting layer comprises the trinaphthyl monoamine or derivative thereof and a pyrene ring compound according to formula (2b):

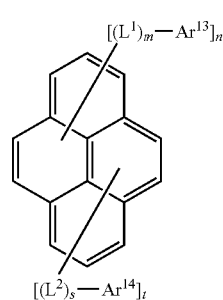

wherein:
each of $Ar^{13}$ and $Ar^{14}$ independently represents a substituted or unsubstituted aryl group having 6 to 50 carbon atoms forming a ring;
each of $L^1$ and $L^2$ is independently selected from the group consisting of:
a substituted or unsubstituted phenylene group;
a substituted or unsubstituted naphthalenylene group;
a substituted or unsubstituted fluorenylene group; and
a substituted or unsubstituted dibenzosilolylene group;
m represents an integer of 0 to 2;
n represents an integer of 1 to 4;
s represents an integer of 0 to 2;
t represents an integer of 0 to 4;
$L^1$ or $Ar^{13}$ is bonded to any of 1- to 5-positions of the pyrene ring compound; and
$L^2$ or $Ar^{14}$ is bonded to any of 6- to 10-positions of the pyrene ring compound.

14. The organic electroluminescence device according to claim 9, wherein the at least one light emitting layer comprises the trinaphthyl monoamine or derivative thereof and a compound according to formula (2c):

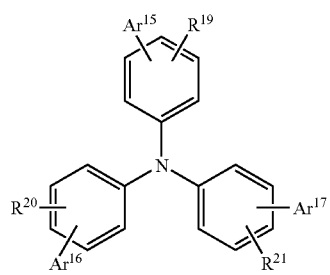

wherein:
each of $Ar^{15}$, $Ar^{16}$ and $Ar^{17}$ is independently selected from the group consisting of a group having an anthracene structure, a group having a phenanthrene structure, and a group having a pyrene structure; and
each of $R^{19}$, $R^{20}$ and $R^{21}$ independently represents a hydrogen atom or a substituent.

15. The organic electroluminescence device according to claim 9, wherein the at least one light emitting layer comprises the trinaphthyl monoamine or derivative thereof and a compound according to formula (2d):

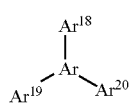
(2d)

wherein:
each of $Ar^{18}$, $Ar^{19}$ and $Ar^{20}$ independently represents an aryl group having 6 to 50 carbon atoms forming a ring; the aryl group may be substituted by 1 or more substituents; at least one of $Ar^{18}$, $Ar^{19}$, $Ar^{20}$, and substituents thereof comprises a fused ring aryl structure having 10 to 20 carbon atoms forming a ring or a fused ring heteroaryl structure having 6 to 20 carbon atoms forming a ring; and
Ar represents a trivalent group derived from an aromatic ring or a heteroaromatic ring.

16. A solution, comprising an organic electroluminescent material and a solvent, wherein the organic electroluminescent material comprises the trinaphthyl monoamine or derivative thereof according to claim 1.

17. The solution according to claim 16, wherein:
the trinaphthyl monoamine or derivative thereof is a dopant material; and
the organic electroluminescent material further comprises a host material comprising a compound according to formula (2a):

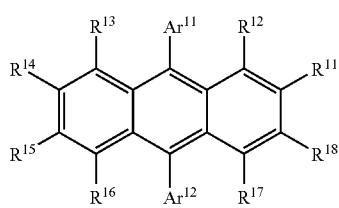
(2a)

wherein:
each of $Ar^{11}$ and $Ar^{12}$ independently represents a group derived from a substituted or unsubstituted aromatic ring having 6 to 20 carbon atoms forming a ring, the aromatic ring being optionally substituted by 1 or more substituents selected from the group consisting of:
a substituted or unsubstituted aryl group having 6 to 50 carbon atoms forming a ring;
a substituted or unsubstituted alkyl group having 1 to 50 carbon atoms;
a substituted or unsubstituted cycloalkyl group having 3 to 50 carbon atoms;
a substituted or unsubstituted alkoxy group having 1 to 50 carbon atoms;
a substituted or unsubstituted aralkyl group having 6 to 50 carbon atoms;
a substituted or unsubstituted aryloxy group having 6 to 50 ring atoms;
a substituted or unsubstituted arylthio group having 6 to 50 ring atoms;
a substituted or unsubstituted alkoxycarbonyl group having 2 to 50 carbon atoms;
a substituted or unsubstituted silyl group;
a carboxyl group;
a halogen atom;
a cyano group; a nitro group; and
a hydroxyl group;
when the aromatic ring is substituted by 2 or more substituents, the substituents may be identical to or different from each other and neighboring substituents may be bonded with each other to form a saturated or unsaturated cyclic structure; and
each of $R^{11}$ to $R^{18}$ is independently selected from the group consisting of:
a hydrogen atom;
a substituted or unsubstituted aryl group having 6 to 50 carbon atoms forming a ring;
a substituted or unsubstituted heteroaryl group having 5 to 50 ring atoms;
a substituted or unsubstituted alkyl group having 1 to 50 carbon atoms;
a substituted or unsubstituted cycloalkyl group having 3 to 50 carbon atoms;
a substituted or unsubstituted alkoxy group having 1 to 50 carbon atoms;
a substituted or unsubstituted aralkyl group having 6 to 50 carbon atoms;
a substituted or unsubstituted aryloxy group having 6 to 50 ring atoms;
a substituted or unsubstituted arylthio group having 6 to 50 ring atoms;
a substituted or unsubstituted alkoxycarbonyl group having 2 to 50 carbon atoms;
a substituted or unsubstituted silyl group;
a carboxyl group;
a halogen atom;
a cyano group;
a nitro group; and
a hydroxyl group.

18. The organic electroluminescence device according to claim 10, wherein the at least one light emitting layer further comprises a compound according to formula (2a):

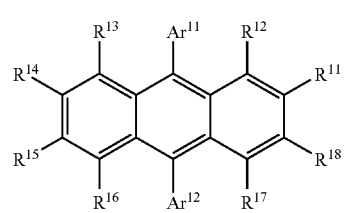
(2a)

wherein:
each of $Ar^{11}$ and $Ar^{12}$ independently represents a group derived from a substituted or unsubstituted aromatic ring having 6 to 20 carbon atoms forming a ring, the aromatic ring being optionally substituted by 1 or more substituents selected from the group consisting of:

a substituted or unsubstituted aryl 20 group having 6 to 50 carbon atoms forming a ring;

a substituted or unsubstituted alkyl group having 1 to 50 carbon atoms;

a substituted or unsubstituted cycloalkyl group having 3 to 50 carbon atoms a substituted or unsubstituted alkoxy group having 1 to 50 carbon atoms;

a substituted or unsubstituted aralkyl group having 6 to 50 carbon atoms;

a substituted or unsubstituted aryloxy group having 6 to 50 ring atoms;

a substituted or unsubstituted arylthio group having 6 to 50 ring atoms;

a substituted or unsubstituted alkoxycarbonyl group having 2 to 50 carbon atoms;

a substituted or unsubstituted silyl group;

a carboxyl group;

a halogen atom;

a cyano group;

a nitro group; and a hydroxyl group;

when the aromatic ring is substituted by 2 or more substituents, the substituents may be identical to or different from each other and neighboring substituents may be bonded with each other to form a saturated or unsaturated cyclic structure; and each $R^{11}$ to $R^{18}$ is independently selected from the group consisting of:

a hydrogen atom;

a substituted or unsubstituted aryl group having 6 to 50 carbon atoms forming a ring;

a substituted or unsubstituted heteroaryl group having 5 to 50 ring atoms;

a substituted or unsubstituted alkyl group having 1 to 50 carbon atoms;

a substituted or unsubstituted cycloalkyl group having 3 to 50 carbon atoms;

a substituted or unsubstituted alkoxy group having 1 to 50 carbon atoms;

a substituted or unsubstituted aralkyl group having 6 to 50 carbon atoms;

a substituted or unsubstituted aryloxy group having 6 to 50 ring atoms;

a substituted or unsubstituted arylthio group having 6 to 50 ring atoms;

a substituted or unsubstituted alkoxycarbonyl group having 2 to 50 carbon atoms;

a substituted or unsubstituted silyl group;

a carboxyl group;

a halogen atom;

a cyano group;

a nitro group; and a hydroxyl group.

19. The organic electroluminescence device according to claim 10, wherein the at least one light emitting layer further comprises a pyrene ring compound according to formula (2b):

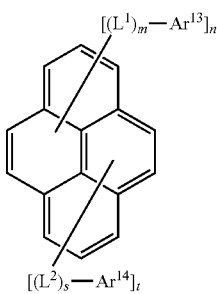

(2b)

wherein:

each $Ar^{13}$ and $Ar^{14}$ independently represents a substituted or unsubstituted aryl group having 6 to 50 carbon atoms forming a ring;

each of $L^1$ and $L^2$ is independently selected from the group consisting of:

a substituted or unsubstituted phenylene group;

a substituted or unsubstituted naphthalenylene group;

a substituted or unsubstituted fluorenylene group; and a substituted or unsubstituted dibenzosilolylene group;

m represents an integer of 0 to 2;

n represents an integer of 1 to 4;

a represents an integer of 0 to 2;

t represents an integer of 0 to 4; and $L^1$ or $Ar^{13}$ is bonded to any of 1- to 5-positions of the pyrene ring compound; and $L^2$ or $Ar^{14}$ is bonded to any of 6- to 10-positions of the pyrene ring compound.

20. The organic electroluminescence device according to claim 10, wherein the at least one light emitting layer further comprises a compound according to formula (2c):

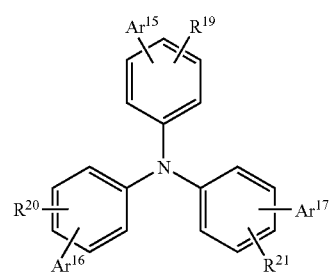

(2c)

wherein:

each of $Ar^{15}$, $Ar^{16}$ and $Ar^{17}$ is independently selected from the group consisting of a group having anthracene structure, a group having phenanthrene structure, and a group having pyrene structure; and each of $R^{19}$, $R^{20}$ and $R^{21}$ independently represents a hydrogen atom or a substituent.

21. The organic electroluminescence device according to claim 10, wherein the at least one light emitting layer further comprises a compound according to formula (2d):

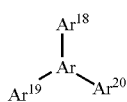

(2d)

where: $Ar^{18}$, $Ar^{19}$ and $Ar^{20}$ each independently represents an aryl group having 6 to 50 carbon atoms forming a ring;

the aryl group may be substituted by 1 or more substituents;

at least one of the aryl groups represented by $Ar^{18}$, $Ar^{19}$, $Ar^{20}$, and those substituents has a fused ring aryl structure having 10 to 20 carbon atoms forming a ring or a fused ring heteroaryl structure having 6 to 20 carbon atoms forming a ring; and Ar represents a trivalent group derived from an aromatic ring or a heteroaromatic ring.

22. The solution according to claim 16, wherein:

the trinaphthyl monoamine or derivative thereof is a dopant material; and the organic electroluminescent material further comprises a host material comprising a pyrene ring compound according to formula (2b):

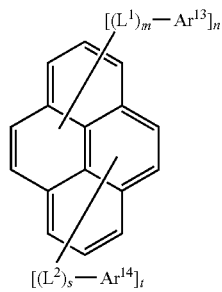

(2b)

wherein:

each of $Ar^{13}$ and $Ar^{14}$ independently represents a substituted or unsubstituted aryl group having 6 to 50 carbon atoms forming a ring;

each of $L^1$ and $L^2$ is independently selected from the group consisting of:
  a substituted or unsubstituted phenylene group;
  a substituted or unsubstituted naphthalenylene group;
  a substituted or unsubstituted fluorenylene group; and
  a substituted or unsubstituted dibenzosilolylene group;

m represents an integer of 0 to 2;

n represents an integer of 1 to 4;

s represents an integer of 0 to 2;

t represents an integer of 0 to 4;

$L^1$ or $Ar^{13}$ is bonded to any of 1- to 5-positions of the pyrene ring compound; and $L^2$ or $Ar^{14}$ is bonded to any of 6- to 10-positions of the pyrene ring compound.

23. The solution according to claim 16, wherein:

the trinaphthyl monoamine or derivative thereof is a dopant material; and the organic electroluminescent material further comprises a host material comprising a compound according to formula (2c):

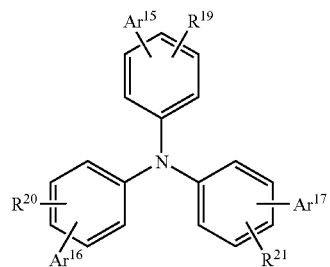

(2c)

wherein:

each of $Ar^{15}$, $Ar^{16}$ and $Ar^{17}$ is independently selected from the group consisting of a group having an anthracene structure, a group having a phenanthrene structure, and a group having a pyrene structure; and each of $R^{19}$, $R^{20}$ and $R^{21}$ independently represents a hydrogen atom or a substituent.

24. The solution according to claim 16, wherein:

the trinaphthyl monoamine or derivative thereof is a dopant material; and the organic electroluminescent material further comprises a host material comprising a compound according to formula (2d):

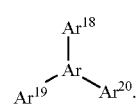

(2d)

wherein:

each of $Ar^{18}$, $Ar^{19}$ and $Ar^{20}$ independently represents an aryl group having 6 to 50 carbon atoms forming a ring;

the aryl group may be substituted by 1 or more substituents;

at least one of $Ar^{18}$, $Ar^{19}$, $Ar^{20}$, and substituents thereof comprises a fused ring aryl structure having 10 to 20 carbon atoms forming a ring or a fused ring heteroaryl structure having 6 to 20 carbon atoms forming a ring; and Ar represents a trivalent group derived from an aromatic ring or a heteroaromatic ring.

\* \* \* \* \*